(12) United States Patent
Frickmann et al.

(10) Patent No.: US 12,227,784 B2
(45) Date of Patent: Feb. 18, 2025

(54) ENZYME BLENDS AND PROCESSES FOR IMPROVING THE NUTRITIONAL QUALITY OF ANIMAL FEED

(71) Applicant: NOVOZYMES A/S, Bagsvaerd (DK)

(72) Inventors: Jesper Frickmann, Raleigh, NC (US); Kendra Stallings, Wake Forest, NC (US); Dan Pettersson, Lynge (DK); Mads Brøgger Pedersen, Bagsvaerd (DK); Harold Cale Smith, Franklinton, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/646,709

(22) PCT Filed: Sep. 12, 2018

(86) PCT No.: PCT/US2018/050568
§ 371 (c)(1),
(2) Date: Mar. 12, 2020

(87) PCT Pub. No.: WO2019/055455
PCT Pub. Date: Mar. 21, 2019

(65) Prior Publication Data
US 2020/0263207 A1 Aug. 20, 2020

Related U.S. Application Data

(60) Provisional application No. 62/559,163, filed on Sep. 15, 2017.

(51) Int. Cl.
*C12P 7/06* (2006.01)
*C12N 9/24* (2006.01)
*C12P 19/02* (2006.01)
*C12P 19/14* (2006.01)

(52) U.S. Cl.
CPC ............ *C12P 7/06* (2013.01); *C12P 19/02* (2013.01); *C12P 19/14* (2013.01); *C12Y 302/01004* (2013.01); *C12Y 302/01091* (2013.01); *C12Y 302/01136* (2013.01)

(58) Field of Classification Search
CPC ... C12N 9/24; C12P 19/14; C12P 7/06; C12Y 302/01004; C12Y 302/01091
See application file for complete search history.

(56) References Cited

U.S. PATENT DOCUMENTS

| | | | | |
|---|---|---|---|---|
| 5,424,202 A * | 6/1995 | Ingram | ................... | C12N 9/88 |
| | | | | 435/161 |
| 9,816,113 B2 * | 11/2017 | Noda | .................... | C12P 7/10 |
| 10,793,926 B2 * | 10/2020 | St. John | .............. | C13K 13/002 |
| 2012/0045812 A1 * | 2/2012 | Bergsma | ............. | C12N 9/2428 |
| | | | | 435/167 |
| 2015/0150282 A1 | 6/2015 | Arent et al. | | |
| 2016/0040203 A1 | 2/2016 | St. John et al. | | |
| 2016/0333332 A1 | 11/2016 | Teunissen et al. | | |
| 2018/0340191 A1 | 11/2018 | Kreel | | |
| 2019/0309240 A1 * | 10/2019 | Kraemer | ................ | A23K 50/30 |
| 2019/0330577 A1 * | 10/2019 | Cramer | .................... | C12P 7/64 |

FOREIGN PATENT DOCUMENTS

| | | | |
|---|---|---|---|
| CN | 104619193 | A | 5/2015 |
| CN | 106103707 | A | 11/2016 |
| JP | 182675 | * | 9/2011 |
| WO | 2017/148389 | A1 | 9/2017 |
| WO | 2018007154 | A1 | 1/2018 |
| WO | 2018/042433 | A1 | 3/2018 |
| WO | 2018/095408 | A1 | 5/2018 |
| WO | 2018234465 | A1 | 12/2018 |

OTHER PUBLICATIONS

Cazypedia, glycosyl Hydrolase Family 30/subf8, Nov. 2021.*
Cinelli et al, 2015, Fuel 150, 721-729.
Hagiwara et al 2020, Bioscience, Biotechnology, and Biochemistry 84(3) 640-650.
Nebesny et al, 1998, Zywnosc technologia jakosc 4(17), 181-189.
Shamala et al, 1986, Starch 38, 428-432.
Sugimoto et al, 2012, J Ind Microbiol Biotechnol 39, 605-612.
Corretto et al, 2015, EBI Accession No. UNIPROT—A0A0F2C6B8.
Linares-Pasten et al, 2018, Current protein and peptide science 19, 48-67.
John et al., Acta crystallographica, 2014, 2950-2958, D70.
John et al., EBS letters, 2010, 4435-4441, 584(21).
Exhibit A—Devos et al., "Practical Limits of Function Prediction," Proteins: Structure, Function, and Genetics 41: 98-107 (2000).

* cited by examiner

*Primary Examiner* — Maryam Monshipouri
(74) *Attorney, Agent, or Firm* — David A. Fazzolare; Kelly K. Reynolds

(57) ABSTRACT

The present invention relates to a process for improving the nutritional quality of distillers dried grains (DGS) or distillers dried grains with solubles (DDGS) produced as a co-product of a fermentation product production process, processes for producing fermentation products, as well as enzyme blends used in the processes.

24 Claims, 18 Drawing Sheets

Specification includes a Sequence Listing.

ENZYME BLENDS AND PROCESSES FOR IMPROVING THE NUTRITIONAL QUALITY OF ANIMAL FEED

CROSS-REFERENCE TO RELATED APPLICATIONS

This application is a 35 U.S.C. 371 national application of international application no. PCT/US2018/050568 filed Sep. 12, 2018, which claims priority or the benefit under 35 U.S.C. 119 of U.S. application No. 62/559,163 filed Sep. 15, 2017, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to a process for improving the nutritional quality of distillers dried grains (DGS) or distillers dried grains with solubles (DDGS) produced as a co-product of a fermentation product production process, processes for producing fermentation products, as well as enzyme blends used in the processes.

BACKGROUND OF THE INVENTION

Processes for producing fermentation products, such as ethanol, from a starch or lignocellulose containing material are well known in the art. The preparation of the starch containing material such as corn for utilization in such fermentation processes typically begins with grinding the corn in a dry-grind or wet-milling process. Wet-milling processes involve fractionating the corn into different components where only the starch fraction enters the fermentation process. Dry-grind processes involve grinding the corn kernels into meal and mixing the meal with water and enzymes. Generally, two different kinds of dry-grind processes are used. The most commonly used process, often referred to as a "conventional process," includes grinding the starch-containing material and then liquefying gelatinized starch at a high temperature using typically a bacterial alpha-amylase, followed by simultaneous saccharification and fermentation (SSF) carried out in the presence of a glucoamylase and a fermentation organism. Another well-known process, often referred to as a "raw starch hydrolysis" process (RSH process), includes grinding the starch-containing material and then simultaneously saccharifying and fermenting granular starch below the initial gelatinization temperature typically in the presence of an acid fungal alpha-amylase and a glucoamylase.

In a process for producing ethanol from corn, following SSF or the RSH process, the liquid fermentation products are recovered from the fermented mash (often referred to as "beer mash"), e.g., by distillation, which separates the desired fermentation product, e.g. ethanol, from other liquids and/or solids. The remaining fraction is referred to as "whole stillage". Whole stillage typically contains about 10 to 20% solids. The whole stillage is separated into a solid and a liquid fraction, e.g., by centrifugation. The separated solid fraction is referred to as "wet cake" (or "wet grains") and the separated liquid fraction is referred to as "thin stillage". Wet cake and thin stillage contain about 35 and 7% solids, respectively. Wet cake, with optional additional dewatering, is used as a component in animal feed or is dried to provide "Distillers Dried Grains" (DDG) used as a component in animal feed. Thin stillage is typically evaporated to provide evaporator condensate and syrup or may alternatively be recycled to the slurry tank as "backset". Evaporator condensate may either be forwarded to a methanator before being discharged and/or may be recycled to the slurry tank as "cook water". The syrup may be blended into DDG or added to the wet cake before or during the drying process, which can comprise one or more dryers in sequence, to produce DDGS (Distillers Dried Grain with Solubles). Syrup typically contains about 25% to 35% solids. Oil can also be extracted from the thin stillage and/or syrup as a by-product for use in biodiesel production, as a feed or food additive or product, or other biorenewable products.

Distiller's grain with solubles (DGS) and distiller's dried grain with solubles (DDGS) are co-products of the grain to ethanol industry, which are used for animal feed. DGS and DDGS are rich in fiber, and therefore the highest feasible inclusion rate for monogastric animals, such as e.g. poultry and swine, is lower than for ruminants such as e.g. cattle. Glycohydrolase enzymes, such as e.g. endoxylanase, are added to feed blends to increase the digestibility of fiber rich feed blends. However, there are some challenges related to the action of enzymes added to feed blends; e.g. homogeneous mixing of the enzymes into the feed blend, heat stability of the enzyme protein during pelletization of the feed, stability of the enzyme protein during the low pH gastric passage, and relatively short residence time in the guts of some animal species.

SUMMARY OF THE INVENTION

The present invention overcomes the above challenges by adding a xylanase or an enzyme blend comprising a xylanase and/or cellulolytic composition upstream during the fermentation product production process, for example during the simultaneous saccharification and fermentation (SSF) step, where there is continuous mixing of a free flowing slurry, the temperature is stable (e.g., between 30 to 35° C.), the pH is stable (e.g., between about pH4 and pH5), and the residence time is typically in the range of 54 to 80 hours.

The present invention more particularly relates to the addition of xylanase or xylanase containing enzyme blends during the SSF process to produce a DDGS product, or DGS product, with higher digestibility for animals (e.g., monogastric animals). Without wishing to be bound by theory, it is believed that when the fiber (e.g., corn) is solubilized, entrapment of nutrients such as protein, oil, and residual starch, is reduced, thus making these nutrients more accessible, and the solubilized fiber may be fermented by the gut microbiome to metabolizable products such as fatty acids. Moreover, it is possible that the solubilized fiber has a positive effect on gut health by acting as a substrate for beneficial gut flora.

The present invention contemplates using xylanases alone, as well as in enzyme blends comprising xylanase and at least one addition enzyme, such as a cellulolytic composition, in saccharification, fermentation, or simultaneous saccharification and fermentation, to improve the quality of DDGS produced downstream in both conventional and raw-starch hydrolysis (RSH) ethanol production processes. In one aspect, the present invention relates to an enzyme blend comprising a xylanase. In an embodiment, the enzyme blend comprises a xylanase and at least one additional enzyme. In an embodiment, the enzyme blend further comprises a cellulolytic composition. In an embodiment, the cellulolytic composition is present in the blend the ratio of the xylanase and cellulolytic composition is from about 5:95 to about 95:5. In an embodiment, the ratio of the xylanase and the cellulolytic composition in the blend is about 10:90. In an embodiment, the ratio of the xylanase and the cellulolytic composition in the blend is about 20:80. In an embodiment, the ratio of the xylanase and the cellulolytic composition in the blend is about 50:50.

In an embodiment, the enzyme blend comprises at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95%, or at least 100% xylanase. In an embodiment, the enzyme blend comprises at least 5%, at least 10% xylanase, at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95% cellulolytic composition.

In an embodiment, the xylanase is a GH30 family xylanase. In an embodiment, the xylanase is a GH30 subfamily 8 xylanase ("GH30_8 xylanase"). In an embodiment, the xylanase is a GH30_8 xylanase selected from the group consisting of: (i) the *Bacillus subtilis* xylanase of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (ii) the *Bacillus subtilis* xylanase of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iii) the *Bacillus subtilis* xylanase of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iv) the *Bacillus amyloliquefaciens* xylanase of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (v) the *Bacillus amyloliquefaciens* xylanase of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (vi) the *Bacillus licheniformis* xylanase of SEQ ID NO: 6 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; and (vii) the *Paenibacillus pabuli* xylanase of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In an embodiment, the cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity.

In an embodiment, the cellulolytic composition comprises at least one, at least two, or at least three enzymes selected from the group consisting of: (i) a cellobiohydrolase I; (ii) a beta-glucosidase; and (iii) and endoglucanase.

In an embodiment, the cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In an embodiment, the cellulolytic composition comprises at least one, at least two, or at least three enzymes selected from the group consisting of: (i) an *Aspergillus fumigatus* cellobiohydrolase I; (ii) an *Aspergillus fumigatus* beta-glucosidase; and (iii) and a *Trichoderma reesei* endoglucanase.

In an embodiment, the cellulolytic composition comprises: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and/or (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the cellulolytic composition comprises: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and optionally (iii) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the cellulolytic composition further comprises an endoglucanase.

In an embodiment, the cellulolytic composition is derived from a strain selected from the group consisting of *Aspergillus, Penicilium, Talaromyces*, and *Trichoderma*, optionally wherein: (i) the *Aspergillus* strain is selected from the group consisting of *Aspergillus aurantiacus, Aspergillus niger* and *Aspergillus oryzae*; (ii) the *Penicilium* strain is selected from the group consisting of *Penicilium emersonii* and *Penicilium oxalicum*; (iii) the *Talaromyces* strain is selected from the group consisting of *Talaromyces aurantiacus* and *Talaromyces emersonii*; and (iv) the *Trichoderma* strain is *Trichoderma reesei*. In an embodiment, the cellulolytic composition comprises a *Trichoderma reesei* cellulolytic composition.

In another aspect, the present invention relates to a process of producing a fermentation product, comprising the following steps: (a) saccharifying a starch-containing material at a temperature below the initial gelatinization temperature with an alpha-amylase, a glucoamylase, and a xylanase or an enzyme blend comprising a xylanase of the present invention; (b) fermenting using a fermentation organism; and (c) optionally recovering a cooproduct.

In another aspect, the present invention relates to a process for producing a fermentation product from starch-containing material comprising the steps of: (a) liquefying a starch-containing material with an alpha-amylase; (b) saccharifying the liquefied material obtained in step (a) with a glucoamylase and a xylanase or an enzyme blend comprising a xylanase of the present invention; (c) fermenting using a fermenting organism; and (d) optionally recovering a co-product.

In an embodiment, saccharification and fermentation is performed simultaneously. In an embodiment, the starch-containing material comprises maize, corn, wheat, rye, barley, triticale, sorghum, switchgrass, millet, pearl millet, foxtail millet. In an embodiment, the fermentation product is alcohol, particularly ethanol. In an embodiment, the fermenting organism is yeast, particularly *Saccharomyces* sp., more particularly *Saccharomyces cerevisiae*.

In another aspect, the present invention relates to a process for improving the nutritional quality of distillers dried grains (DGS) or distillers dried grains with solubles (DDGS) produced as a co-product of a fermentation product production process, the process comprising performing a process for producing a fermentation product of the present invention, and recovering the fermentation product to produce DGS or DDGS as a co-product, wherein the DGS or DDGS produced have improved nutritional quality.

In an aspect, the present invention relates to DGS or DDGS produced using a process described herein, wherein the DGS/DDGS have improved nutritional quality as compared to the nutritional quality of DGS or DDGS produced using conventional processes.

In an embodiment, the true metabolizable energy of the DGS or DDGS is increased by at least 5%, at least 10%, at least 15%, or at least 20%, as compared to the TME of DGS or DDGS produced when an enzyme blend of the present invention is not present during the saccharification step, fermentation step, and/or simultaneous saccharification and fermentation step of a process for producing a fermentation product of the present invention.

In an embodiment, the animal is a monogastric animal.

In an embodiment, the DGS or DDGS produced are not darkened after drying as compared to DGS or DDGS produced when an enzyme blend of the present invention is not present during the saccharification step, fermentation step, and/or simultaneous saccharification and fermentation step of a process of the present invention.

In another aspect, the present invention relates to the use of a xylanase or an enzyme blend comprising a xylanase of the present invention for improving the nutritional quality of DGS or DDGS produced as a co-product of a fermentation product production process, preferably without resulting in a darkening the DDG or DDGS.

In another aspect, the present invention relates to the use of a xylanase or an enzyme blend of the present invention for solubilizing fiber, preferably for solubilizing xylose and arabinose.

OVERVIEW OF SEQUENCE LISTING

Figure 1:
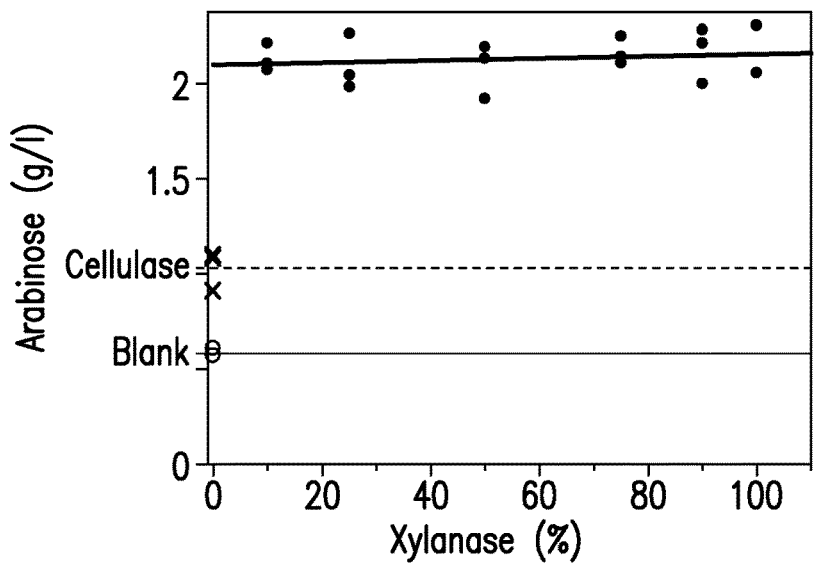
FIG. 1 shows solubilization of arabinose using enzyme blends of the present invention comprising different ratios of xylanase and a cellulolytic composition, and in particular shows significantly increased solubilization of arabinose when 10-100% of the cellulolytic composition in the enzyme blend is replaced by the xylanase as compared to solubilization of arabinose by the cellulolytic composition alone.

SEQ ID NO: 1 is the amino acid sequence of a mature GH30_8 xylanase from *Bacillus subtilis*.

SEQ ID NO: 2 is the amino acid sequence of a mature GH30 xylanase from *Bacillus subtilis*.

SEQ ID NO: 3 is the amino acid sequence of the mature GH30 xylanase from *Bacillus subtilis*.

SEQ ID NO: 4 is the amino acid sequence of the mature GH30 xylanase from *Bacillus amyloliquefaciens*.

SEQ ID NO: 5 is the amino acid sequence of the mature GH30 xylanase from *Bacillus amyloliquefaciens* HB-26.

SEQ ID NO: 6 is the amino acid sequence of the mature GH30 xylanase from *Bacillus licheniformis*.

SEQ ID NO: 7 is the amino acid sequence of the mature GH30 xylanase from *Paenibacillus pabuli*.

SEQ ID NO: 8 is the amino acid sequence of the full-length cellobiohydrolase I from *Aspergillus fumigatus*.

SEQ ID NO: 9 is the amino acid sequence of the full-length cellobiohydrolase II from *Aspergillus fumigatus*.

SEQ ID NO: 10 is the amino acid sequence of the full-length beta-glucosidase from *Aspergillus fumigatus*.

SEQ ID NO: 11 is the amino acid sequence of the full-length GH61 polypeptide from *Penicillium emersonii*.

SEQ ID NO: 12 is the amino acid sequence of the full-length alpha-amylase from *Bacillus stearothermophilus*.

SEQ ID NO: 13 is the amino acid sequence of the full-length GH10 xylanase from *Dictyogllomus thermophilum*.

SEQ ID NO: 14 is the amino acid sequence of the full-length GH11 xylanase from *Dictyogllomus thermophilum*.

SEQ ID NO: 15 is the amino acid sequence of the full-length GH10 xylanase from *Rasomsonia byssochlamydoides*.

SEQ ID NO: 16 is the amino acid sequence of the full-length GH10 xylanase from *Talaromyces leycettanus*.

SEQ ID NO: 17 is the amino acid sequence of the full-length GH10 xylanase from *Aspergillus fumigatus*.

SEQ ID NO: 18 is the amino acid sequence of the full-length endoglucanase from *Talaromyces leycettanus*.

SEQ ID NO: 19 is the amino acid sequence of the full-length endoglucanase from *Penicillium capsulatum*.

SEQ ID NO: 20 is the amino acid sequence of the full-length endoglucanase from *Trichophaea saccata*.

SEQ ID NO: 21 is the amino acid sequence of the full-length GH45 endoglucanase from *Sordaria fimicola*.

SEQ ID NO: 22 is the amino acid sequence of the full-length GH45 endoglucanase from *Thielavia terrestris*.

SEQ ID NO: 23 is the amino acid sequence of the full-length glucoamylase from *Penicillium oxalicum*.

SEQ ID NO: 24 is the amino acid sequence of the full-length protease from *Pyrococcus furiosus*.

SEQ ID NO: 25 is the amino acid sequence of the full-length protease from *Thermoascus aurantiacus*.

SEQ ID NO: 26 is the amino acid sequence of the *Rhizomucor pusillus* alpha-amylase with *Aspergillus niger* glucoamylase linker and starch binding domain (SBD) having the following substitutions G128D+D143N.

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-Amylases (alpha-1,4-glucan-4-glucanohydrolases, EC 3.2.1.1) are a group of enzymes, which catalyze the hydrolysis of starch and other linear and branched 1,4-glucosidic oligo- and polysaccharides.

Animal: The term "animal" refers to all animals except humans. Examples of animals are non-ruminants, and ruminants. Ruminant animals include, for example, animals such as sheep, goats, cattle, e.g., beef cattle, cows, and young calves, deer, yank, camel, llama and kangaroo. Non-ruminant animals include mono-gastric animals, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose.

For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42:55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Body Weight Gain: The term "body weight gain" means an increase in live weight of an animal during a given period of time, e.g., the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15:160-167; Teeri et al., 1998, *Trichoderma reesei* cellobiohydrolases: why so efficient on crystalline cellulose?, *Biochem. Soc. Trans.* 26:173-178).

Cellobiohydrolase activity is determined according to the procedures described by Lever et al., 1972, *Anal. Biochem.* 47:273-279; van Tilbeurgh et al., 1982, *FEBS Letters,* 149: 152-156; van Tilbeurgh and Claeyssens, 1985, *FEBS Letters,* 187:283-288; and Tomme et al., 1988, *Eur. J. Biochem.* 170:575-581. In the present invention, the Tomme et al. method can be used to determine cellobiohydrolase activity.

Cellulolytic enzyme, cellulolytic composition, or cellulase: The term "cellulolytic enzyme", "cellulolytic composition", or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, Biotechnology Advances 24:452-481. Total cellulolytic activity is usually measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (Ghose, 1987, Measurement of cellulase activities, *Pure Appl. Chem.* 59:257-68).

Cellulolytic enzyme activity is determined by measuring the increase in hydrolysis of a cellulosic material by cellulolytic enzyme(s) under the following conditions: 1-50 mg of cellulolytic enzyme protein/g of cellulose in Pretreated Corn Stover ("PCS") (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratorics, Inc., Hercules, CA, USA).

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components.

Endoglucanase activity can be determined by measuring reduction in substrate viscosity or increase in reducing ends determined by a reducing sugar assay (Zhang et al., 2006, Biotechnology Advances 24:452-481). For purposes of the present invention, endoglucanase activity is determined using carboxymethyl cellulose (CMC) as substrate according to the procedure of Ghose, 1987, *Pure and Appl. Chem.* 59:257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, Biochem. J. 280:309-316, and Henrissat B., and Bairoch A., 1996, Updating the sequence-based classification of glycosyl hydrolases, Biochem. J. 316:695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

Glucoamylases (glucan 1,4-alpha-glucosidase, EC 3.2.1.3) are a group of enzymes, which catalyze the hydrolysis of terminal (1→4)-linked α-D-glucose residues successively from non-reducing ends of the chains with release of beta-D-glucose.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases, Current Opinion In Microbiology 6 (3): 219-228. Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). An informative and updated classification of these and other carbohydrate active enzymes is available on the Carbohydrate-Active Enzymes (CAZy) database. Hemicellulolytic enzyme activities can be measured according to Ghose and Bisaria, 1987, Pure & Appl. Chern. 59:1739-1752, at a suitable temperature, e.g., 50° C., 55° C., or 60° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide of an A. fumigatus cellobiohydrolase I is amino acids 27 to 532 of SEQ ID NO: 8 based on the SignalP program (Nielsen et al., 1997, Protein Engineering 10:1-6) that predicts amino acids 1 to 26 of SEQ ID NO: 8 are a signal peptide. In another aspect, the mature polypeptide of an A. fumigates cellobiohydrolase II is amino acids 20 to 454 of SEQ ID NO: 9 based on the SignalP program that predicts amino acids 1 to 19 of SEQ ID NO: 9 are a signal peptide. In another aspect, the mature polypeptide of an A. fumigatus beta-glucosidase is amino acids 20 to 863 of SEQ ID NO: 10 based on the SignalP program that predicts amino acids 1 to 19 of SEQ ID NO: 10 are a signal peptide. In another aspect, the mature polypeptide of a Penicillium sp. GH61 polypeptide is amino acids 26 to 253 of SEQ ID NO: 11 based on the SignalP program that predicts amino acids 1 to 25 of SEQ ID NO: 11 are a signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nutrient Digestibility: The term "nutrient digestibility" means the fraction of a nutrient that disappears from the gastro-intestinal tract or a specified segment of the gastro-intestinal tract, e.g., the small intestine. Nutrient digestibility may be measured as the difference between what is administered to the subject and what. comes out in the faeces of the subject, or between what is administered to the subject and what remains in the digesta on a specified segment of the gastro intestinal tract, e.g., the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digest a on a specified segment of the gastro-intestinal tract of the animal, e.g., the ilcum.

Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digest a present in specified segment of the gastro-intestinal tract using the same methods to measure the digestibility of nutrients, with appropriate corrections for nitrogen excretion to calculate metabolizable energy of feed.

Operably linked: The term "operably linked" means a configuration in which a control sequence is placed at an appropriate position relative to the coding sequence of a polynucleotide such that the control sequence directs expression of the coding sequence.

Percentage solubilized xylan: The term "percentage solubilized xylan" means the amount of xylose measured in the supernatant after incubation with an enzyme compared to the total amount of xylose present in the substrate before the incubation with the enzyme. For the purpose of the present invention, the percentage solubilized xylan may be calculated using defatted destarched maize (DFDSM) as substrate. DFDSM is prepared according to 'Preparation of Defatted Destarched Maize (DFDSM)' in the experimental section.

The percentage solubilized xylan from defatted destarched maize (DFDSM) may be determined using the reaction conditions 20 µg enzyme/g DFDSM and incubation at 40° C., pH 5 for 2.5 hours as described in the 'Xylose solubilization assay' herein. Thus the term 'is performed under the reaction conditions 20 µg xylanase variant per gram defatted destarched maize (DFDSM) and incubation at 40° C., pH 5 for 2.5 hours' is to be understood that the percentage solubilised xylan is calculated as described in the 'Xylose solubilization assay' herein.

In a more detailed embodiment, 2% (w/w) DFDSM suspension was prepared in 100 mM sodium acetate, 5 mM $CaCl_2$), pH 5 and allowed to hydrate for 30 min at room temperature under gently stirring. After hydration, 200 µl substrate suspension was pipetted into a 96 well plate and mixed with 20 µl enzyme solution to obtain a final enzyme concentration of 20 PPM relative to substrate (20 µg enzyme/g substrate). The enzyme/substrate mixtures were left for hydrolysis in 2.5 h at 40° C. under gently agitation (500 RPM) in a plate incubator. After enzymatic hydrolysis, the enzyme/substrate plates were centrifuged for 10 min at 3000 RPM and 50 µl supernatant was mixed with 100 µl 1.6 M HCl and transferred to 300 µl PCR tubes and left for acid hydrolysis for 40 min at 90° C. in a PCR machine. Samples were neutralized with 125 µl 1.4 M NaOH after acid hydrolysis and loaded on the HPAE-PAD for mono-saccharide analysis.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptide having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), e.g., version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the nobrief option) is used as the percent identity and is calculated as follows:

(Identical Residues×100)/(Length of Alignment-Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), e.g., version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment-Total Number of Gaps in Alignment)

Variant: The term "variant" means a polypeptide having enzyme or enzyme enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Wild-type xylanase: The term "wild-type" xylanase means a xylanase expressed by a naturally occurring microorganism, such as a bacterium, yeast, or filamentous fungus found in nature.

Xylanase: The term "xylanase" means a glucuronoarabinoxylan endo-1,4-beta-xylanase (E.C. 3.2.1.136) that catalyses the endohydrolysis of 1,4-beta-D-xylosyl links in some glucuronoarabinoxylans. Xylanase activity can be determined with 0.2% AZCL-glucuronoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-glucuronoxylan as substrate in 200 mM sodium phosphate pH 6.

Conventions for Designation of Variants

For purposes of the present invention, SEQ ID NO: 1 is used to determine the corresponding amino acid residue in another xylanase. The amino acid sequence of another xylanase is aligned with SEQ ID NO: 1, and based on the alignment, the amino acid position number corresponding to any amino acid residue in SEQ ID NO: 1 is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), e.g., version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another xylanase can be determined by an alignment of multiple polypeptide sequences using several computer programs including, but not limited to, MUSCLE (multiple sequence comparison by log-expectation; version 3.5 or later; Edgar, 2004, Nucleic Acids Research 32:1792-1794), MAFFT (version 6.857 or later; Katoh and Kuma, 2002, Nucleic Acids Research 30:3059-3066; Katoh et al., 2005, Nucleic Acids Research 33:511-518; Katoh and Toh, 2007, Bioinformatics 23:372-374; Katoh et al., 2009, Methods in Molecular Biology 537:39-64; Katoh and Toh, 2010, Bioinformatics 26:1899-1900), and EMBOSS EMMA employing ClustalW (1.83 or later; Thompson et al., 1994, Nucleic Acids Research 22:4673-4680), using their respective default parameters.

When the other enzyme has diverged from the polypeptide of SEQ ID NO: 1 such that traditional sequence-based comparison fails to detect their relationship (Lindahl and Elofsson, 2000, J. Mol. Biol. 295:613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25:3389-3402). Even greater sensitivity can be achieved if the family or superfamily for the polypeptide has one or more representatives in the protein structure databases. Programs such as GenTHREADER (Jones, 1999, J. Mol. Biol. 287:797-815; McGuffin and Jones, 2003, Bioinformatics 19:874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313:903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33:88-96) or combinatorial extension (Shindyalov and Bourne, 1998, Protein Engineering 11:739-747), and implementation of these algorithms can additionally be utilized to query structure databases with a structure of interest in order to discover possible structural homologs (e.g., Holm and Park, 2000, Bioinformatics 16:566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine(S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple alterations. Variants comprising multiple alterations are separated by a plus sign ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DESCRIPTION OF THE INVENTION

The present invention relates to a process for improving the nutritional quality of distillers dried grains (DDG) or distillers dried grains with solubles (DDGS) produced as a co-product of a fermentation product production process, processes for producing fermentation products, as well as enzyme blends used in the processes.

DDGS is typically fed to cattle because the high fiber content limits the nutritional value for monogastric animals (e.g., poultry and swine). Thus, there is a need for a solution that specifically improves the nutritional value of DDGS for monogastric animals. By solubilizing part of the fiber, the nutritional value for monogastric animals can be increased. One way to solubilize fiber is by adding enzymes to the feed blend, however, the shorter residence time and less than ideal conditions in vivo limits the efficacy of enzymes added to feed.

The work described herein demonstrates that the addition of a presently disclosed xylanase or enzyme blend comprising xylanase upstream during the fermentation product production process (e.g., during simultaneous saccharification and fermentation) significantly increases the degree of fiber solubilization. Unexpectedly, as an added benefit, the presently disclosed xylanase or enzyme blend comprising xylanase significantly increase the degree of fiber solubilization without resulting in the darkening of DDGS during the drying process.

I. Enzyme Blends

The present invention contemplates using xylanases alone, as well as in enzyme blends comprising xylanase and at least one addition enzyme, such as a cellulolytic composition, in saccharification, fermentation, or simultaneous saccharification and fermentation, to improve the quality of DDGS produced downstream in both conventional and raw-starch hydrolysis (RSH) ethanol production processes. In an aspect, the present invention relates to xylanase or enzyme blends comprising a xylanase and/or a cellulolytic composition for solubilization of fiber (e.g., corn fiber, e.g., arabinose, xylose, etc.), for example, during the SSF step (or pre-saccharification step) of a fermentation product production process (e.g., ethanol), preferably without resulting in darkening of DDG or DDGS produced as a co-product of the fermentation product production process. When the cellulolytic composition is included in the blend, the ratio of the xylanase and the cellulolytic composition can be optimized to increase fiber solubilization of any particular substrate (e.g., corn fiber) and minimize or prevent darkening of downstream DDG or DDGS.

In one aspect the present invention relates to xylanase or an enzyme blend comprising a xylanase. In one aspect the present invention relates to xylanase or an enzyme blend comprising a xylanase and a cellulolytic composition, wherein the ratio of the xylanase and cellulolytic composition in the blend is from about 5:95 to about 95:5. In an embodiment, the ratio of the xylanase and cellulolytic composition is 10:90. In an embodiment, the ratio of the xylanase and cellulolytic composition is 15:85. In an embodiment, the ratio of the xylanase and cellulolytic composition is 20:80. In an embodiment, the ratio of the xylanase and cellulolytic composition is 25:75. In an embodiment, the ratio of the xylanase and cellulolytic composition is 30:70. In an embodiment, the ratio of the xylanase and cellulolytic composition is 35:65. In an embodiment, the ratio of the xylanase and cellulolytic composition is 40:60. In an embodiment, the ratio of the xylanase and cellulolytic composition is 45:55. In an embodiment, the ratio of the xylanase and cellulolytic composition is 50:50. In an embodiment, the ratio of the xylanase and cellulolytic composition is 55:45. In an embodiment, the ratio of the xylanase and cellulolytic composition is 60:40. In an embodiment, the ratio of the xylanase and cellulolytic composition is 65:35. In an embodiment, the ratio of the xylanase and cellulolytic composition is 70:30. In an embodiment, the ratio of the xylanase and cellulolytic composition is 75:25. In an embodiment, the ratio of the xylanase and cellulolytic composition is 80:20. In an embodiment, the ratio of the xylanase and cellulolytic composition is 85:15. In an embodiment, the ratio of the xylanase and cellulolytic composition is 90:10.

Xylanase

The present invention contemplates using any xylanase that, when optionally blended together with a cellulolytic composition in various ratios, is capable of solubilizing fiber (e.g., arabinose, xylose, etc.) in a fermentation product production process, such as especially ethanol, preferably without resulting in a darkening of the DDGS after drying.

In one embodiment, the xylanase is from the taxonomic order Bacillales, or preferably the taxonomic family Bacillaceae or Paenibacillaceae, or more preferably from the taxonomic genus *Bacillus* or *Paenibacillus*, or even more preferably from the taxonomic species *Bacillus subtilis, Bacillus amyloliquefaciens, Bacillus licheniformis* or *Paenibacillus pabuli*. In one embodiment, the xylanase has at least 70%, e.g., at at least 75%, at least 80%, at least 85%, at least 90%, at least 95%, at least 96%, at least 97%, at least 98%, at least 99% or 100% sequence identity to SEQ ID NO: 1 or SEQ ID NO: 2 and is obtained or obtainable from the taxonomic order Bacillales, or preferably the taxonomic family Bacillaceae or Paenibacillaceae, or more preferably from the taxonomic genus *Bacillus* or *Paenibacillus*, or even more preferably from the taxonomic species *Bacillus subtilis, Bacillus amyloliquefaciens, Bacillus licheniformis* or *Paenibacillus pabuli*. In one embodiment, the xylanase is a GH30 subfamily 8 xylanase (herein referred to as GH30_8 xylanases).

The xylanase may be (a) a polypeptide having at least 70% sequence identity to SEQ ID NO: 1, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the xylanase differs by up to 10 amino acids, e.g., 1, 2, 3, 4, 5, 6, 7, 8, 9, or 10, from SEQ ID NO: 1. In one embodiment, the xylanase comprises or consists of the amino acid sequence of SEQ ID NO: 1, is a fragment of SEQ ID NO: 1 wherein the fragment has xylanase activity or comprises the amino acid sequence of SEQ ID NO: 1 and an N- and/or C-terminal extension of up to 10 amino acids, e.g. 1, 2, 3, 4, 5, 6, 7, 8, 9 or 10 amino acids.

The xylanase may be (a) a polypeptide having at least 70% sequence identity to SEQ ID NO: 2, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the xylanase differs by up to 10 amino acids, e.g., 1, 2, 3, 4, 5, 6, 7, 8, 9, or 10, from SEQ ID NO: 2. In one embodiment, the xylanase comprises or consists of the amino acid sequence of SEQ ID NO: 2, is a fragment of SEQ ID NO: 2 wherein the fragment has xylanase activity or comprises the amino acid sequence of SEQ ID NO: 2 and an N- and/or C-terminal extension of up to 10 amino acids, e.g. 1, 2, 3, 4, 5, 6, 7, 8, 9 or 10 amino acids.

The xylanase may be (a) a polypeptide having at least 70% sequence identity to SEQ ID NO: 3, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the xylanase differs by up to 10 amino acids, e.g., 1, 2, 3, 4, 5, 6, 7, 8, 9, or 10, from SEQ ID NO: 3. In one embodiment, the xylanase comprises or consists of the amino acid sequence of SEQ ID NO: 3, is a fragment of SEQ ID NO: 3 wherein the fragment has xylanase activity or comprises the amino acid sequence of SEQ ID NO: 3 and an N- and/or C-terminal extension of up to 10 amino acids, e.g. 1, 2, 3, 4, 5, 6, 7, 8, 9 or 10 amino acids.

The xylanase may be (a) a polypeptide having at least 70% sequence identity to SEQ ID NO: 4, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the xylanase differs by up to 10 amino acids, e.g., 1, 2, 3, 4, 5, 6, 7, 8, 9, or 10, from SEQ ID NO: 4. In one embodiment, the xylanase comprises or consists of the amino acid sequence of SEQ ID NO: 4, is a fragment of SEQ ID NO: 4 wherein the fragment has xylanase activity or comprises the amino acid sequence of SEQ ID NO: 4 and an N- and/or C-terminal extension of up to 10 amino acids, e.g. 1, 2, 3, 4, 5, 6, 7, 8, 9 or 10 amino acids.

The xylanase may be (a) a polypeptide having at least 70% sequence identity to SEQ ID NO: 5, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the xylanase differs by up to 10 amino acids, e.g., 1, 2, 3, 4, 5, 6, 7, 8, 9, or 10, from SEQ ID NO: 5. In one embodiment, the xylanase comprises or consists of the amino acid sequence of SEQ ID NO: 5, is a fragment of SEQ ID NO: 5 wherein the fragment has xylanase activity or comprises the amino acid sequence of SEQ ID NO: 5 and an N- and/or C-terminal extension of up to 10 amino acids, e.g. 1, 2, 3, 4, 5, 6, 7, 8, 9 or 10 amino acids.

The xylanase may be (a) a polypeptide having at least 70% sequence identity to SEQ ID NO: 6, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the xylanase differs by up to 10 amino acids, e.g., 1, 2, 3, 4, 5, 6, 7, 8, 9, or 10, from SEQ ID NO: 6. In one embodiment, the xylanase comprises or consists of the amino acid sequence of SEQ ID NO: 6, is a fragment of SEQ ID NO: 6 wherein the fragment has xylanase activity or comprises the amino acid sequence of SEQ ID NO: 6 and an N- and/or C-terminal extension of up to 10 amino acids, e.g. 1, 2, 3, 4, 5, 6, 7, 8, 9 or 10 amino acids.

The xylanase may be (a) a polypeptide having at least 70% sequence identity to SEQ ID NO: 7, e.g., at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the xylanase differs by up to 10 amino acids, e.g., 1, 2, 3, 4, 5, 6, 7, 8, 9, or 10, from SEQ ID NO: 7. In one embodiment, the xylanase comprises or consists of the amino acid sequence of SEQ ID NO: 7, is a fragment of SEQ ID NO: 7 wherein the fragment has xylanase activity or comprises the amino acid sequence of SEQ ID NO: 7 and an N- and/or C-terminal extension of up to 10 amino acids, e.g. 1, 2, 3, 4, 5, 6, 7, 8, 9 or 10 amino acids.

Other examples of suitable xylanases are the following GENESEQP accession numbers: BCM03690, BBY25441, BBD43833, AZG87760, BBW75090, BCM03682, BBW96675, BCM03671, ADJ35022, BBW83525, BCM03685, BBW88031, BCM03707, AZH70238, AZG87766, BBX36748, BCM03686, AZQ23477, BCM03677, BCM03691, BCM03681, BCM03676, BCM03688, AZG68558, ADJ35028, BCM03687, BBG80964, AZX66647, AZH70244, BCM03689, AZM95903, BBW79314, BBX47049, BCM03683, BCM03679, BBW95840, BBX52401, BBW92246, BBX42063 and AZG68552.

Other examples of suitable xylanases are following Uniprot accession numbers: A0A016QIT0, A0A024BEN2, A0A059N8P2, A0A060J1Q4, A0A060J3N3, A0A060MDP8, A0A063XEB2, A0A063Z3F5, A0A066ZQH2, A0A068QG80, A0A069DJA1, A0A074QA16, A0A076GH62, A0A076X095, A0A080UGI0, A0A081DRH7, A0A081L9P3, A0A085CCQ4, A0A086DRT4, A0A086SGC4, A0A086WWT9, A0A089J0T9, A0A089L7Q4, A0A089LS30, A0A089MA96, A0A089MMY5, A0A090ZY18, A0A093UG96, A0A097RET6, A0A097RT57, A0A0A0TJX0, A0A0A0TS05, A0A0A1STB1, A0A0A7GLZ8, A0A0A8C3V5, A0A0B0QGI0, A0A0B4S841, A0A0C2TMZ1, A0A0C5CYD2, A0A0D7XHL0, A0A0D7XPV8, A0A0D8JJW7, A0A0E1LNG3, A0A0E1P2T5, A0A0F5MCQ0, A0A0F5YUV2, A0A0G2M1V3, A0A0G2Z099, A0A0G3VDP8, A0A0H1RW51, A0A0H3DZC9, A0A0J1HNE5, A0A0J1I8S6, A0A0J5XBB3, A0A0J6E3H1, A0A0J6ENY2, A0A0J6MZ81, A0A0J6PTT5, A0A0K0HYL4, A0A0K6JZ62, A0A0K6L1ES, A0A0K6L5C0, A0A0K6LRC5, A0A0K6MBZ9, A0A0K9EI79, A0A0K9G2M8, A0A0L6C9N3, A0A0L7MT05, A0A0L7SGL4, A0A0M0HBT0, A0A0M2EI36, A0A0M2S6E2, A0A0M9X369, A0A0P0TKN9, A0A0P7GC51, A0A0Q3W7T1, A0A0Q4R817, A0A0Q7SDS0, A0A0R3K873, A0A0T6LD54, A0A0U3M226, A0A0USQ000, A0A0V8QN06, A0A0V8QPQ0, A0A0V8RCK0, A0A0W1Q0Y8, A0A0W7XI48, A0A0W8K830, A0A0X1TCR2, A0A0X8C7K8, A0A0X8DHN5, A0A0X8KDH2, A0A101YC92, A0A101YL97, A0A117SZP6, A0A124JQM2, A0A125UIF6, A0A127DQZ4, A0A132BP80, A0A132TGU4, A0A132TSQ5, A0A136AEB9, A0A142F586, A0A150L2Y6, A0A160EHD0, A0A164XMN2, A0A172HNWI, A0A172XIR5, A0A199NI63, A0A199WHT5, A0AIA0CC44, A0A1A0G7Q3, A0ALASVV23, A0A1ASYLD9, A0A1A7LKF3, A0A1B2AW76, A0A1C3S1T4, A0A1C4AHG6, A0A1D9PK78, A0A1E4Y0F1, A0A1G9MAD1, A0A1J0BBP6, A0A1J0C717, A0A1JSWRC5, A0A1J6F1D5, A0A1K1TBA7, A0A1L3PT45, A0A1L3QY16, A0A1L3SH52, A0A1L4DM20, A0A1L5LNU4, A0A1L6CEM3, A0A1L6ZLN8, A0A1L6ZTD9, A0A1M7SMM4, A0A1N6S500, A0A1N7B930, A0A1N7E7E0, A0A1R1E8G3, A0A1R1ESJ7, A0A1R1FQ77, A0A1R1GBK8, A0A1R1GT02, A0A1R1HH77, A0A1S2F2R2, A0A1U3ULV5, A7Z5A1, A8FDV2, B3KF38, D1MEP8, D3EH02, D4FXC2, E0RDU2, E1ACF9, E1UV03, E3E322, E8VJ45, F4E4B0, F4EKU6, G01KW9, G4EVQ6, G4HGL4, G4P7F1, G7W2J1, H0FNN1, H1ACZ7, H2AJ54, H3K352, H6CPJ0, H6WCZ0, H8XMR3, I4XB64, J0X3V6, J7JVZ4, K2HJT3, K2P3H7, L0BLZ3, L0CY72, L8AKB2, M1KJT1, M1U2J5, M1XAU4, M2U9N8, N0DF18, Q45070, Q6YK37, Q70K02, R9TYN3, S6FS40, S6FXS9, U1T362, U1ZC44, U2TM90, U4PL99, U5X5B8, V5MRU9, V7Q6M1, V9REY3, W4AZH7, W4BX14, W4C6X9, W4D801, W4DEL3, W81LG7 and W9TFT6.

In an embodiment, the xylanase comprises a variant xylanase having one or more substitutions described in EP Application Serial No. 17177304.7 (incorporated herein by reference in its entirety).

In an embodiment, the xylanase comprises a variant xylanase having one or more substitutions described in International Patent Application No. PCT/EP2017/065336 (incorporated herein by reference in its entirety).

The polypeptide may be a hybrid polypeptide in which a region of one polypeptide is fused at the N-terminus or the C-terminus of a region of another polypeptide.

The xylanase may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12:2575-2583; Dawson et al., 1994, *Science* 266:776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3:568-576; Svetina et al., 2000, *J. Biotechnol.* 76:245-251; Rasmussen-Wilson et al., 1997, *Appl. Environ. Microbiol.* 63:3488-3493; Ward et al., 1995, *Biotechnology* 13:498-503; and Contreras et al., 1991, *Biotechnology* 9:378-381; Eaton et al., 1986, *Biochemistry* 25:505-512; Collins-Racie et al., 1995, *Biotechnology* 13:982-987; Carter et al., 1989, *Proteins: Structure, Function, and Genetics* 6:240-248; and Stevens, 2003, *Drug Discovery World* 4:35-48.

The xylanase may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The polypeptide may be a bacterial polypeptide. For example, the polypeptide may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* polypeptide having xylanase activity. In one embodiment, the polypeptide is from a bacterium of the class Bacilli, such as from the order Bacillales, or preferably the taxonomic family Bacillaceae or Paenibacillaceae, or more preferably from the taxonomic genus *Bacillus* or *Paenibacillus,* or even more preferably from the taxonomic species *Bacillus subtilis, Bacillus amyloliquefaciens, Bacillus licheniformis* or *Paenibacillus pabuli.*

In one aspect, the xylanase is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* xylanase.

In a preferred aspect, the xylanase is a *Bacillus subtilis* xylanase, e.g., the xylanase having the amino acid sequence of SEQ ID NO: 1.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The xylanase may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra). In an embodiment, the xylanase is a *Bacillus* GH30_8 xylanase. Exemplary GH30_8 xylanases of use in the enzyme blends and processes of the present invention include those from the taxonomic genera of *Bacteroides, Cellvibrio, Clostridium, Cystobacter, Bacillus, Dickeya, Fibrobacter, Geobacillus, Meloidogyne, Micromonospora, Mucilaginibacter, Paenibacillus, Paludibacter, Radopholus, Ruminococcus, Serratia, Streptomyces, Verrucosispora,* and *Xanthomonas.*

In an embodiment, the xylanase is a GH30_8 xylanase selected from the group consisting of: (i) the *Bacillus subtilis* xylanase of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (ii) the *Bacillus subtilis* xylanase of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iii) the *Bacillus subtilis* xylanase of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iv) the *Bacillus amyloliquefaciens* xylanase of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (v) the *Bacillus amyloliquefaciens* xylanase of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto;
(vi) the *Bacillus licheniformis* xylanase of SEQ ID NO: 6 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; and (vii) the *Paenibacillus pabuli* xylanase of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Clostridium*, for example: (i) a *Clostridium acetobutylicum* xylanase, such as the one disclosed as SEQ ID NO: 1 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto, or the one disclosed as SEQ ID NO: 36 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto, or the one disclosed as SEQ ID NO: 37 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (ii) a *Clostridium papyrosolvens* xylanase, such as the one disclosed as SEQ ID NO: 2 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto, or the one disclosed as SEQ ID NO: 17 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iii) a *Clostridium thermocellum* xylanase, such as the one disclosed as SEQ ID NO: 10 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iv) a *Clostridium saccharoperbutylacetonicum*, such as the one disclosed as SEQ ID NO: 11 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto, or the one disclosed as SEQ ID NO: 15 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto, or the one disclosed as SEQ ID NO: 35 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; or (v) a *Clostridium* sp. DL-VIII xylanase, such as the one disclosed as SEQ ID NO: 10 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Bacteroides*, such as a *Bacteroides clarus* xylanase, such as the one disclosed as SEQ ID NO:

29 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Cellvibrio, such as a Cellvibrio japonicas xylanase, such as the one disclosed as SEQ ID NO: 9 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Cystobacter, such as a Cystobacter fuscus xylanase, such as the one disclosed as SEQ ID NO: 7 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Bacillus, for example: (i) a Bacillus amyloliquefaciens xylanase, such as the one disclosed as SEQ ID NO: 25 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (ii) a Bacillus atrophaeus xylanase, such as the one disclosed as SEQ ID NO: 20 in U'S2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iii) a Bacillus licheniformis xylanase, such as the one disclosed as SEQ ID NO: 24 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (iv) a Bacillus pumilus, such as the one disclosed as SEQ ID NO: 22 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto, or the one disclosed as SEQ ID NO: 23 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (v) a Bacillus stratosphericus xylanase, such as the one disclosed as SEQ ID NO: 21 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; (vi) a Bacillus subtilis xylanase, such as the one disclosed as SEQ ID NO: 5 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; or (vii) a Bacillus xiamenensis xylanase, such as the one disclosed as SEQ ID NO: 19 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Dickeya, such as a Dickeya chrysanthemi xylanase, such as the one disclosed as SEQ ID NO: 31 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Fibrobacter, such as a Fibrobacter succinogenes xylanase, such as the one disclosed as SEQ ID NO: 26 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Geobacillus, such as a Geobacillus sp. xylanase, such as the one disclosed as SEQ ID NO: 16 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Meloidogyne, such as a Meloidogyne incognita xylanase, such as the one disclosed as SEQ ID NO: 32 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Micromonospora, such as (i) a Micromonospora lupini str. xylanase, such as the one disclosed as SEQ ID NO: 18 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; or (ii) a Micromonospora sp. xylanase, such as such as the one disclosed as SEQ ID NO: 28 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Mucilaginibacter, such as a Mucilaginibacter paludis xylanase, such as the one disclosed as SEQ ID NO: 4 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto, or the one disclosed as SEQ ID NO: 30 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus Paenibacillus, such as a Paenibacillus sp. xylanase, such as the one disclosed as SEQ ID NO: 13 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Paludibacter*, such as a *Paludibacter propionicigenes* xylanase, such as the one disclosed as SEQ ID NO: 3 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Radopholus*, such as a *Radopholus similis* xylanase, such as the one disclosed as SEQ ID NO: 33 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Ruminococcus*, such as a *Ruminococcus* sp. xylanase, such as the one disclosed as SEQ ID NO: 12 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Serratia*, such as a *Serratia* sp. E-15 xylanase, such as the one disclosed as SEQ ID NO: 6 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Streptomyces*, such as a *Streptomyces bingchenggensis* xylanase, such as the one disclosed as SEQ ID NO: 14 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Verrucosispora*, such as a *Verrucosispora marie* xylanase, such as the one disclosed as SEQ ID NO: 27 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In one embodiment, the xylanase is a GH30_8 xylanase from a strain of the genus *Xanthomonas*, such as a *Xanthomonas campestris* xylanase, such as the one disclosed as SEQ ID NO: 8 in US2016/040203, or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

In an embodiment, the xylanase is not a GH10 xylanase. In an embodiment, the xylanase is not a GH11 xylanase.

In an embodiment, the xylanase, e.g., GH30 xylanase, such as especially GH30_8 xylanase, for example of SEQ NOs: 1-7, or variants thereof, is dosed in pre-saccharification, saccharification, and/or simultaneous saccharification and fermentation in a concentration of between 0.0001-1 mg EP (Enzyme Protein)/g DS, e.g., 0.0005-0.5 mg EP/g DS, such as 0.001-0.1 mg EP/g DS.

Cellulolytic Composition

The present invention contemplates using any cellulolytic composition that, when blended with a xylanase in various ratios, is capable of solubilizing fiber (e.g., arabinose, xylose, etc.) in a fermentation product production process, such as especially ethanol, without resulting in a darkening of the DDGS after drying. The cellulolytic composition used in an enzyme blend or process of the invention for producing fermentation products may be derived from any microorganism. As used herein, "derived from any microorganism" means that the cellulolytic composition comprises one or more enzymes that were expressed in the microorganism. For instance, a cellulolytic composition derived from a strain of *Trichoderma reesei* means that the cellulolytic composition comprises one or more enzymes that were expressed in *Trichoderma reesei*.

In an embodiment, the cellulolytic composition is derived from a strain of *Aspergillus*, such as a strain of *Aspergillus aurantiacus, Aspergillus niger* or *Aspergillus oryzae*.

In an embodiment, the cellulolytic composition is derived from a strain of *Chrysosporium*, such as a strain of *Chrysosporium lucknowense*.

In an embodiment, the cellulolytic composition is derived from a strain of *Humicola*, such as a strain of *Humicola insolens*.

In an embodiment, the cellulolytic composition is derived from a strain of *Penicilium*, such as a strain of *Penicilium emersonii* or *Penicilium oxalicum*.

In an embodiment, the cellulolytic composition is derived from a strain of *Talaromyces*, such as a strain of *Talaromyces aurantiacus* or *Talaromyces emersonii*.

In an embodiment, the cellulolytic composition is derived from a strain of *Trichoderma*, such as a strain of *Trichoderma reesei*.

In a preferred embodiment, the cellulolytic composition is derived from a strain of *Trichoderma reesei*. In a preferred embodiment, the *Trichoderma reesei* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Trichoderma reesei* cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In another preferred embodiment, the *Trichoderma reesei* cellulolytic composition comprises at least one, at least two, or at least three enzymes selected from the group consisting of: (i) a cellobiohydrolase I; (ii) a beta-glucosidase; and (iii) an endoglucanase. In another preferred embodiment, the *Trichoderma reesei* cellulolytic composition comprises at least one, at least two, or at least three enzymes selected from the group consisting of: (i) an *Aspergillus fumigatus* cellobiohydrolase I; (ii) an *Aspergillus fumigatus* beta-glucosidase; and (iii) a *Trichoderma reesei* endoglucanase.

In yet another preferred embodiment, the *Trichoderma reesei* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Trichoderma reesei* cellulolytic composition further comprises an endoglucanase.

In a preferred embodiment, the cellulolytic composition is derived from a strain of *Aspergillus aurantiacus*. In a preferred embodiment, the *Aspergillus aurantiacus* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Aspergillus aurantiacus* cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In yet another preferred embodiment, the *Aspergillus aurantiacus* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Aspergillus aurantiacus* cellulolytic composition further comprises an endoglucanase.

In a preferred embodiment, the cellulolytic composition is derived from a strain of *Aspergillus niger*. In a preferred embodiment, the *Aspergillus niger* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Aspergillus niger* cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In yet another preferred embodiment, the *Aspergillus niger* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Aspergillus niger* cellulolytic composition further comprises an endoglucanase.

In a preferred embodiment, the cellulolytic composition is derived from a strain of *Aspergillus oryzae*. In a preferred embodiment, the *Aspergillus oryzae* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Aspergillus oryzae* cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In yet another preferred embodiment, the *Aspergillus oryzae* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Aspergillus oryzae* cellulolytic composition further comprises an endoglucanase.

In a preferred embodiment, the cellulolytic composition is derived from a strain of *Penicilium emersonii*. In a preferred embodiment, the *Penicilium emersonii* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Penicilium emersonii* cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In yet another preferred embodiment, the *Penicilium emersonii* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Penicilium emersonii* cellulolytic composition further comprises an endoglucanase.

In a preferred embodiment, the cellulolytic composition is derived from a strain of *Penicilium oxalicum*. In a preferred embodiment, the *Penicilium oxalicum* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Penicilium oxalicum* cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In yet another preferred embodiment, the *Penicilium oxalicum* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Penicilium oxalicum* cellulolytic composition further comprises an endoglucanase.

In a preferred embodiment, the cellulolytic composition is derived from a strain of *Talaromyces aurantiacus*. In a preferred embodiment, the *Talaromyces aurantiacus* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Talaromyces aurantiacus* cellulolytic composition comprises at least one, at least two, at least three, or at least four enzymes selected from the group consisting of:

(i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In yet another preferred embodiment, the *Talaromyces aurantiacus* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Talaromyces aurantiacus* cellulolytic composition further comprises an endoglucanase.

In a preferred embodiment, the cellulolytic composition is derived from a strain of *Talaromyces emersonii*. In a preferred embodiment, the *Talaromyces emersonii* cellulolytic composition comprises at least one, at least two, at least three, or at least four enzymes selected from the group consisting of: (i) a cellobiohydrolase I; (ii) a cellobiohydrolase II; (iii) a beta-glucosidase; and (iv) a GH61 polypeptide having cellulolytic enhancing activity. In another preferred embodiment, the *Talaromyces emersonii* cellulolytic composition comprises at least one, at least two, at least three, or at least four enzymes selected from the group consisting of: (i) an *Aspergillus fumigatus* cellobiohydrolase I; (ii) an *Aspergillus fumigatus* cellobiohydrolase II; (iii) an *Aspergillus fumigatus* beta-glucosidase; and (iv) a *Penicillium emersonii* GH61A polypeptide having cellulolytic enhancing activity.

In yet another preferred embodiment, the *Talaromyces emersonii* cellulolytic composition comprises at least one, at least two, at least three, or at least four enzymes selected from the group consisting of: (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8; (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9; (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

In an embodiment, the *Talaromyces emersonii* cellulolytic composition further comprises an endoglucanase.

The cellulolytic composition may further comprise multiple enzymatic activities, such as one or more (e.g., several) enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, glucan 1,4-a-glucosidase, glucan 1,4-alpha-maltohydrolase, glucan 1,4-a-glucosidase, glucan 1,4-alpha-maltohydrolase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In an embodiment, the cellulolytic composition comprises one or more formulating agents as disclosed herein, preferably one or more of the compounds selected from the list consisting of glycerol, ethylene glycol, 1,2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment the cellulolytic composition, e.g., derived from a strain of *Aspergillus, Penicilium, Talaromyces*, or *Trichoderma*, such as a *Trichoderma reesei* cellulolytic composition, is dosed in pre-saccharification, saccharification, and/or simultaneous saccharification and fermentation in a concentration of 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

II. Processes for Producing Fermentation Products

The invention also relates to processes for producing a fermentation product from starch-containing material using a fermenting organism, wherein a xylanase or an enzyme blend comprising a xylanase and optionally a cellulolytic composition (e.g., derived from *Trichoderma reesei*) is added before and/or during fermentation. Those skilled in the art will appreciate that any of the xylanases or enzyme blends described in Section I above, or otherwise described herein, can be used in the processes of the invention, including the processes of Section II.

Processes for Producing Fermentation Products from Un-Gelatinized Starch-Containing Material In an aspect, the invention relates to processes for producing fermentation products from starch-containing material without gelatinization (i.e., without cooking) of the starch-containing material (often referred to as a "raw starch hydrolysis" process), wherein a presently disclosed xylanase or enzyme blend comprising a xylanase and a cellulolytic composition (e.g., derived from *Trichoderma reesei*) is added. The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a xylanase or an enzyme blend of the invention. Exemplary xylanases and enzyme blends of use in the processes are described in Section I above entitled "Enzyme Blends". Saccharification and fermentation may also be separate. Thus in another aspect the invention relates to processes of producing fermentation products, comprising the following steps:

(i) saccharifying a starch-containing material at a temperature below the initial gelatinization temperature using a carbohydrate-source generating enzyme, e.g., a glucoamylase; and (ii) fermenting using a fermentation organism;

wherein step (i) and/or (ii) is carried out using at least a glucoamylase and at least one xylanase or enzyme blend of the invention. In an embodiment, a co-product of the process is recovered. The co-product may have improved nutritional quality compared to a co-product produced by a similar process where the xylanase or enzyme blend comprising xylanase are not present or added to pre-saccharification, saccharification, fermentation, or simultaneous saccharification and fermentation. In an embodiment, the co-product is DDG or DDGS. In an embodiment, the DDG or DDGS have increased TME, e.g., for monogastric animals, compared to DDG or DDGS produced by a similar process where the xylanase or enzyme blend comprising xylanase are not present or added to pre-saccharification, saccharification, fermentation, or simultaneous saccharification and fermentation.

In an embodiment, the xylanase or at least one enzyme blend of the present invention is added during saccharifying step (i). In an embodiment, the xylanase or at least one enzyme blend of the present invention is added during fermenting step (ii).

In one embodiment, an alpha amylase, in particular a fungal alpha-amylase, is also added in step (i). Steps (i) and (ii) may be performed simultaneously. In an embodiment, the xylanase or at least one enzyme blend of the present invention is added during simultaneous saccharification and fermentation (SSF). In an embodiment, the fermenting organism is yeast and the xylanase or at least one enzyme blend is added during yeast propagation.

Processes for Producing Fermentation Products from Gelatinized Starch-Containing Material In an aspect, the invention relates to processes for producing fermentation products, especially ethanol, from starch-containing material, which process includes a liquefaction step and sequentially or simultaneously performed saccharification and fermentation steps. Consequently, the invention relates to a process for producing a fermentation product from starch-containing material comprising the steps of:

(a) liquefying starch-containing material in the presence of an alpha-amylase to form a liquefied mash;

(b) saccharifying the liquefied mash using a carbohydrate-source generating enzyme to produce a fermentable sugar; and (c) fermenting the sugar using a fermenting organism under conditions suitable to produce the fermentation product;

wherein a xylanase or at least one enzyme blend of the present invention is added before or during step (c). In an embodiment, a co-product of the process is recovered. The co-product may have improved nutritional quality compared to a co-product produced by a similar process where the xylanase or enzyme blend comprising xylanase are not present or added to pre-saccharification, saccharification, fermentation, or simultaneous saccharification and fermentation. In an embodiment, the co-product is DDG or DDGS. In an embodiment, the DDG or DDGS have increased TME, e.g., for monogastric animals, compared to DDG or DDGS produced by a similar process where the xylanase or enzyme blend comprising xylanase are not present or added to pre-saccharification, saccharification, fermentation, or simultaneous saccharification and fermentation.

The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at a pH of 4-6, in particular at a pH of 4.5-5.5, and alpha-amylase variant, optionally together with a protease, a carbohydrate-source generating enzyme, such as a glucoamylase, a phospholipase, a phytase, and/or pullulanase, are added to initiate liquefaction (thinning). The liquefaction process is usually carried out at a pH of 4-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at a temperature from 20-75° C., in particular 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In embodiment fermentation is ongoing for 6 to 120 hours, in particular 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an embodiment the fermentation product is ethanol.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans, Candida boidinii, Candida diddensii, Candida shehatae, Candida sonorensis, Candida tropicalis,* or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Recovery of Fermentation Products

Subsequent to fermentation or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art. Typically, the fermentation product, e.g., ethanol, with a purity of up to, e.g., about 96 vol. percent ethanol is obtained.

Thus, in one embodiment, the method of the invention further comprises distillation to obtain the fermentation product, e.g., ethanol. The fermentation and the distillation may be carried out simultaneously and/or separately/sequentially; optionally followed by one or more process steps for further refinement of the fermentation product.

Following the completion of the distillation process, the material remaining is considered the whole stillage. As used herein, the term "whole stillage" includes the material that remains at the end of the distillation process after recovery of the fermentation product, e.g., ethanol. The fermentation product can optionally be recovered by any method known in the art.

Separating (Dewatering) Whole Stillage into Thin Stillage and Wet Cake

In one embodiment, the whole stillage is separated or partitioned into a solid and liquid phase by one or more methods for separating the thin stillage from the wet cake. Separating whole stillage into thin stillage and wet cake in order to remove a significant portion of the liquid/water, may be done using any suitable separation technique, including centrifugation, pressing and filtration. In a preferred embodiment, the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment, the separation is carried out using other conventional separation equipment such as a plate/frame filter presses, belt filter presses, screw presses, gravity thickeners and deckers, or similar equipment.

Processing of Thin Stillage

Thin stillage is the term used for the supernatant of the centrifugation of the whole stillage. Typically, the thin stillage contains 4-6 percent dry solids (DS) (mainly proteins, soluble fiber, fine fibers, and cell wall components) and has a temperature of about 60-90 degrees centigrade. The thin stillage stream may be condensed by evaporation to provide two process streams including: (i) an evaporator condensate stream comprising condensed water removed from the thin stillage during evaporation, and (ii) a syrup stream, comprising a more concentrated stream of the non-volatile dissolved and non-dissolved solids, such as non-fermentable sugars and oil, remaining present from the thin stillage as the result of removing the evaporated water. Optionally, oil can be removed from the thin stillage or can be removed as an intermediate step to the evaporation process, which is typically carried out using a series of several evaporation stages. Syrup and/or de-oiled syrup may be introduced into a dryer together with the wet grains (from the whole stillage separation step) to provide a product referred to as distillers dried grain with solubles, which also can be used as animal feed.

In an embodiment, syrup and/or de-oiled syrup is sprayed into one or more dryers to combine the syrup and/or de-oiled syrup with the whole stillage to produce distillers dried grain with solubles.

Between 5-90 vol-%, such as between 10-80%, such as between 15-70%, such as between 20-60% of thin stillage (e.g., optionally hydrolyzed) may be recycled (as backset) to step (a). The recycled thin stillage (i.e., backset) may constitute from about 1-70 vol.-%, preferably 15-60% vol.-%, especially from about 30 to 50 vol.-% of the slurry formed in step (a).

In an embodiment, the process further comprises recycling at least a portion of the thin stillage stream to the slurry, optionally after oil has been extracted from the thin stillage stream.

Drying of Wet Cake and Producing Distillers Dried Grains and Distillers Dried Grains with Solubles After the wet cake, containing about 25-40 wt-%, preferably 30-38 wt-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for animals, such as livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS). Partially dried intermediate products, such as are sometimes referred to as modified wet distillers grains, may be produced by partially drying wet cake, optionally with the addition of syrup before, during or after the drying process.

III. Processes for Improving the Nutritional Quality of DDG or DDGS

In another aspect, the present invention relates to a process for improving the nutritional quality of distillers dried grains (DGS) or distillers dried grains with solubles (DDGS) produced as a co-product of a fermentation product production process.

In an embodiment, a process for improving the nutritional quality of DGS or DDGS produced as a co-product of a fermentation production process comprises performing a process for producing a fermentation product described above in Section II (e.g., a RSH process or a conventional cook process including a liquefaction step) or Examples herein, and recovering the fermentation product to produce DGS or DDGS as a co-product, wherein the DGS or DDGS produced have improved nutritional quality. The step of recovering the fermentation product to produce DGS or DDGS as the co-product may include any one or combination of the above described steps of recovery of fermentation product(s), for example by distillation, to produce whole stillage, separating whole stillage into wet cake and thin stillage, processing of thin stillage, drying of wet cake and producing DDG or DDGS, etc.

As used herein, "improved nutritional quality" means an increase in the true metabolizable energy (TME) of the DDG or DDGS by at least 5% as compared to DDG or DDGS produced in a fermentation product production process (e.g., an RSH process or conventional cook process including a liquefaction step as set forth in Section II or the Examples herein) in which a presently disclosed xylanase or enzyme blend was not added during pre-saccharification, saccharification, fermentation, and/or simultaneous saccharification and fermentation.

In an embodiment, the enzyme blends and processes of the present invention increase the TME of the DDG or DDGS by at least 5%, at least 6%, at least 7%, at least 8%, at least 9%, at least 9%, at least 10%, at least 11%, at least 12%, at least 13%, at least 14%, at least 15%, at least 16%, at least 17%, at least 18%, at least 19%, at least 20%, at least 25%, at least 26%, at least 27%, at least 28%, at least 29%, or at least 30% as compared to DDG or DDGS produced in a fermentation product production process (e.g., an RSH process or conventional cook process including a liquefaction step as set forth in Section II or the Examples herein) in which a presently disclosed xylanase or enzyme blend was not added during pre-saccharification, saccharification, fermentation, and/or simultaneous saccharification and fermentation.

In an embodiment, the xylanase or enzyme blends and processes of the present invention improve the nutritional quality of the DDG or DDGS without resulting in a darkening of the DDG or DDGS after drying. Those skilled in the art will appreciate that the extent of darkening of the DDG or DDGS after drying following addition of a xylanase or an enzyme blend of the present invention during a fermentation product production process (e.g., during SSF while producing ethanol using a corn mash substrate) can be readily assessed, for example, by measuring the DDG or DDGS color using the Hunter Color scale (see Examples herein).

Enzymes

The enzyme(s) and polypeptides described below are to be used in an "effective amount" in blends or processes of the present invention. Below should be read in context of the enzyme disclosure in the "Definitions"-section above.

Cellulolytic Compositions Used in an Enzyme Blend or Process and Method of the Invention The cellulolytic composition used in a process of the invention for producing fermentation products may be derived from any microorganism. As used herein, "derived from any microorganism" means that the cellulolytic composition comprises one or more enzymes that were expressed in the microorganism. For instance, a cellulolytic composition derived from a strain of *Trichoderma reesei* means that the cellulolytic composition comprises one or more enzymes that were expressed in *Trichoderma reesei*.

In an embodiment, the cellulolytic composition is derived from a strain of *Aspergillus*, such as a strain of *Aspergillus aurantiacus, Aspergillus niger* or *Aspergillus oryzae*.

In an embodiment, the cellulolytic composition is derived from a strain of *Chrysosporium*, such as a strain of *Chrysosporium lucknowense*.

In an embodiment, the cellulolytic composition is derived from a strain of *Humicola*, such as a strain of *Humicola insolens*.

In an embodiment, the cellulolytic composition is derived from a strain of *Penicilium*, such as a strain of *Penicilium emersonii* or *Penicilium oxalicum*.

In an embodiment, the cellulolytic composition is derived from a strain of *Talaromyces*, such as a strain of *Talaromyces aurantiacus* or *Talaromyces emersonii*.

In an embodiment, the cellulolytic composition is derived from a strain of *Trichoderma*, such as a strain of *Trichoderma reesei*.

In a preferred embodiment, the cellulolytic composition is derived from a strain of *Trichoderma reesei*.

The cellulolytic composition may comprise one or more of the following polypeptides, including enzymes: GH61 polypeptide having cellulolytic enhancing activity, beta-glucosidase, CBHI and CBHII, or a mixture of two, three, or four thereof.

In a preferred embodiment, the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

The cellulolytic composition may comprise some hemicellulase, such as, e.g., xylanase and/or beta-xylosidase. The hemicellulase may come from the cellulolytic composition producing organism or from other sources, e.g., the hemicellulase may be foreign to the cellulolytic composition producing organism, such as, e.g., *Trichoderma reesei*.

In a preferred embodiment the hemicellulase content in the cellulolytic composition constitutes less than 10 wt. % such as less than 5 wt. % of the cellulolytic composition.

In an embodiment the cellulolytic composition comprises a beta-glucosidase.

In an embodiment the cellulolytic composition comprises a GH61 polypeptide having cellulolytic enhancing activity and a beta-glucosidase.

In another embodiment the cellulolytic composition comprises a beta-glucosidase and a CBH.

In another embodiment the cellulolytic composition comprises a GH61 polypeptide having cellulolytic enhancing activity, a beta-glucosidase, and a CBHI.

In another embodiment the cellulolytic composition comprises a beta-glucosidase and a CBHI.

In another embodiment the cellulolytic composition comprises a GH61 polypeptide having cellulolytic enhancing activity, a beta-glucosidase, a CBHI, and a CBHII.

In another embodiment the cellulolytic composition comprises a beta-glucosidase, a CBHI, and a CBHII.

The cellulolytic composition may further comprise one or more enzymes selected from the group consisting of a cellulase, a GH61 polypeptide having cellulolytic enhancing activity, an esterase, an expansin, a laccase, a ligninolytic enzyme, a pectinase, a peroxidase, a protease, and a swollenin.

In an embodiment the cellulase is one or more enzymes selected from the group consisting of an endoglucanase, a cellobiohydrolase, and a beta-glucosidase.

In an embodiment the endoglucanase is an endoglucanase I.

In an embodiment the endoglucanase is an endoglucanase II.

Beta-Glucosidase

The cellulolytic composition used according to the invention may in one embodiment comprise one or more beta-glucosidase. The beta-glucosidase may in one embodiment be one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or SEQ ID NO: 10 herein or an *Aspergillus fumigatus* beta-glucosidase variant, such as one disclosed in WO 2012/044915 or co-pending PCT application PCT/US11/054185 (or U.S. provisional application No. 61/388,997), such as one with the following substitutions: F100D, S283G, N456E, F512Y.

In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

In an embodiment betaglucosidase is an *Aspergillus fumigatus* beta-glucosidase or homolog thereof selected from the group consisting of:

(i) a beta-glucosidase comprising the mature polypeptide of SEQ ID NO: 10;

(ii) a beta-glucosidase comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 10 herein;

(iii) a beta-glucosidase encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 5 in WO 2013/148993; and (iv) a beta-glucosidase encoded by a polynucleotide that hybridizes under at least high stringency conditions, e.g., very high stringency conditions, with the mature polypeptide coding sequence of SEQ ID NO: 5 in WO) 2013/148993 or the full-length complement thereof.

In an embodiment the beta-glucosidase is a variant comprises a substitution at one or more (several) positions corresponding to positions 100, 283, 456, and 512 of the mature polypeptide of SEQ ID NO: 10 herein, wherein the variant has beta-glucosidase activity.

In an embodiment the parent beta-glucosidase of the variant is (a) a polypeptide comprising the mature polypeptide of SEQ ID) NO: 10 herein; (b) a polypeptide having at least 80% sequence identity to the mature polypeptide of SEQ ID NO: 10 herein; (c) a polypeptide encoded by a polynucleotide that hybridizes under high or very high stringency conditions with (i) the mature polypeptide coding sequence of SEQ ID NO: 5 in WO 2013/148993, (ii) the cDNA sequence contained in the mature polypeptide coding sequence of SEQ ID NO: 5 in WO 2013/148993, or (iii) the full-length complementary strand of (i) or (ii); (d) a polypeptide encoded by a polynucleotide having at least 80% identity to the mature polypeptide coding sequence of SEQ ID NO: 5 in WO 2013/148993 or the cDNA sequence thereof; or (e) a fragment of the mature polypeptide of SEQ ID NO: 10 herein, which has beta-glucosidase activity.

In an embodiment the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

In an embodiment the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 10 herein.

In an embodiment the beta-glucosidase is from a strain of *Aspergillus*, such as a strain of *Aspergillus fumigatus*, such as *Aspergillus fumigatus* beta-glucosidase (SEQ ID NO: 10 herein), which comprises one or more substitutions selected from the group consisting of L89M, G91L, F100D, I140V, I186V, S283G, N456E, and F512Y; such as a variant thereof with the following substitutions:
F100D+S283G+N456E+F512Y;
L89M+G91L+I186V+I140V;
I186V+L89M+G91L+I140V+F100D+S283G+N456E+F512Y.

In an embodiment the number of substitutions is between 1 and 4, such as 1, 2, 3, or 4 substitutions.

In an embodiment the variant comprises a substitution at a position corresponding to position 100, a substitution at a position corresponding to position 283, a substitution at a position corresponding to position 456, and/or a substitution at a position corresponding to position 512.

In a preferred embodiment the beta-glucosidase variant comprises the following substitutions: Phe100Asp, Ser283Gly, Asn456Glu, Phe512Tyr in SEQ ID NO: 10 herein.

In a preferred embodiment the beta-glucosidase has a Relative ED50 loading value of less than 1.00, preferably less than 0.80, such as preferably less than 0.60, such as between 0.1-0.9, such as between 0.2-0.8, such as 0.30-0.70.

GH61 Polypeptide Having Cellulolytic Enhancing Activity

The cellulolytic composition used according to the invention may in one embodiment comprise one or more GH61 polypeptide having cellulolytic enhancing activity. In one embodiment the enzyme composition comprises a GH61 polypeptide having cellulolytic enhancing activity, such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 2; or one derived from a strain derived from *Penicillium*, such as a strain of *Penicillium emersonii*, such as the one disclosed in WO 2011/041397 or SEQ ID NO: 11 herein.

In an embodiment the *Penicillium* sp. GH61 polypeptide having cellulolytic enhancing activity or homolog thereof is selected from the group consisting of:
(i) a GH61 polypeptide having cellulolytic enhancing activity comprising the mature polypeptide of SEQ ID NO: 11 herein;
(ii) a GH61 polypeptide having cellulolytic enhancing activity comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 11 herein;
(iii) a GH61 polypeptide having cellulolytic enhancing activity encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 7 in WO 2013/148993; and
(iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 in WO 2013/148993 or the full-length complement thereof.

Cellobiohydrolase I

The cellulolytic composition used according to the invention may in one embodiment may comprise one or more CBH I (cellobiohydrolase I). In one embodiment the cellulolytic composition comprises a cellobiohydrolase I (CBHI), such as one derived from a strain of the genus *Aspergillus*, such as a strain of *Aspergillus fumigatus*, such as the Cel7A CBHI disclosed in SEQ ID NO: 6 in WO 2011/057140 or SEQ ID NO: 8 herein, or a strain of the genus *Trichoderma*, such as a strain of *Trichoderma reesei*.

In an embodiment the *Aspergillus fumigatus* cellobiohydrolase I or homolog thereof is selected from the group consisting of:
(i) a cellobiohydrolase I comprising the mature polypeptide of SEQ ID NO: 8 herein;
(ii) a cellobiohydrolase I comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 8 herein;
(iii) a cellobiohydrolase I encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 1 in WO 2013/148993; and
(iv) a cellobiohydrolase I encoded by a polynucleotide that hybridizes under at least high stringency conditions, e.g., very high stringency conditions, with the mature polypeptide coding sequence of SEQ ID NO: 1 in WO 2013/148993 or the full-length complement thereof.

Cellobiohydrolase II

The cellulolytic composition used according to the invention may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*, such as the one in SEQ ID NO: 9 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the *Aspergillus fumigatus* cellobiohydrolase II or homolog thereof is selected from the group consisting of:
(i) a cellobiohydrolase II comprising the mature polypeptide of SEQ ID NO: 9 herein;
(ii) a cellobiohydrolase II comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 9 herein;
(iii) a cellobiohydrolase II encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 3 in WO 2013/148993; and
(iv) a cellobiohydrolase II encoded by a polynucleotide that hybridizes under at least high stringency conditions, e.g., very high stringency conditions, with the mature polypeptide coding sequence of SEQ ID NO: 3 in WO 2013/148993 or the full-length complement thereof.

Cellulolytic Compositions

As mentioned above the cellulolytic composition may comprise a number of difference polypeptides, such as enzymes.

In an embodiment the cellulolytic composition comprises a *Trichoderma reesei* cellulolytic composition, further comprising *Thermoascus aurantiacus* GH61A polypeptide having cellulolytic enhancing activity (WO 2005/074656) and *Aspergillus oryzae* beta-glucosidase fusion protein (WO 2008/057637).

In another embodiment the cellulolytic composition comprises a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499).

In another embodiment the cellulolytic composition comprises a *Trichoderma reesei* cellulolytic composition, further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) or a variant thereof with the following substitutions: F100D, S283G, N456E, F512Y.

The enzyme composition of the present invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In a preferred embodiment the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

In an embodiment cellulolytic enzyme composition is dosed (i.e. during saccharification in step ii) and/or fermentation in step iii) or SSF) from 0.0001-3 mg EP/g DS, preferably 0.0005-2 mg EP/g DS, preferably 0.001-1 mg'g DS, more preferred from 0.005-0.5 mg EP/g DS, even more preferred 0.01-0.1 mg EP/g DS.

Alpha-Amylase Present and/or Added During Liquefaction

According to the invention an alpha-amylase is present and/or added in liquefaction optionally together with a hemicellulase, an endoglucanase, a protease, a carbohydrate-source generating enzyme, such as a glucoamylase, a phospholipase, a phytase, and/or pullulanase.

The alpha-amylase added during liquefaction step i) may be any alpha-amylase. Preferred are bacterial alpha-amylases, such as especially *Bacillus* alpha-amylases, such as *Bacillus stearothermophilus* alpha-amylases, which are stable at temperature used during liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus, Bacillus* sp. TS-23, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467 or SEQ ID NO: 12 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 and the *Bacillus* sp. TS-23 alpha-amylase disclosed as SEQ ID NO: 1 in WO 2009/061380 (all sequences are hereby incorporated by reference).

In an embodiment the bacterial alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467 and SEQ ID NO: 1 in WO 2009/061380.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 12 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases, or variant thereof, may be naturally truncated during recombinant production. For instance, the mature *Bacillus stearothermophilus* alpha-amylase may be truncated at the C-terminal so it is around 491 amino acids long (compared to SEQ ID NO: 3 in WO 99/19467 or SEQ ID NO: 12 herein), such as from 480-495 amino acids long.

The *Bacillus* alpha-amylase may also be a variant and/or hybrid. Examples of such a variant can be found in any of WO 96/23873, WO 96/23874, WO 97/41213, WO 99/19467, WO 00/60059, WO 02/10355 and WO2009/061380 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 12 herein or the deletion of amino acids R179 and G180 using SEQ ID NO: 3 in WO 99/19467 or SEQ ID NO: 12 herein. Even more preferred are *Bacillus* alpha-amylases, especially *Bacillus stearothermophilus* (BSG) alpha-amylases, which have at one or two amino acid deletions corresponding to positions R179, G180, I181 and G182, preferably which have a double deletion corresponding to R179 and G180, or preferably a deletion of positions 181 and 182 (denoted I181*+G182*), and optionally further comprises a N193F substitution (denoted I181*+G182*+N193F) compared to the wild-type BSG alpha-amylase amino acid sequence set forth in SEQ ID NO: 3 disclosed in WO 99/19467 or SEQ ID NO: 12 herein. The bacterial alpha-amylase may also have a substitution in a position corresponding to S239 in the *Bacillus licheniformis* alpha-amylase shown in SEQ ID NO: 4 in WO 99/19467, or a S242 variant in the *Bacillus stearothermophilus* alpha-amylase of SEQ ID NO: 3 in WO 99/19467 or SEQ ID NO: 12 herein.

In an embodiment the variant is a S242A, E or Q variant, preferably a S242Q or A variant, of the *Bacillus stearothermophilus* alpha-amylase (using SEQ ID NO: 12 herein for numbering).

In an embodiment the variant is a position E188 variant, preferably E188P variant of the *Bacillus stearothermophilus* alpha-amylase (using SEQ ID NO: 12 herein for numbering).

Other contemplated variant are *Bacillus* sp. TS-23 variant disclosed in WO2009/061380, especially variants defined in claim 1 of WO2009/061380 (hereby incorporated by reference).

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions: G48A+T49I+G107A+H156Y+A181T+ N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al., 2002, The Journal of Biological Chemistry 277 (29): 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

According to the invention the alpha-amylase is optionally used in combination with a hemicellulase, preferably xylanase, having a Melting Point (DSC) above 80° C.

Optionally an endoglucanase having a Melting Point (DSC) above 70° C., such as above 75° C., in particular above 80° C. may be included. The thermostable alpha-amylase, such as a bacterial an alpha-amylase, is preferably derived from *Bacillus stearothermophilus* or *Bacillus* sp. TS-23. In an embodiment the alpha-amylase has a T½ (min) at pH 4.5, 85° C., 0.12 mM CaCl$_2$) of at least 10. In an embodiment the alpha-amylase has a T½ (min) at pH 4.5, 85° C., 0.12 mM CaCl$_2$), of at least 15. In an embodiment the alpha-amylase has a T½ (min) at pH 4.5, 85° C., 0.12 mM CaCl$_2$), of at least 20. In an embodiment the alpha-amylase has a T½ (min) at pH 4.5, 85° C., 0.12 mM CaCl$_2$), of at least 25. In an embodiment the alpha-amylase has a T½ (min) at pH 4.5, 85° C., 0.12 mM CaCl$_2$), of at least 30. In an embodiment the alpha-amylase has a T½ (min) at pH 4.5, 85° C., 0.12 mM CaCl$_2$), of at least 40. In an embodiment the alpha-amylase has a T½ (min) at pH 4.5, 85° C., 0.12 mM CaCl$_2$), of at least 50. In an embodiment the alpha-amylase has a T½ (min) at pH 4.5, 85° C., 0.12 mM CaCl$_2$), of at least 60. In an embodiment the alpha-amylase has a T½ (min) at pH 4.5, 85° C., 0.12 mM CaCl$_2$), between 10-70. In an embodiment the alpha-amylase has a T½ (min) at pH 4.5, 85° C., 0.12 mM CaCl$_2$), between 15-70. In an embodiment the alpha-amylase has a T½ (min) at pH 4.5, 85° C., 0.12 mM CaCl$_2$), between 20-70. In an embodiment the alpha-amylase has a T½ (min) at pH 4.5, 85° C., 0.12 mM CaCl$_2$, between 25-70. In an embodiment the alpha-amylase has a T½ (min) at pH 4.5, 85° C., 0.12 mM CaCl$_2$), between 30-70. In an embodiment the alpha-amylase has a T½ (min) at pH 4.5, 85° C., 0.12 mM CaCl$_2$), between 40-70. In an embodiment the alpha-amylase has a T½ (min) at pH 4.5, 85° C., 0.12 mM CaCl$_2$), between 50-70. In an embodiment the alpha-amylase has a T½ (min) at pH 4.5, 85° C., 0.12 mM CaCl$_2$), between 60-70.

In an embodiment the alpha-amylase is a bacterial alpha-amylase, preferably derived from the genus *Bacillus*, especially a strain of *Bacillus stearothermophilus*, in particular the *Bacillus stearothermophilus* as disclosed in WO 99/19467 as SEQ ID NO: 3 or SEQ ID NO: 12 herein with one or two amino acids deleted at positions R179, G180, I181 and/or G182, in particular with R179 and G180 deleted, or with I181 and G182 deleted, with mutations in below list of mutations. In preferred embodiments the *Bacillus stearothermophilus* alpha-amylases have double deletion I181+G182, and optional substitution N193F, optionally further comprising mutations selected from below list:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N ;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + El 29V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M961 + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;

E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A + Q89R + E129V + K177L + R179E + Q254S + M284V.

In an embodiment the alpha-amylase is selected from the group of *Bacillus stearothermphilus* alpha-amylase variants:
I181*+G182*;
I181*+G182*+N193F;
preferably
I181*+G182*+E129V+K177L+R179E;
I181*+G182*+N193F+E129V+K177L+R179E;
181*+G182*+N193F+V59A+Q89R+E129V+K177L+R179E+H208Y+K220P+N224L+Q254S;
I181*+G182*+N193F+V59A+Q89R+E129V+K177L+R179E+Q254S+M284V; and
I181*+G182*+N193F+E129V+K177L+R179E+K220P+N224L+S242Q+Q254S (using SEQ ID NO: 12 herein for numbering).

In an embodiment the bacterial alpha-amylase, such as *Bacillus* alpha-amylase, such as *Bacillus stearothermophilus* alpha-amylase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 12 herein.

In an embodiment the bacterial alpha-amylase variant, such as *Bacillus* alpha-amylase variant, such as *Bacillus stearothermophilus* alpha-amylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 12 herein.

It should be understood that when referring to *Bacillus stearothermophilus* alpha-amylase and variants thereof they are normally produced naturally in truncated form. In particular, the truncation may be so that the *Bacillus stearothermophilus* alpha-amylase shown in SEQ ID NO: 3 in WO 99/19467 or SEQ ID NO: 12 herein, or variants thereof, are truncated in the C-terminal and are typically around 491 amino acids long, such as from 480-495 amino acids long.

Thermostable Hemicellulase Present and/or Added During Liquefaction

According to the invention an optional hemicellulase, preferably xylanase, having a Melting Point (DSC) above 80° C. is present and/or added to liquefaction step i) in combination with an alpha-amylase, such as a bacterial alpha-amylase (described above).

The thermostability of a hemicellulase, preferably xylanase may be determined as described in the "Materials & Methods"-section under "Determination of Ta by Differential Scanning calorimetry for Endoglucanases and Hemicellulases".

In an embodiment the hemicellulase, in particular xylanase, especially GH10 or GH11 xylanase has a Melting Point (DSC) above 82° C., such as above 84° C., such as above 86° C., such as above 88° C., such as above 88° C., such as above 90° C., such as above 92° C., such as above 94° C., such as above 96° C., such as above 98° C., such as above 100° C., such as between 80° C. and 110° C., such as between 82° C. and 110° C., such as between 84° C. and 110° C.

In a preferred embodiment the hemicellulase, in particular xylanase, especially GH10 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 13 herein, preferably derived from a strain of the genus *Dictyoglomus*, such as a strain of *Dictyogllomus thermophilum*.

In a preferred embodiment the hemicellulase, in particular xylanase, especially GH11 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 14 herein, preferably derived from a strain of the genus *Dictyoglomus*, such as a strain of *Dictyogllomus thermophilum*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 15 herein, preferably derived from a strain of the genus Rasamsonia, such as a strain of *Rasomsonia byssochlamydoides*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 16 herein, preferably derived from a strain of the genus *Talaromyces*, such as a strain of *Talaromyces leycettanus*.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 17 herein, preferably derived from a strain of the genus *Aspergillus*, such as a strain of *Aspergillus fumigatus*.

Thermostable Endoglucanase Present and/or Added During Liquefaction

According to the invention an optional endoglucanase ("E") having a Melting Point (DSC) above 70° C., such as between 70° C. and 95° C. may be present and/or added in liquefaction step i) in combination with an alpha-amylase, such as a thermostable bacterial alpha-amylase and an optional hemicellulase, preferably xylanase, having a Melting Point (DSC) above 80° C.

The thermostability of an endoglucanase may be determined as described in the "Materials & Methods"-section of WO 2017/112540 (incorporated herein by reference in its entirety) under the heading "Determination of Ta by Differential Scanning Calorimetry for Endoglucanases and Hemicellulases".

In an embodiment the endoglucanase has a Melting Point (DSC) above 72° C., such as above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In a preferred embodiment the endogluconase used in a process of the invention or comprised in a composition of the invention is a Glycoside Hydrolase Family 5 endoglucnase or GH5 endoglucanase (see the CAZy database on the world wide web page cazy.org).

In an embodiment the GH15 endoglucanase is from family EG II, such as the *Talaromyces leycettanus* endoglucanase shown in SEQ ID NO: 18 herein; *Penicillium capsulatum* endoglucanase shown in SEQ ID NO: 19 herein, and *Trichophaea saccata* endoglucanase shown in SEQ ID NO: 20 herein.

In an embodiment the endoglucanase is a family GH45 endoglucanase. In an embodiment the GH45 endoglucanase is from family EG V, such as the *Sordaria fimicola* shown in SEQ ID NO: 21 herein or the *Thielavia terrestris* endoglucanase shown in SEQ ID NO: 22 herein.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 18 herein. In an embodiment the endoglucanase is derived from a strain of the genus *Talaromyces*, such as a strain of *Talaromyces leycettanus*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 19 herein, preferably derived from a strain of the genus *Penicillium*, such as a strain of *Penicillium capsulatum*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 20 herein, preferably derived from a strain of the genus *Trichophaea*, such as a strain of *Trichophaea saccata*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 21 herein, preferably derived from a strain of the genus *Sordaria*, such as a strain of *Sordaria fimicola*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 22 herein, preferably derived from a strain of the genus *Thielavia*, such as a strain of *Thielavia terrestris*.

In an embodiment the endoglucanase is added in liquefaction step i) at a dose from 1-10,000 μg EP (Enzymes Protein)/g DS), such as 10-1,000 μg EP/g DS.

Carbohydrate-Source Generating Enzyme Present and/or Added During Liquefaction

According to the invention an optional carbohydrate-source generating enzyme, in particular a glucoamylase, preferably a thermostable glucoamylase, may be present and/or added in liquefaction together with an alpha-amylase and optional hemicellulase, preferably xylanase, having a Melting Point (DSC) above 80° C., and an optional endoglucanase having a Melting Point (DSC) above 70° C., and an optional a pullulanase and/or optional phytase.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 23 herein.

In an embodiment the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 23 herein.

In an embodiment the carbohydrate-source generating enzyme, in particular thermostable glucoamylase, is the *Penicillium oxalicum* glucoamylase shown in SEQ ID NO: 23 herein.

In a preferred embodiment the carbohydrate-source generating enzyme is a variant of the *Penicillium oxalicum* glucoamylase disclosed as SEQ ID NO: 2 in WO 2011/127802 and shown in SEQ ID NO: 23 herein, having a K79V substitution (referred to as "PE001") (using the mature sequence shown in SEQ ID NO: 14 for numbering). The K79V glucoamylase variant has reduced sensitivity to protease degradation relative to the parent as disclosed in WO 2013/036526 (which is hereby incorporated by reference).

Contemplated *Penicillium oxalicum* glucoamylase variants are disclosed in WO 2013/053801 (which is hereby incorporated by reference).

In an embodiment these variants have reduced sensitivity to protease degradation.

In an embodiment these variant have improved thermostability compared to the parent.

More specifically, in an embodiment the glucoamylase has a K79V substitution (using SEQ ID NO: 23 herein for numbering), corresponding to the PE001 variant, and further comprises at least one of the following substitutions or combination of substitutions:

T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K33C+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+D26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+Q327F+E501V+Y504T; P2N+P4S+P11F+T65A+Q327F+E501V+Y504T+T516P+K524T+G526A; P2N+P4S+P11F+T65A+Q327F+E501V+N502T+Y504*; P2N+P4S+P11F+T65A+Q327F+E501V+Y504T; P2N+P4S+P11F+T65A+S103N+Q327F+E501V+Y504T; K5A+P11F+T65A+Q327F+E501V+Y504T; P2N+P4S+P11F+T65A+Q327F+E501V+Y504T+T516P+K524T+G526A; P2N+P4S+P11F+T65A+V79A+Q327F+E501V+Y504T; P2N+P4S+P11F+T65A+V79G+Q327F+E501V+Y504T; P2N+P4S+P11F+T65A+V79I+Q327F+E501V+Y504T; P2N+P4S+P11F+T65A+V79L+Q327F+E501V+Y504T; P2N+P4S+P11F+T65A+V79S+Q327F+E501V+Y504T; P2N+P4S+P11F+T65A+L72V+Q327F+E501V+Y504T; S255N+Q327F+E501V+Y504T; P2N+P4S+P11F+T65A+E74N+Q327F+E501V+Y504T; P2N+P4S+P11F+T65A+G220N+Q327F+E501V+Y504T; P2N+P4S+P11F+T65A+Y245N+Q327F+E501V+Y504T; P2N+P4S+P11F+T65A+Q253N+Q327F+E501V+Y504T; P2N+P4S+P11F+T65A+D279N+Q327F+E501V+Y504T; P2N+P4S+P11F+T65A+Q327F+S359N+E501V+Y504T; P2N+P4S+P11F+T65A+Q327F+D370N+E501V+Y504T; P2N+P4S+P11F+T65A+Q327F+V460S+E501V+Y504T; P2N+P4S+P11F+T65A+Q327F+V460T+P468T+E501V+Y504T; P2N+P4S+P11F+T65A+Q327F+T463N+E501V+Y504T; P2N+P4S+P11F+T65A+Q327F+S465N+E501V+Y504T; or P2N+P4S+P11F+T65A+Q327F+T477N+E501V+Y504T.

In a preferred embodiment the *Penicillium oxalicum* glucoamylase variant has a K79V substitution using SEQ ID NO: 23 herein for numbering (PE001 variant), and further comprises one of the following mutations:

P11F+T65A+Q327F;
P2N+P4S+P11F+T65A+Q327F;

P11F+D26C+K33C+T65A+Q327F;
P2N+P4S+P11F+T65A+Q327W+E501V+Y504T;
P2N+P4S+P11F+T65A+Q327F+E501V+Y504T; or
P11F+T65A+Q327W+E501V+Y504T.

In an embodiment the glucoamylase variant, such as *Penicillium oxalicum* glucoamylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature polypeptide of SEQ ID NO: 23 herein.

The carbohydrate-source generating enzyme, in particular glycoamylase, may be added in amounts from 0.1-100 micrograms EP/g DS, such as 0.5-50 micrograms EP/g DS, such as 1-25 micrograms EP/g DS, such as 2-12 micrograms EP/g DS.

Pullulanase Present and/or Added During Liquefaction

Optionally a pullulanase may be present and/or added during liquefaction step i) together with an alpha-amylase and an optional hemicellulase, preferably xylanase, having a melting point (DSC) above 80° C. As mentioned above a protease, a carbohydrate-source generating enzyme, preferably a thermostable glucoamylase, may also optionally be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO 92/02614.

In an embodiment the pullulanase is a family GH57 pullulanase. In an embodiment the pullulanase includes an X47 domain as disclosed in WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown WO 2011/087836 truncated at the X4 site right after the X47 domain. The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in WO 2011/087836 (which is hereby incorporated by reference).

In another embodiment the pullulanase is one comprising an X46 domain disclosed in WO 2011/076123 (Novozymes).

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME 400L, PROMOZYME™ D2 (Novozymes A/S, Denmark), OPTIMAX L-300 (Genencor Int., USA), and AMANO 8 (Amano, Japan).

Phytase Present and/or Added During Liquefaction

Optionally a phytase may be present and/or added in liquefaction in combination with an alpha-amylase and optional hemicellulase, preferably xylanase, having a melting point (DSC) above 80° C.

A phytase used according to the invention may be any enzyme capable of effecting the liberation of inorganic phosphate from phytic acid (myo-inositol hexakisphosphate) or from any salt thereof (phytates). Phytases can be classified according to their specificity in the initial hydrolysis step, viz. according to which phosphate-ester group is hydrolyzed first. The phytase to be used in the invention may have any specificity, e.g., be a 3-phytase (EC 3.1.3.8), a 6-phytase (EC 3.1.3.26) or a 5-phytase (no EC number). In an embodiment the phytase has a temperature optimum above 50° C., such as in the range from 50-90° C.

The phytase may be derived from plants or microorganisms, such as bacteria or fungi, e.g., yeast or filamentous fungi.

A plant phytase may be from wheat-bran, maize, soy bean or lily pollen. Suitable plant phytases are described in Thomlinson et al, Biochemistry, 1 (1962), 166-171; Barrientos et al, Plant. Physiol., 106 (1994), 1489-1495; WO 98/05785; WO 98/20139.

A bacterial phytase may be from genus *Bacillus, Citrobacter, Hafnia, Pseudomonas, Buttiauxella* or *Escherichia*, specifically the species *Bacillus subtilis, Citrobacter braakii, Citrobacter freundii, Hafnia alvei, Buttiauxella gaviniae, Buttiauxella agrestis, Buttiauxella noackies* and *E. coli*. Suitable bacterial phytases are described in Paver and Jagannathan, 1982, Journal of Bacteriology 151:1102-1108; Cosgrove, 1970, Australian Journal of Biological Sciences 23:1207-1220; Greiner et al, Arch. Biochem. Biophys., 303, 107-113, 1993; WO 1997/33976; WO 1997/48812, WO 1998/06856, WO 1998/028408, WO 2004/085638, WO 2006/037327, WO 2006/038062, WO 2006/063588, WO 2008/092901, WO 2008/116878, and WO 2010/034835.

A yeast phytase may be derived from genus *Saccharomyces* or *Schwanniomyces*, specifically species *Saccharomyces cerevisiae* or *Schwanniomyces occidentalis*. The former enzyme has been described as a Suitable yeast phytases are described in Nayini et al, 1984, Lebensmittel Wissenschaft und Technologie 17:24-26; Wodzinski et al, Adv. Appl. Microbiol., 42, 263-303; AU-A-24840/95;

Phytases from filamentous fungi may be derived from the fungal phylum of Ascomycota (ascomycetes) or the phylum Basidiomycota, e.g., the genus *Aspergillus, Thermomyces* (also called *Humicola*), *Myceliophthora, Manascus, Penicillium, Peniophora, Agrocybe, Paxillus,* or *Trametes,* specifically the species *Aspergillus terreus, Aspergillus niger, Aspergillus niger* var. *awamori, Aspergillus ficuum, Aspergillus fumigatus, Aspergillus oryzae, T. lanuginosus* (also known as *H. lanuginosa*), *Myceliophthora thermophila, Peniophora lycii, Agrocybe pediades, Manascus anka, Paxillus involtus,* or *Trametes pubescens*. Suitable fungal phytases are described in Yamada et al., 1986, Agric. Biol. Chem. 322:1275-1282; Piddington et al., 1993, Gene 133: 55-62; EP 684,313; EP 0 420 358; EP 0 684 313; WO 1998/28408; WO 1998/28409; JP 7-67635; WO 1998/44125; WO 1997/38096; WO 1998/13480.

In a preferred embodiment the phytase is derived from *Buttiauxella*, such as *Buttiauxella gaviniae, Buttiauxella agrestis*, or *Buttiauxella noackies*, such as the ones disclosed as SEQ ID NO: 2, SEQ ID NO: 4 and SEQ ID NO: 6, respectively, in WO 2008/092901 (hereby incorporated by reference).

In a preferred embodiment the phytase is derived from *Citrobacter*, such as *Citrobacter braakii*, such as one disclosed in WO 2006/037328 (hereby incorporated by reference).

Modified phytases or phytase variants are obtainable by methods known in the art, in particular by the methods disclosed in EP 897010; EP 897985; WO 99/49022; WO 99/48330, WO 2003/066847, WO 2007/112739, WO 2009/129489, and WO 2010/034835.

Commercially available phytase containing products include BIO-FEED PHYTASE™, PHYTASE NOVO™ CT or L (all from Novozymes), LIQMAX (DuPont) or RONOZYME™ NP, RONOZYME® HiPhos, RONOZYME® P5000 (CT), NATUPHOS™ NG 5000 (from DSM).

Carbohydrate-Source Generating Enzyme Present and/or Added During Saccharification and/or Fermentation According to the invention a carbohydrate-source generating enzyme, preferably a glucoamylase, is present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, Glucoamylase According to the invention the glucoamylase present and/or added in saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulata, Pachykytospora papyracea*; and *Leucopaxillus giganteus* all disclosed in WO 2006/069289; and *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (SEQ ID NOs 2, 4 or 6), or from a strain of the genus *Gloeophyllum*, in particular a strain of *Gloeophyllum* as described in WO 2011/068803 (SEQ ID NO: 2, 4, 6, 8, 10, 12, 14 or 16) or a strain of the genus *Nigrofomes*, in particular a strain of *Nigrofomes* sp. disclosed in WO 2012/064351 (SEQ ID NO: 2) (all references hereby incorporated by reference). Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME™ ACHIEVE and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYMET and G990 ZR (from Danisco US).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

Protease Present and/or Added During Liquefaction

In an embodiment of the invention an optional protease, such as a thermostable protease, may be present and/or added in liquefaction together with an alpha-amylase, such as a thermostable alpha-amylase, and a hemicellulase, preferably xylanase, having a melting point (DSC) above 80° C., and optionally an endoglucanase, a carbohydrate-source generating enzyme, in particular a glucoamylase, optionally a pullulanase and/or optionally a phytase.

Proteases are classified on the basis of their catalytic mechanism into the following groups: Serine proteases(S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section of WO 2017/112540 (incorporated herein by reference), of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the JTP196 variant (Example 2 from WO 2017/112540) or Protease Pfu (SEQ ID NO: 24 herein) determined by the AZCL-casein assay described in the "Materials & Methods"-section in WO 2017/112540.

There are no limitations on the origin of the thermostable protease used in a process or composition of the invention as long as it fulfills the thermostability properties defined below.

In one embodiment the protease is of fungal origin.

In a preferred embodiment the thermostable protease is a variant of a metallo protease as defined above. In an embodiment the thermostable protease used in a process or composition of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 25 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In a preferred embodiment the thermostable protease is a variant of the mature metallo protease disclosed as the mature part of SEQ ID NO: 2 disclosed in WO 2003/048353 or the mature part of SEQ ID NO: 1 in WO 2010/008841 or SEQ ID NO: 25 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 25 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 24 herein.

In an embodiment the thermostable protease is one disclosed in SEQ ID NO: 24 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 24 herein. The *Pyroccus furiosus* protease can be purchased from Takara Bio, Japan.

The *Pyrococcus furiosus* protease is a thermostable protease according to the invention. The commercial product *Pyrococcus furiosus* protease (Pfu S) was found (see Example 5 of) to have a thermostability of 110% (80° C./70° C.) and 103% (90° C./70° C.) at pH 4.5 determined as described in Example 2 of WO 2017/112540.

In one embodiment a thermostable protease has a thermostability value of more than 20% determined as Relative Activity at 80° C./70° C. determined as described in Example 2.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C.

In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C. determined as described in Example 2 of WO 2017/112540.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2 of WO 2017/112540.

In an embodiment the protease may have a themostability for above 90, such as above 100 at 85° C. as determined using the Zein-BCA assay as disclosed in Example 3 of WO 2017/112540.

In an embodiment the protease has a thermostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay described in the "Materials & Methods"-section of WO 2017/112540.

IV. Further Aspects of the Invention

In a further aspect of the invention it relates to the use of a xylanase (e.g., GH30_8 xylanase) or an enzyme blend of the present invention for improving the nutritional quality of distillers dried grains (DGS) or distillers dried grains with solubles (DDGS) produced as a co-product of a fermentation product production process of the present invention, preferably without resulting in a darkening the DDG or DDGS.

Any enzyme blend disclosed in Section I herein can be used in this manner. In various embodiments of this aspect, an additional enzyme, such as an enzyme or enzyme composition described under the "Enzymes" section can be used in combination together with an enzyme blend of the present invention.

In an embodiment, the xylanase or enzyme blend is used to improve the nutritional quality of DGS or DDGS by increasing the TME of the DDG or DDGS when administered to an animal (e.g., non-ruminant, e.g., monogastric, e.g., poultry or swine, etc.) by at least 5%, at least 6%, at least 7%, at least 8%, at least 9%, at least 10%, at least 11%, at least 12%, at least 13% at least 14%, at least 15%, at least 16%, at least 17%, at least 18%, at least 19%, or at least 20% compared to the TME of the DDG or DDGS produced as a co-product when a xylanase or an enzyme blend of the present invention is not present during the saccharification, fermentation, or simultaneous sacharification and fermentation step(s) of a fermentation product production process used to produce DDG or DDGS the co-product. In an embodiment, the xylanase or enzyme blend is used to improve the nutritional quality of DGS or DDGS by increasing the TME of the DDG or DDGS in an animal (e.g., non-ruminant, e.g., monogastric, e.g., poultry or swine, etc.) by at least 21%, at least 22%, at least 23%, at least 24%, at least 25%, at least 26%, at least 27%, at least 28%, at least 29%, at least 30%, at least 31%, at least 32%, at least 33% at least 44%, at least 45%, at least 46%, at least 47%, at least 48%, at least 49%, or at least 50% compared to the TME of the DDG or DDGS produced as a co-product when xylanase or an enzyme blend of the present invention is not present during the saccharification, fermentation, or simultaneous sacharification and fermentation step(s) of a fermentation product production process used to produce the DDG or DDGS co-product.

In still a further aspect of the invention it relates to the use of a xylanase or an enzyme blend of the present invention for increasing the solubilisation of fiber present in a fermentation mash during a fermentation product production process of the present invention, preferably without resulting in a darkening the DDG or DDGS. In an embodiment, the xylanase or enzyme blend is used to increase fiber solubilisation during the production of alcohol (e.g., ethanol) from a starch-containing material. In an embodiment, the xylanase or enzyme blend is used to increase the solubilisation of corn fiber in an ethanol production process, such as a RSH process or convention cook including a liquefaction step. In an embodiment, the enzyme blend is used to increase the solubilisation of arabinose. In an embodiment, the enzyme blend is used to increase the solubilisation of xylose.

Any xylanase or enzyme blend disclosed in Section I herein can be used in this manner. In various embodiments of this aspect, an additional enzyme, such as an enzyme or enzyme composition described under the "Enzymes" section can be used in combination together with an enzyme blend of the present invention.

In an embodiment, the xylanase or enzyme blend is used to increase the solubilisation of fiber (e.g., arabinose, xylose, etc.) contacted with the enzyme blend by at least 5%, at least 6%, at least 7%, at least 8%, at least 9%, at least 10%, at least 11%, at least 12%, at least 13% at least 14%, at least 15%, at least 16%, at least 17%, at least 18%, at least 19%, or at least 20% compared to the solubilisation of fiber not contacted with a xylanase or an enzyme blend of the present invention. In an embodiment, the xylanase or enzyme blend is used to increase the solubilisation of fiber (e.g., arabinose, xylose, etc.) contacted with the enzyme blend by at least 21%, at least 22%, at least 23%, at least 24%, at least 25%, at least 26%, at least 27%, at least 28%, at least 29%, at least 30%, at least 31%, at least 32%, at least 33% at least 44%, at least 45%, at least 46%, at least 47%, at least 48%, at least 49%, or at least 50% compared to fiber not contacted with the xylanase or enzyme blend.

The invention is further summarized in the following paragraphs:

1. A process of producing a fermentation product, comprising the following steps:
   (a) saccharifying a starch-containing material at a temperature below the initial gelatinization temperature with an alpha-amylase, a glucoamylase, and a xylanase or an enzyme blend comprising the xylanase;
   (b) fermenting using a fermentation organism to produce the fermentation product; and
   (c) optionally recovering a co-product.
2. A process for producing a fermentation product from starch-containing material comprising the steps of:
   (a) liquefying a starch-containing material with an alpha-amylase;
   (b) saccharifying the liquefied material obtained in step (a) with a glucoamylase and a xylanase or enzyme blend comprising the xylanase;
   (c) fermenting using a fermentation organism; and
   (d) optionally recovering a co-product.
3. The process of paragraphs 1 or 2, wherein saccharification and fermentation is performed simultaneously.
4. The process of any one of paragraphs 1 to 3, wherein the starch-containing material comprises maize, corn, wheat, rye, barley, triticale, sorghum, switchgrass, millet, pearl millet, foxtail millet.
5. The process of any one of paragraphs 1 to 4, wherein the fermentation product is alcohol, particularly ethanol.
6. The process of any one of paragraphs 1 to 5, wherein the co-product is distillers dried grains (DDG) or distillers dried grains with solubles (DDGS).
7. The process of any one of paragraphs 1 to 6, wherein the DDG or DDGS have an improved nutritional quality compared to DDG or DDGS recovered as a co-product of a process for producing a fermentation product in which the xylanase or enzyme blend comprising the xylanase is not present or added.
8. The process of paragraph 7, wherein the DDG or DDGS have increased fat content.
9. The process of any one of paragraph 1 to 8, wherein the true metabolizable energy of the DGS or DDGS is increased by at least 5%, at least 10%, at least 15%, or at least 20%, as compared to the TME of DGS or DDGS produced when a xylanase or enzyme blend comprising a xylanase is not present during the saccharification step, fermentation step, and/or simultaneous saccharification and fermentation step of the process.
10. The process according to paragraph 9, wherein the TME is for a monogastric animal.
11. The process according to paragraphs 9 or 10, wherein the DGS or DDGS produced are not darkened after drying as compared to DGS or DDGS produced when an enzyme blend according to any of paragraphs 1 to 9 is not present during the saccharification step, fermentation step, and/or simultaneous saccharification and fermentation step of a process according to any one of paragraphs 10 to 16.
12. The process of any of paragraphs 1 to 11, wherein the fermenting organism is yeast, particularly *Saccharomyces* sp., more particularly *Saccharomyces cerevisiae*.
13. The process of any one of paragraphs 1 to 12, wherein the enzyme blend further comprises a cellulolytic composition.
14. The process of any one of paragraphs 1 to 13, wherein the cellulolytic composition is present in the blend in a ratio of xylanase and cellulolytic composition from about 5:95 to about 95:5, such as from 5:95, 10:90, 20:80, 50:50, 80:20, 90:10, and 95:5.
15. The process of any one of paragraphs 1 to 14, wherein the xylanase is a GH30 family xylanase.
16. The process of any one of paragraphs 1 to 15, wherein the xylanase is a GH30_8 xylanase.
17. The process of any one of paragraphs 1 to 16, wherein the xylanase is a GH30_8 xylanase selected from the group consisting of:
   (i) the *Bacillus subtilis* xylanase of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto;
   (ii) the *Bacillus subtilis* xylanase of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto;
   (iii) the *Bacillus subtilis* xylanase of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto;
   (iv) the *Bacillus amyloliquefaciens* xylanase of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto;
   (v) the *Bacillus amyloliquefaciens* xylanase of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto;
   (vi) the *Bacillus licheniformis* xylanase of SEQ ID NO: 6 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto; and (vii) the *Paenibacillus pabuli* xylanase of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% amino acid sequence identity thereto.

18. The process of any one of paragraphs 1 to 17, wherein the cellulolytic composition comprises at least one, at least two, at least three, or at least four enzymes selected from the group consisting of:
   (i) a cellobiohydrolase I;
   (ii) a cellobiohydrolase II;
   (iii) a beta-glucosidase; and
   (iv) a GH61 polypeptide having cellulolytic enhancing activity.

19. The process of any one of paragraphs 1 to 18, wherein the cellulolytic composition comprises at least one, at least two, at least three, or at least four enzymes selected from the group consisting of:
   (i) an *Aspergillus fumigatus* cellobiohydrolase I;
   (ii) an *Aspergillus fumigatus* cellobiohydrolase II;
   (iii) an *Aspergillus fumigatus* beta-glucosidase; and
   (iv) a *Penicillium emersonii* GH61A polypeptide having cellulolytic enhancing activity.

20. The process of any one of paragraphs 1 to 19, wherein the cellulolytic composition comprises:
   (i) a cellobiohydrolase I comprising amino acids 27 to 532 of SEQ ID NO: 8 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 27 to 532 of SEQ ID NO: 8;
   (ii) a cellobiohydrolase II comprising amino acids 20 to 454 of SEQ ID NO: 9 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 20 to 454 of SEQ ID NO: 9;
   (iii) a beta-glucosidase comprising amino acids 20 to 863 of SEQ ID NO: 10 or a variant thereof having at least one substitution selected from the group consisting of F100D, S283G, N456E, and F512Y and at least 60%, at least 65%, at least 70%, at least 75%, at least 80%, at least 85%, at least 90%, at least 95%, at least 96%, at least 97%, at least 98%, or at least 99% sequence identity to amino acids 20 to 863 of SEQ ID NO: 10; and/or
   (iv) a GH61A polypeptide having cellulolytic enhancing activity comprising amino acids 26 to 253 of SEQ ID NO: 11 or a variant thereof having at least 60%, at least 65%, at least 70%, at least 75%, at least 80%, at least 85%, at least 90%, at least 95%, at least 96%, at least 97%, at least 98%, or at least 99% sequence identity to amino acids 26 to 253 of SEQ ID NO: 11.

21. The process of any one of paragraphs 1 to 20, wherein the cellulolytic composition further comprises an endoglucanase.

22. The process of any one of paragraphs 1 to 21, wherein the cellulolytic composition is derived from a strain selected from the group consisting of *Aspergillus*, *Penicilium*, *Talaromyces*, and *Trichoderma*, optionally wherein: (i) the *Aspergillus* strain is selected from the group consisting of *Aspergillus aurantiacus*, *Aspergillus niger* and *Aspergillus oryzae*; (ii) the *Penicilium* strain is selected from the group consisting of *Penicilium emersonii* and *Penicilium oxalicum*; (iii) the *Talaromyces* strain is selected from the group consisting of *Talaromyces aurantiacus* and *Talaromyces emersonii*; and (iv) the *Trichoderma* strain is *Trichoderma reesei*.

23. The process of any one of paragraphs 1 to 13, wherein the cellulolytic composition comprises a *Trichoderma reesei* cellulolytic composition.

24. Use of an enzyme blend according to any of paragraphs 1 to 23 for improving the nutritional quality of DGS or DDGS produced as a co-product of the fermentation product production process according to any of paragraphs 1 to 23, preferably without resulting in a darkening the DDG or DDGS.

25. Use of an enzyme blend according to any of paragraphs 1 to 23 for solubilizing fiber, preferably for solubilizing xylose and arabinose.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated herein by reference in their entireties. The present invention is further described by the following examples which should not be construed as limiting the scope of the invention.

Materials & Methods

Alpha-Amylase 369 (AA369): *Bacillus stearothermophilus* alpha-amylase with the mutations: I181*+G182*+N193F+V59A+Q89R+E129V+K177L+R179E+Q254S+M284V (SEQ ID NO: 12 herein) truncated to 491 amino acids.

Cellulolytic composition A: Cellulolytic composition derived from *Trichoderma reesei* comprising: *Aspergillus fumigatus* Cel7A CBHI disclosed as SEQ ID NO: 6 in WO2011/057140 and SEQ ID NO: 8 herein; *Aspergillus fumigatus* CBH II disclosed as SEQ ID NO: 18 in WO 2011/057140 and as SEQ ID NO: 9 herein; *Aspergillus fumigatus* beta-glucosidase (SEQ ID NO: 2 in WO 2005/047499 or SEQ ID NO: 10 herein) variant F100D, S283G, N456E, F512Y) disclosed in WO 2012/044915 or co-pending PCT application PCT/US11/054185; and GH61A polypeptide having cellulolytic enhancing activity derived from a strain of *Penicillium emersonii* (SEQ ID NO: 2 in WO 2011/041397 or SEQ ID NO: 11 herein).

Cellulolytic composition B: Cellulolytic composition derived from *Trichoderma reesei* comprising: *Aspergillus fumigatus* Cel7A CBHI disclosed as SEQ ID NO: 6 in WO2011/057140 and SEQ ID NO: 8 herein; and *Aspergillus fumigatus* beta-glucosidase (SEQ ID NO: 2 in WO 2005/047499 or SEQ ID NO: 10 herein) variant F100D, S283G, N456E, F512Y) disclosed in WO 2012/044915 or co-pending PCT application PCT/US11/054185).

E-SEP: Blend comprising transgenic GH10 xylanase expressing, and a GH62 arabinofuranosidase expressing *Trichoderma reesei* cellulose strain.

| # | Eluent |
|---|---|
| A | Water |
| B | NaOH 0.2M |
| C | Na-acetate 1M |
| D | Water |

Glucoamylase SA (GSA): Blend comprising *Talaromyces emersonii* glucoamylase disclosed as SEQ ID NO: 34 in WO99/28448, *Trametes cingulata* glucoamylase disclosed as SEQ ID NO: 2 in WO 06/69289, and *Rhizomucor pusillus* alpha-amylase with *Aspergillus niger* glucoamylase linker and starch binding domain (SBD) disclosed in SEQ ID NO: 26 herein having the following substitutions G128D+D143N (activity ratio in AGU: AGU: FAU-F is about 20:5:1).

Protease Pfu: Protease derived from *Pyrococcus furiosus* shown in SEQ ID NO: 13 herein.

Xylanase: GH30_8 xylanase from *Bacillus subtilis* having the amino acid sequence of SEQ ID NO: 1.

Yeast: ETHANOL RED™ available from Red Star/Lesaffre, USA.

HPLC Protocol

The HPLC Protocol in Table 1 below was used in Examples 2, 4, 5 and 6.

TABLE 1

| HPLC Protocol | |
|---|---|
| HPLC system: | Agilent's 1100/1200 series with Chemstation software. Degasser Quaternary Pump Auto-Sampler Column Compartment w/Heater Refractive Index Detector (RI) |
| Column: | Bio-Rad HPX-87H Ion Exclusion Column, 300 mm × 7.8 mm, part #125-0140 Bio-Rad guard cartridge cation H, part #125-0129, Holder part #125-0131 |
| Method: | 5 µM H$_2$SO$_4$ mobile phase Flow rate: 0.6 ml/min Column temperature: 65° C. RI detector temperature: 55° C. |

Eluent Gradient

The Eluent Gradient in Table 2 below was used in Examples 2, 4, 5 and 6.

TABLE 2

| Eluent Gradient | | | | | | |
|---|---|---|---|---|---|---|
| # | | | Eluent | | | |
| A | | | Water | | | |
| B | | | NaOH 0.2M | | | |
| C | | | Na-acetate 1M | | | |
| D | | | Water | | | |
| No | Time | Flow [ml/min] | % B | % C | % D | Curve |
| 1 | 0.000 | | Run | | | |
| 2 | 0.000 | 1.000 | 10.0 | 0.0 | 47.5 | 5 |
| 3 | 12.500 | 1.000 | 10.0 | 0.0 | 47.5 | 5 |
| 4 | 12.501 | 1.000 | 50.0 | 0.0 | 25.0 | 5 |
| 5 | 45.000 | 1.000 | 50.0 | 30.0 | 10.0 | 8 |
| 6 | 48.000 | 1.000 | 50.0 | 30.0 | 10.0 | 5 |
| 7 | 48.001 | 1.000 | 10.0 | 0.0 | 47.5 | 5 |
| 8 | New Row | | | | | |
| 9 | 65.000 | | Stop Run | | | |

Xylose Solubilization Assay

The activity of a xylanase variant towards defatted destra-ched Maize (DFDSM) is measured by High-Performance Anion-Exchange Chromatography with Pulsed Amperometric Detection (HPAE-PAD). 2% (w/w) DFDSM suspension is prepared in 100 mM sodium acetate, 5 mM CaCl$_2$), pH 5 and allowed to hydrate for 30 minutes at room temperature under gently stirring. After hydration, 200 µl substrate suspension was pipetted into a 96 well plate and mixed with 20 µl enzyme solution to obtain a final enzyme concentration of 20 PPM relative to substrate (20 µg enzyme/g substrate). The enzyme/substrate mixtures are left for hydrolysis in 2.5 hours at 40° C. under gently agitation (500 RPM) in a plate incubator (Biosan PST-100 HL). After enzymatic hydrolysis, the enzyme/substrate plates are centrifuged for 10 minutes at 3000 RPM and 50 µl supernatant (hydrolysate) is mixed with 100 µl 1.6 M HCl and transferred to 300 µl PCR tubes and left for acid hydrolysis for 40 minutes at 90° C. in a PCR machine. The purpose of the acid hydrolysis is to convert soluble polysaccharides, released by the xylanase variant, into mono-saccharides, which can be quantified using HPAE-PAD. Samples are neutralized with 125 µl 1.4 M NAOH after acid hydrolysis and mounted on the HPAE-PAD for mono-saccharide analysis (xylose, arabinose and glucose) (Dionex ICS-3000 using a CarboPac PA1 column). Appropriate calibration curves are made using mono-saccharides stock solutions which are subjected to the same procedure of acid hydrolysis as the samples. The percentage xylose solubilized is calculated according to the equation:

$$\% \text{ Xylose solubilized} = \frac{[\text{Xylose}] * V * MW}{Xxyl * Msub}$$

where [xylose] denotes the concentration of xylose in the supernatant measured by HPAE-PAD, V the volume of the sample, MW, the molecular weight of internal xylose in arabino-xylan (132 g/mol), Xxyl, the fraction of xylose in DFDSM (0.102) and Msub, the mass of DFDSM in the sample.

EXAMPLES

Example 1

Example 1 demonstrates the effectiveness of enzyme blends of the present invention comprising different ratios of Xylanase and Cellulolytic Composition A, as listed in the Materials & Methods section.

Approximately 5 g corn mash per tube was added. The mash was obtained from a commercial ethanol plant, and had been liquefied with a blend of AA369 and Protease Pfu. Suspended hydrated Ethanol Red yeast, GSA (0.6 AGU/g dry solids), and enzyme blends of the present invention or water, were dosed subsequently. The total dose of each enzyme blend tested was 100 µg/g dry solids.

After dosing, the tubes were capped with stoppers having a small hole, poked with a push pin, and vortexed before being placed in a 32° C. water bath for simultaneous saccharification and fermentation (SSF). The tubes were vortexed morning and afternoon during fermentation. After fermenting over three nights, the tubes were spun down 5 min. at 3000 RPM, and the supernatants were filtered through 0.45 µm syringe filters.

Figure 2:
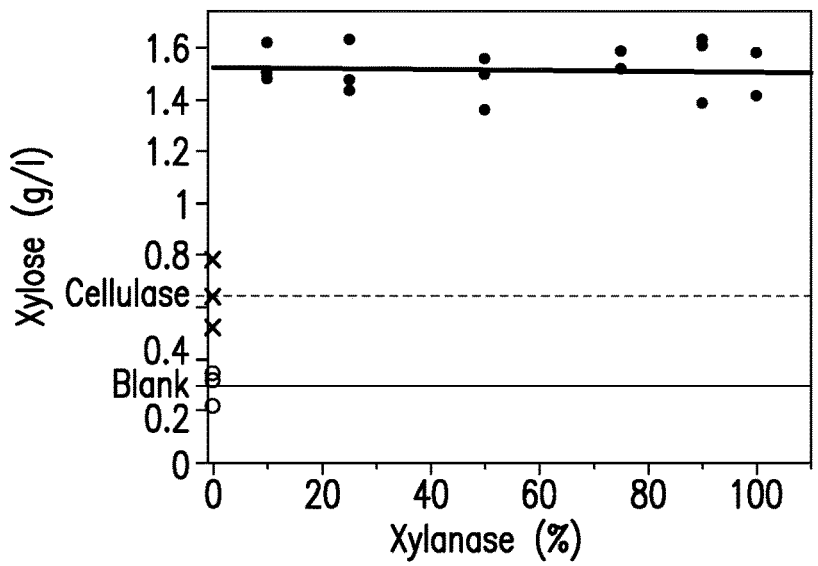
FIG. 2 shows solubilization of xylose using several enzyme blends of the present invention comprising different ratios of xylanase and a cellulolytic composition, and in particular shows significantly increased solubilization of arabinose when 10-100% of the cellulolytic composition in the enzyme blend is replaced by the xylanase as compared to solubilization of arabinose by the cellulolytic composition alone.

Acid hydrolysis was done in micro centrifuge tubes with screw caps. 600 µl sample and 200 µl 5N HCl was added, and they were placed in a heating block at 95° C. for 40 min. After cooling, they were neutralized with 200 µl NaOH (50% w/w NaOH, diluted 4×vol/vol). The purpose of the acid hydrolysis was to hydrolyze oligosaccharides to monosaccharides, to capture all solubilized sugars by the subsequent analytical assays. The hydrolyzed samples were diluted 100× on a Hamilton before being analyzed on a Dionex ICS-3000 HPAEC-PAD system with a CarboPac PA1 column. Data was analyzed with the JMP software package from SAS Institute. FIG. 1 and FIG. 2 show solubilization of arabinose and xylose, respectively, using an enzyme blends of the present invention comprising various ratios of the xylanase and the cellulolytic composition. FIG. 1 and FIG. 2 show significantly increased solubilization of arabinose and xylose when 10-100% of the cellulolytic composition in the enzyme blend is replaced by the xylanase as compared to solubilization of arabinose and xylose by the cellulolytic composition alone. Notably, there is no detectable difference between the solubilization of arabinose and xylose obtained with the different xylanase containing blends, indicating that the enzyme blends of the present invention are effective at solubilizing arabinose and xylose over a wide range of ratios of xylanase to cellulolytic composition present in the blend.

Example 2

Dose-response curves were obtained using three different enzyme blends of the present invention, for example blends of Xylanase and/or Cellulolytic Composition A. The data demonstrates that higher degrees of solubilisation of arabinose and xylose could be achieved when the cellulolytic composition was included in the blend, and that the performance of the blend could be optimized by adjusting xylanase: cellulolytic composition ratio.

About 5 g mash per tube was dosed by the "Glamdring" LEAP mash handling robot. Suspended hydrated yeast, GSA, and enzyme blend of the present invention dilutions were dosed on the Biomek liquid handler. SSF fermentations were run over three nights (64-72 hours) at 32° C. Mash from Red Trail Energy (RTE) was used.

After dosing, the tubes were capped with stoppers with a small hole, poked with a push pin, and vortexed before being placed in a 32° C. water bath. The tubes were vortexed morning and afternoon during fermentation. After fermenting over three nights, the tubes were spun down 5 min. at 3000 RPM, and the supernatants were filtered through 0.2 µm Spin-X filters.

Ethanol, sugars, glycerol, and acids were measured using the HPLC protocol from Table 1 above in the "Materials & Methods" section.

Acid hydrolysis was done in micro centrifuge tubes with screw caps. 300 µl sample and 100 µl 5N HCl was added, and they were placed in a heating block at 95° C. for 40 min. After cooling, they were neutralized with 100 µl NaOH (50% w/w NaOH, diluted 4×vol/vol). The purpose of the acid hydrolysis was to hydrolyze oligosaccharides to monosaccharides, to capture all solubilized sugars by the subsequent analytical assays.

The hydrolyzed and neutralized samples were diluted 100× on a Hamilton before HPAEC-PAD. A Dionex ICS-3000 system with a CarboPac PA1 column was used. The eluent gradient shown in Table 2 above in the "Materials & Methods" section was applied.

The column temperature was 30° C. Sample volume 5 µl. PAD waveform "Gold, Carbo, Quad".

Figure 3:
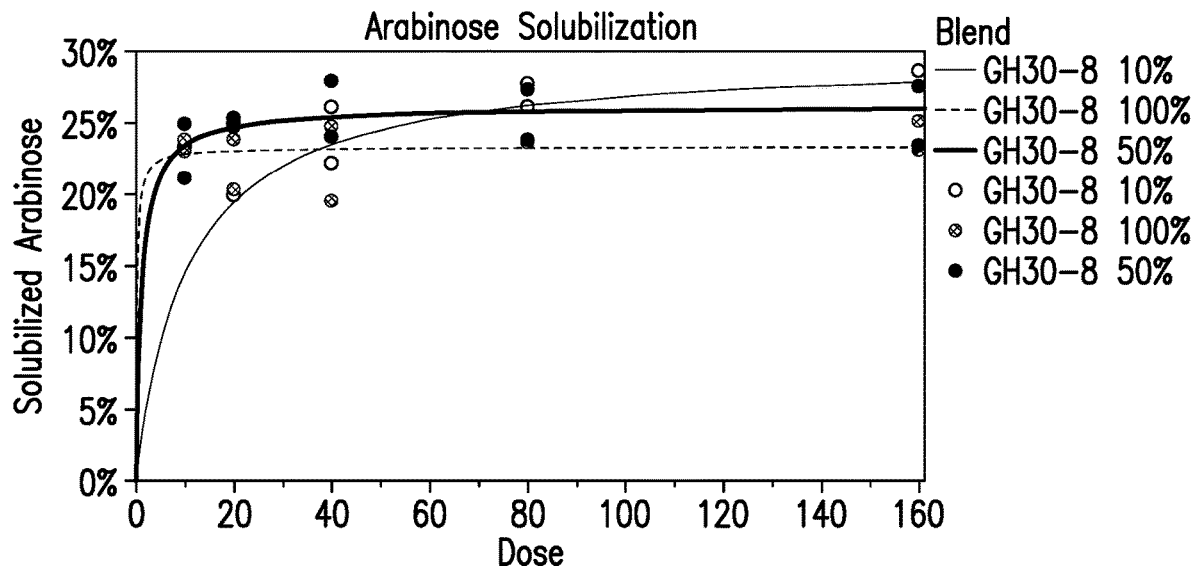
FIG. 3 shows the solubilisation of arabinose in response to increasing doses of several enzyme blends comprising different ratios of xylanase and a cellulolytic composition.
Figure 4:
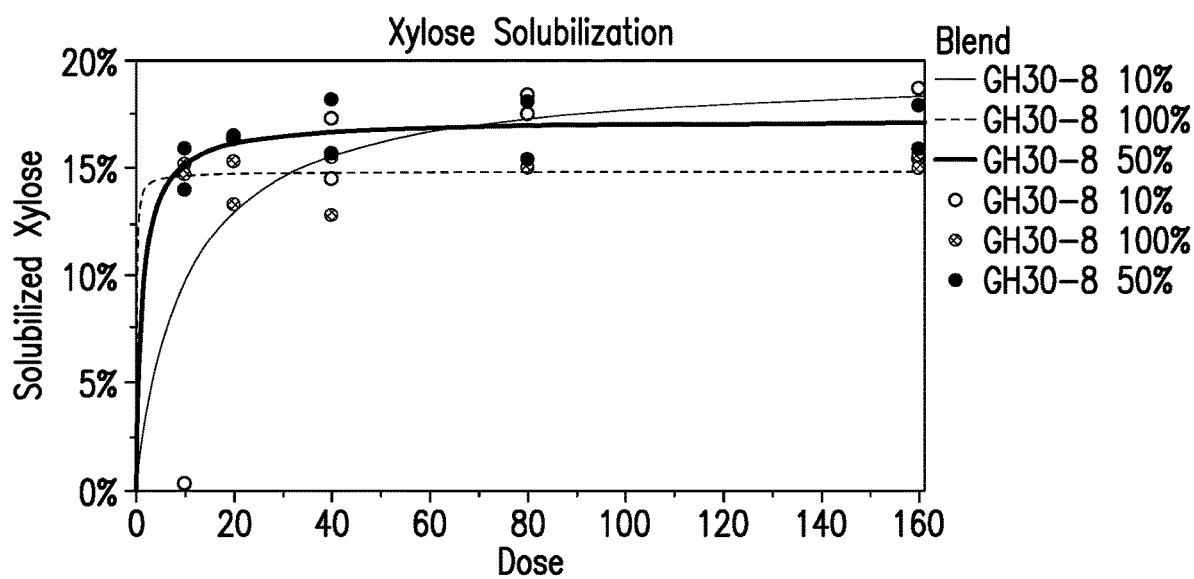
FIG. 4 shows the solubilisation of xylose in response to increasing doses of several enzyme blends comprising different ratios of xylanase and a cellulolytic composition.

FIG. 3 and FIG. 4 show the solubilisation of arabinose and xylose, respectively, in response to increasing doses of the enzyme blends of the present invention. The pattern was similar for arabinose and xylose solubilization. With the pure xylanase (100%), maximum solubilization was obtained at a dose of 10 µg EP/g DS, where the curve essentially flattens. For a blend comprising 50% xylanase and 50% cellulolytic composition, a higher conversion could be obtained, and maximum solubilization was essentially obtained at a dose of 40 µg total EP/g DS. For a blend comprising 10% xylanase and 90% cellulolytic composition, possibly an even higher maximum solubilization was possible for doses of 80 µg total EP/g DS and above. This data shows that the xylanase alone is effective at solubilizing arabinose and xylose, and that solubilization can be enhanced when including a cellulolytic composition and adjusting the xylanase: cellulolytic composition ratio.

Example 3

This example shows that DDGS produced with addition of an enzyme blend of the present invention comprising a 20:80 ratio of Xylanase:Cellulolytic Composition A increased the true metabolizable energy in an animal feed trial.

DDGS material produced in pilot plant was used for an animal feed trial. The feed trial was conducted at University of Georgia with non-cecectomized roosters as a 48-hour TME (true metabolizable energy) trial. The reported results are TMEn (nitrogen corrected) on a dry solid basis. Controls with only GSA were included as the baseline. 100 or 1000 µg enzyme protein per g dry solids was added of the enzyme blend of the present invention. The estimated TME increase was 12% (17% for a "mega dose").

Five pilot plant fermenters were filled with 8 kg of mash each. The mash was obtained from a commercial ethanol plant, and liquefied using a blend of AA369 and Protease Pfu and hydro heater. Before transferring to the fermenters, all of the mash was mixed well in a 50 kg mixing tank, pH was checked (5.07), and 50 ppm urea and 3 ppm penicillin was added.

The DDGS feed material was prepared as follows. The mash was transferred to plastic buckets placed on a scale, and transferred to the fermenters from here. Temperature was stabilized at or below 32° C. before enzymes and hydrated yeast were added. The heating was done by adding steam to the jacket, and the temperature was overshot to about 42° C. before being stabilized. The temperature during SSF had to be maintained by friction heat from the agitators, because the heat exchanger for warm water to the jackets was out of service in pilot plant. Therefore, temperatures were running low (~24-28° C.) during the first days, and eventually, the agitator speeds were increased to 600 RPM to maintain 32° C. Before harvest, the temperature was increased to 95° C. for 40 min. by steam injection, and aeration was set to 3 L/min. to evaporate off the ethanol. Agitation was set to 200 RPM. Then, water cooling was used to bring down the temperatures to under 50° C. before the fermenters were emptied. The material was transferred to 9×13" non-stick baking pans and placed in a vented oven at 50° C. After oven drying, the slightly moist material was ground in a food processor before being placed in a freeze dryer, and ground again after freeze drying. All the material was split on an 8-way sample splitter in the granulation building. Samples were shipped to Midwest for proximate analysis.

Taking averages of the treatments, the improvements in Table 3 below are estimated. This exceeds the set goal of 5% increase by a wide margin. Data for TMEn per dry weight was analyzed in JMP statistical software. Since there was a high batch-to batch variation of the prepared DDGS (relative to the variation among the eight individual birds that were fed the same batch), a one-way ANOVA model was fitted with the five DDGS batches being the explanatory variable; rather than nesting batch under treatment type.

TABLE 3

| Treatment | Average | Increase |
|---|---|---|
| Control | 3358 | 0% |
| 100 μg | 3758 | 12% |
| 1000 μg | 3917 | 17% |

TABLE 4

| | |
|---|---|
| RSquare | 0.9327 |
| RSquare Adj | 0.925 |
| Root Mean Square Error | 73.587 |
| Mean of Response | 3630.1 |
| Observations (or Sum Wgts) | 40 |

TABLE 5

Effect Tests

| Source | Nparm | DF | Sum of Squares | F Ratio | Prob > F |
|---|---|---|---|---|---|
| Batch | 4 | 4 | 2626463.8 | 121.2568 | <.0001* |

TABLE 6

Tukey HSD Multiple Comparison Test
$\alpha = 0.050\ Q = 2.87506$

| Level | | | | | Least Sq Mean |
|---|---|---|---|---|---|
| 1000 μg | A | | | | 3917 |
| 100 μg 1 | A | | | | 3830 |
| 100 μg 2 | | B | | | 3686 |
| Control 1 | | | C | | 3524 |
| Control 2 | | | | D | 3193 |

Levels not connected by same letter are significantly different.

It is seen from the Table 6 above that control #1 is significantly different from control #2, and 100 μg batch #1 is significantly different from 100 μg batch #2. Hence, the batch-to-batch variation was very high.

Figure 5:
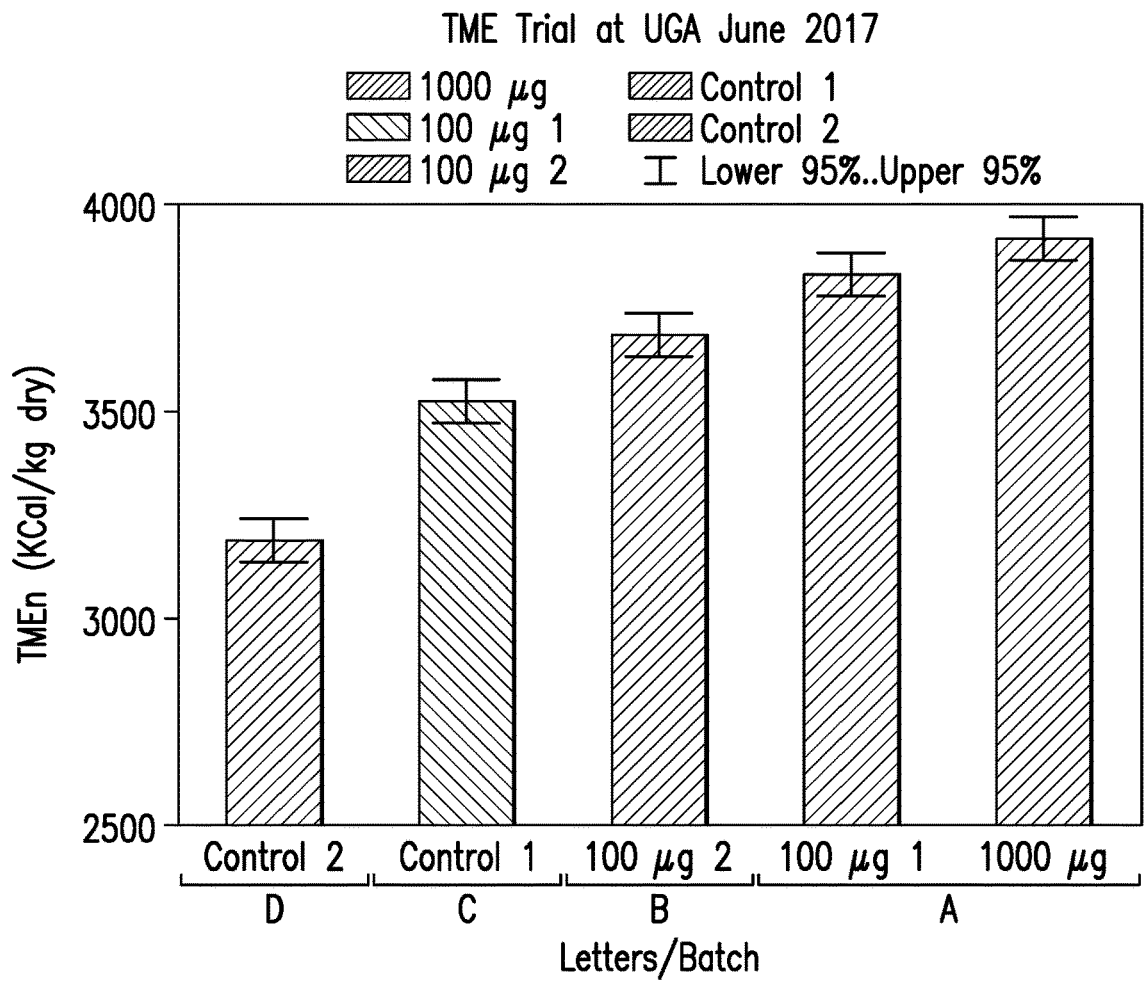
FIG. 5 shows a positive effect in feed trials on the true metabolizable energy (TME) values of distillers dried grains with solubles (DDGS) produced in accordance with a process for improving the nutritional quality of DDGS of the present invention.

Despite the high batch-to-batch variation, however, FIG. 5 shows that the enzymatic treatments had a positive effect on the TME values, as the ordering of the batches is such that the two controls had the lowest TME, and the 1000 μg "mega dose" had the highest TME.

Example 4

Example 4 demonstrates that when added to a raw starch SSF, an exemplary enzyme blend of the present invention comprising a 50:50 ratio of Xylanase:Cellulolytic Composition A solubilized similar amounts of fiber compared to previous tests using the enzyme blend on mash from a conventional cook process.

Materials
  Fine grind corn flour (IP free)
  Lactrol stock, 1 g/L
  Urea stock, 200 g/L
  Amylase enzyme product, BPX10.5c
  Cream Yeast
Equipment
  Moisture Analyzer
  Mixer/Paddle
  Beaker (for mixing corn slurry)
  PH meter
  Pipettes/Tips
  Serological Pipette, 100 ml with cut tip (a saw is used to cut the tip so corn slurry can be aliquoted). 125 mL Wheaton bottles and caps with holes drilled
  Heated Shaker
  Water bath
  Baffled flasks (250 mL)
  HPLC vials/caps
  0.2u syringe filters
  Volumetric flask (10 mL) for enzyme dilution
Procedure Using fine-ground flour and water, a slurry targeting 34.5% dry solids (DS) was prepared. Using the Moisture Analyzer, the dry solids of corn flour determined to be 84.54%. The corn slurry was supplemented with 1000 ppm urea and 3 ppm Lactrol. The slurry was adjusted to pH 4.5 with 40% $H_2SO4$, allowed to mix for about an hour and then adjusted again to pH 4.5.

Approximately 70 g of corn mash was aliquoted into pre-weighed 125 mL Wheaton bottles using the serological pipette with cut tip. The bottles were covered with caps having drilled holes. The mash weight for each bottle was recorded. Corn slurry was added to a baffled flask (~5g corn slurry/treatment) for propagation treatments. The propagation flask size was chosen based on the slurry volume required for treatments, the flask is typically 5× the slurry volume. Only one propagation was done for the trial.

Enzyme dosages were based on the weight of corn slurry in each bottle. Water was dosed into each fermentation sample such that the volume correction brings all bottles in the experiment to the same total percent solids, making ethanol concentrations directly comparable between treatments. The enzyme doses in Table 7 were added.

TABLE 7

| BPX10.5c AGU/g DS | VD μg EP/g DS | GH30_8 μg EP/g DS | MGProt III mPROT(B)/g DS |
|---|---|---|---|
| 0.25 | 0 | 0 | 0 |
| 0.25 | 50 | 50 | 0 |
| 0.25 | 50 | 50 | 25 |

MBLA855 cream yeast (as described in WO2017/087330) was used. The propagation was run for 6 hours at 32° C. shaking at 150 rpm. The propagation was used to dose the fermentations. The fermentation mash was dosed so that the propagation made up 5% of the total fermentation mash. For fermentations, the typical 90° F. temperature staging can be found in Table 8.

TABLE 8

| Time (hours) | Temp (° F.) | Temp (° C.) | Time & Day |
|---|---|---|---|
| 0 to 16 | 90 | 32.2 | Mon 4-Tues 8 |
| 16 to 24 | 88 | 31.1 | Tues 8-Tues 4 |
| 24 to 48 | 87 | 30.6 | Tues 4-Weds 4 |
| 48 to 88 | 86 | 30 | Weds 4-Fri 8 |

After dosing, fermentations were swirled and placed in the water bath. The water in the bath was at the same level as the mash in the bottles to minimize evaporation. All bottles were swirled twice a day; morning and evening.

Samples were prepared for HPLC as follows. 5 ml sample was transferred to a tube, and centrifuged for 10 min. at 3000 g, then filtered through a 0.2 μm syringe filter. 1 ml sample was transferred to a HPLC vial and 20 μl of 40% $H_2SO_4$ was added. The vials were subsequently vortexed. Samples were stored at 4° C. To analyze the samples, the HPLC protocol from Table 1 above in the "Materials & Methods" section was used.

The method quantifies analytes using calibration standards for dextrins (DP4+), maltotriose, maltose, glucose, fructose, acetic acid, lactic acid, glycerol and ethanol. A 4-point calibration including the origin is used. The 18-minute Fuel method was used.

The solubilization assay was run as follows. Acid hydrolysis was done in micro centrifuge tubes with screw caps. 180 μl sample and 60 μl 5N HCl was added, and they were placed in a shaking heating block at 95° C. for 40 min. After cooling, they were neutralized with 60 μl NaOH (50% w/w NaOH, diluted 4×vol/vol). The purpose of the acid hydrolysis was to hydrolyze oligosaccharides to monosaccharides, to capture all solubilized sugars by the subsequent analytical assays.

The samples were diluted 100× on a Hamilton before HPAEC-PAD. A Dionex ICS-3000 system with a CarboPac PA1 column was used.

The eluent gradient shown in Table 2 above in the "Materials & Methods" section was applied.

The column temperature was 30° C. Sample volume 5 μl. PAD waveform "Gold, Carbo, Quad".

Results

Figure 6:
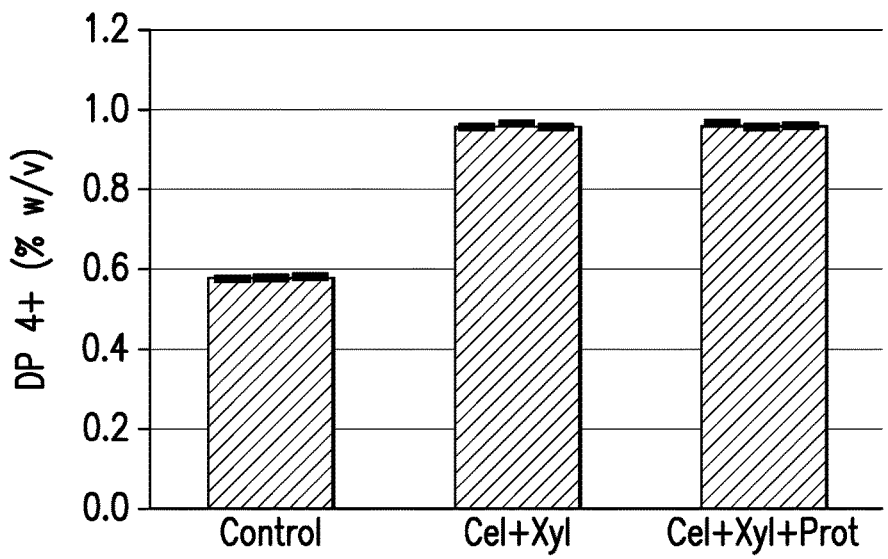
FIG. 6 shows the results of HPLC data demonstrating that the enzyme blends of the present invention increase the amount of solubilized sugars, as evidenced by the increased DP4+ peak.
Figure 7:
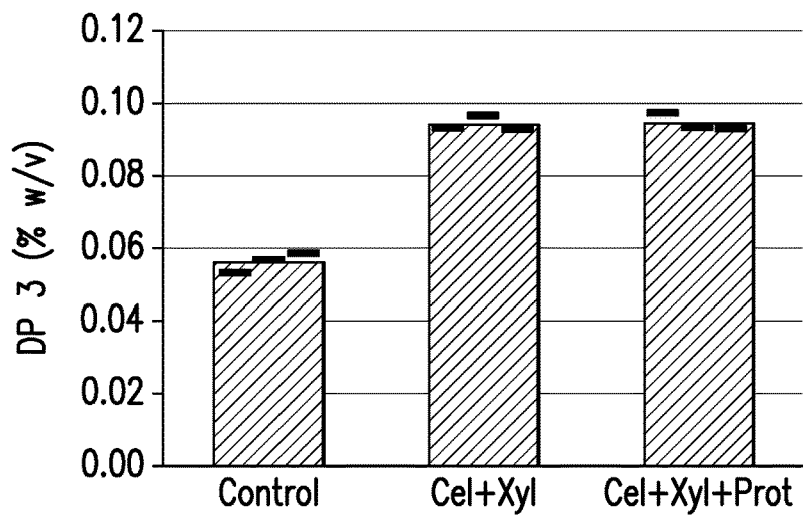
FIG. 7 shows the results of HPLC data demonstrating that the enzyme blends of the present invention increase the amount of solubilized sugars, as evidenced by the increased DP3 peak.

The HPLC data showed that the enzyme blend of the present invention increased the amount of solubilized sugars, as evidenced by increased DP4+ (FIG. 6) and DP3 peaks (FIG. 7).

Figure 8:
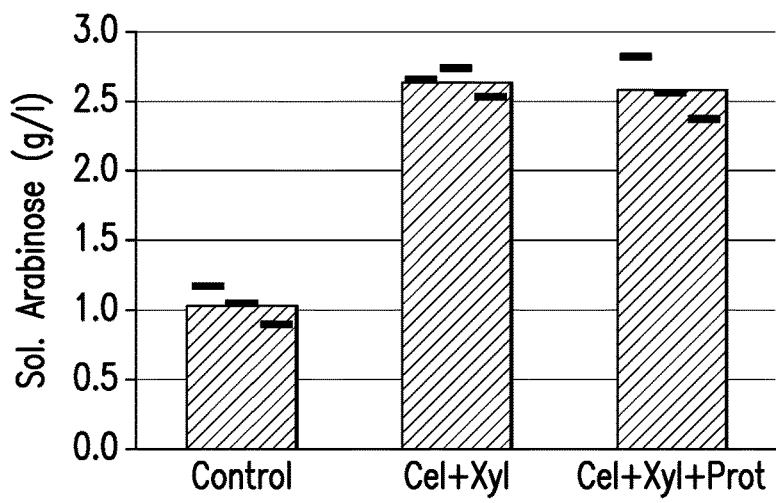
FIG. 8, FIG. 9 and FIG. 10 show the results of IC data using the enzyme blends of the present invention in a raw starch hydrolysis (RSH) process, demonstrating solubilization of sugars (e.g., arabinose (FIG. 8), xylose (FIG. 9) and galactose (FIG. 10)) on the same level as for a conventional cook process.
Figure 9:
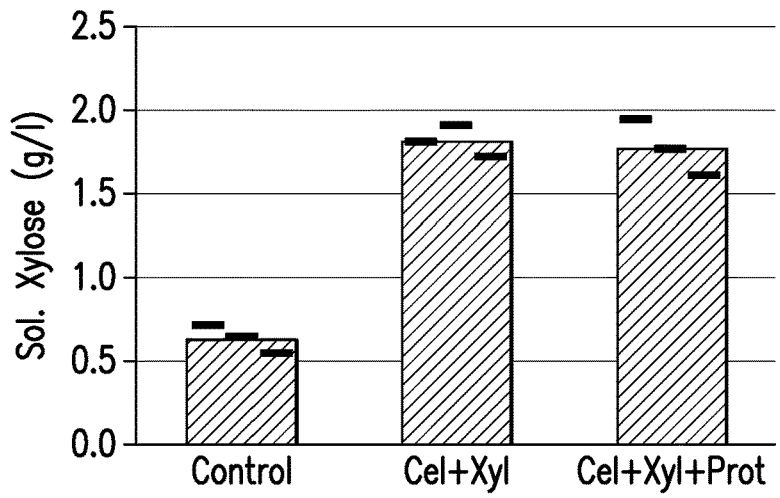
Figure 10:
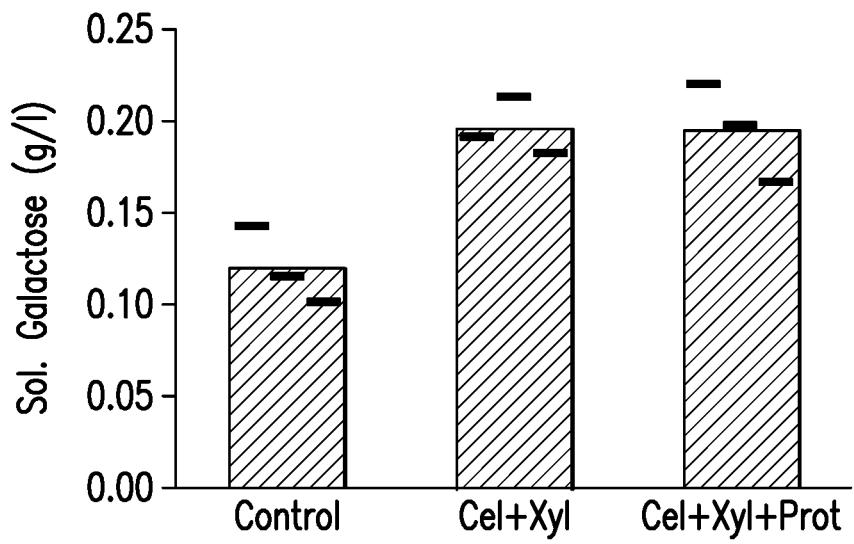

IC data showed solubilization of sugars (e.g., arabinose (FIG. 8), xylose (FIG. 9) and galactose (FIG. 10)) on the same level as for a conventional cook process.

Figure 11:
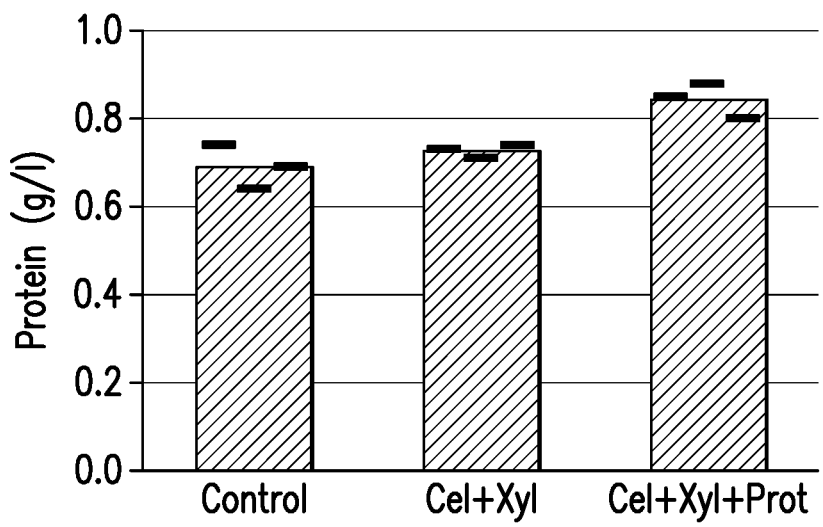
FIG. 11 shows the results of LECO data demonstrating that the use of a protease in combination with the enzyme blends of the present invention increased protein solubilisation.

LECO data showed that the protease increased protein solubilisation (FIG. 11).

Example 5

SSF fermentations with commercial corn mash, liquefied with a blend of AA369 and Protease Pfu, were carried out. After fermentation, the backend process was simulated, producing syrup and DDGS from the stillage. Ethanol Red yeast and 0.6 AGU/g DS of GSA was used together with the enzyme/blend additions shown in Table 9.

TABLE 9

| Samples | Enzymes added |
|---|---|
| Controls | no hemicellulases and cellulases were added. |
| 100 μg EP/g DS of E-SEP | Blend of GH10 xylanase and GH-62 arabinofuranosidase expressing *Trichoderma reesei* cellulase strains |
| 100 μg EP/g DS of Enzyme Blend 1 | Enzyme blend comprising 10:90 Xylanase: Cellulolytic Composition A |
| 100 μg EP/g DS of Enzyme Blend 2 | Enzyme blend comprising 20:80 Xylanase: Cellulolytic Composition A |
| 100 μg EP/g DS of Enzyme Blend 3 | Enzyme blend comprising 50:50 Xylanase: Cellulolytic Composition A |
| 1000 μg EP/g DS of Enzyme Blend 2 (Mega dose) | Enzyme blend comprising 20:80 Xylanase: Cellulolytic Composition A |

Figure 12:
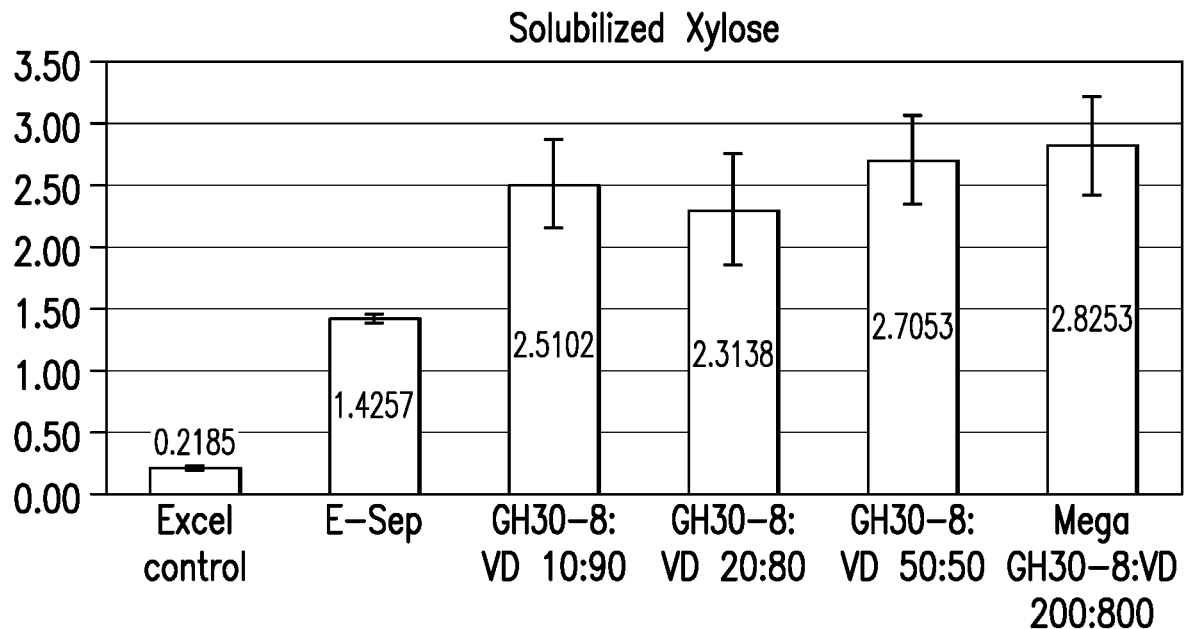
FIG. 12, FIG. 13, and FIG. 14 show that all enzyme blends of the present invention which were tested resulted in significantly higher levels of solubilized xylose (FIG. 12), arabinose (FIG. 13), and galactose (FIG. 14), as compared to the controls.
Figure 13:
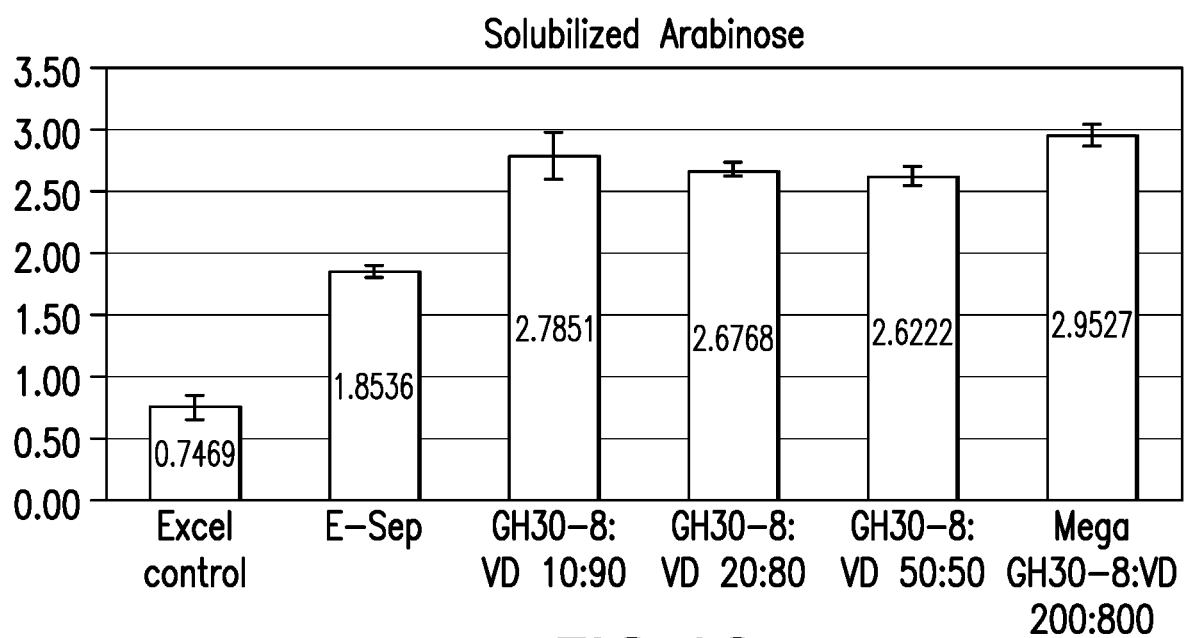
Figure 14:
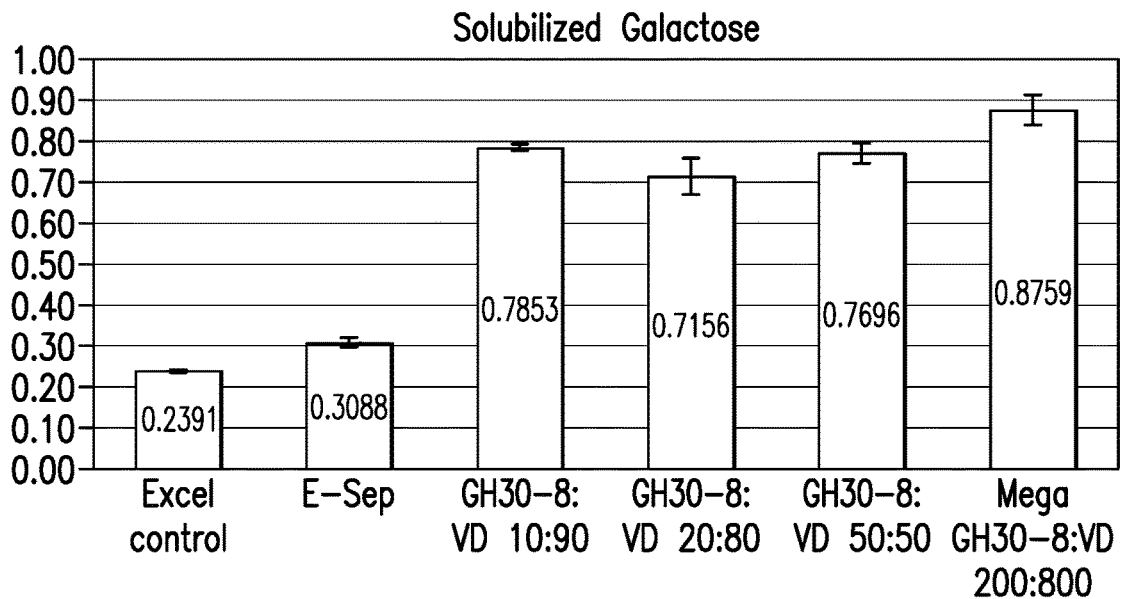

There were significantly higher levels of solubilized xylose (FIG. 12), arabinose (FIG. 13), and galactose (FIG. 14) obtained using all tested enzyme blends of the present invention as compared to the controls and E-SEP samples. There was, however, no significant difference between the blends comprising different xylanase: cellulolytic composition ratios. Even the mega dose was not significantly higher in sugar solubilization than 10% xylanase.

E-SEP treated samples produced the darkest DDGS. Unexpectedly, the enzyme blends of the present invention, at all doses tested, including the mega dose, showed no DDGS darkening versus the control.

Figure 15:
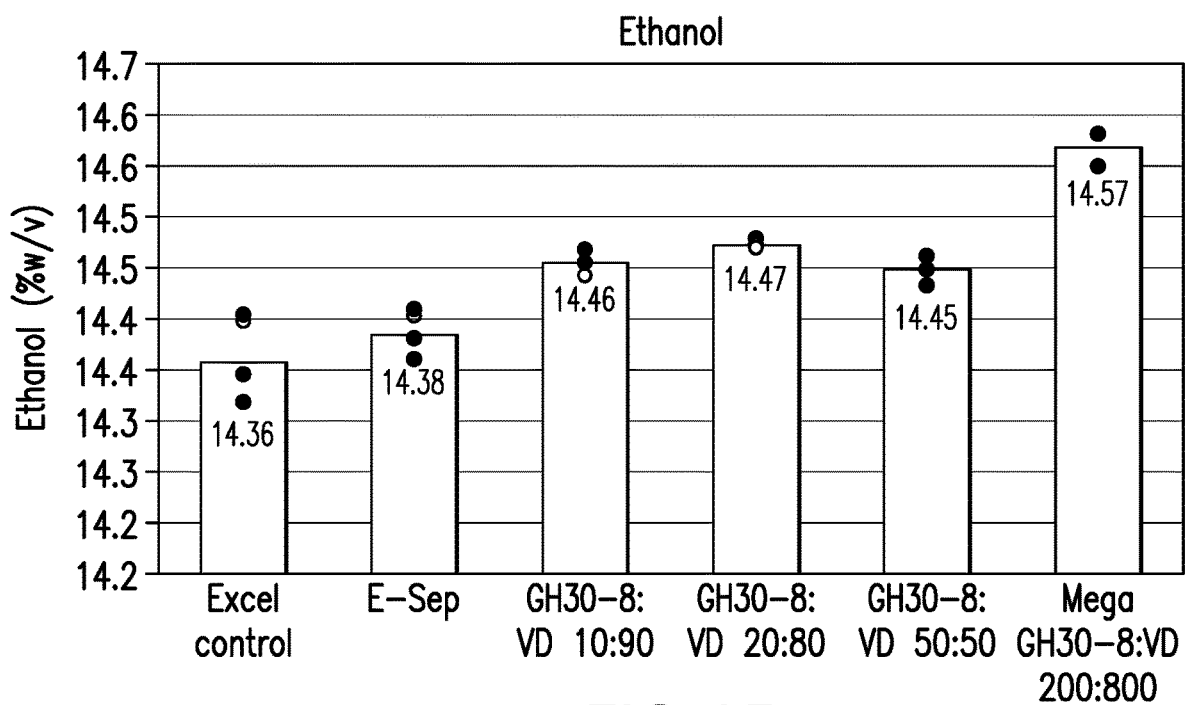
FIG. 15 shows that the enzyme blends of the present invention produced greater amounts of ethanol compared to the control with no significant differences between the amount of ethanol increased across the different enzyme blends, except mega dosing of one enzyme blend produced a significantly greater amount of ethanol compared the other enzyme blends tested.

FIG. 15 demonstrates that the enzyme blends of the present invention produced greater amounts of ethanol than the control with no significant differences between the 10%, 20%, or 50% xylanase: cellulolytic enzyme blends. The mega dose of 1,000 μg of the enzyme blend of the present invention had significantly higher ethanol than all other treatments.

Total solids of each treatment were measured on a moisture balance (120° C.) after thin stillage was evaporated to syrup. Samples were saved to compare color of syrup as an indicator of color of final DDGS.

Figure 16:
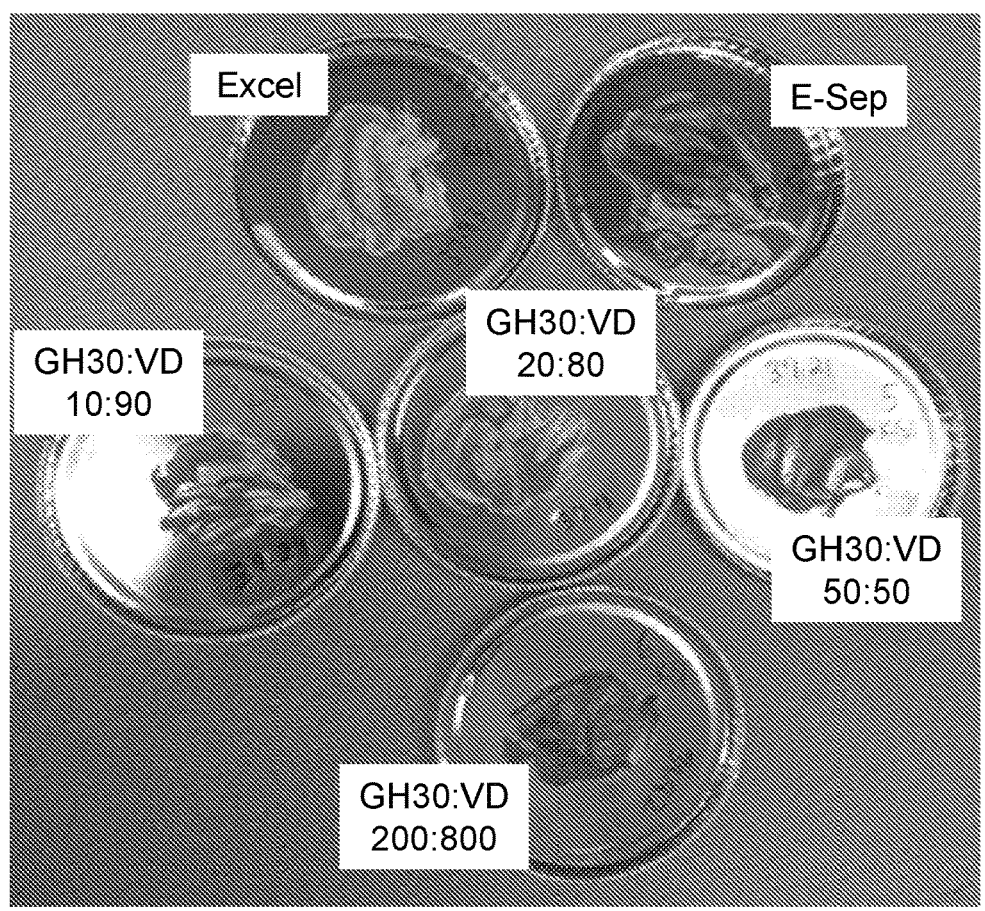
FIG. 16 shows a comparison of the color of syrup samples produced in accordance with a process of the present invention using different enzyme blends of the present invention compared to controls (E-Sep and Excel). In order from top left to bottom right, the samples shown are Excel (#1), E-Sep (#2), GH30: VD 10:90 (#3), GH30: VD 20:80 (#4), GH30: VD 50:50 (#5) and GH30: VD 200:800 (#6).

All syrups above were around 37-39% DS. As expected, E-SEP treatment containing GH10 xylanase and GH-62 arabinofuranosidase was the darkest due to the monomeric sugars generated (FIG. 16). Unexpectedly, no significant differences were seen in the three enzyme blends of the present invention and they were similar in color to the Excel control (FIG. 16). The mega dose appeared to slightly increase syrup color (FIG. 16).

Figure 17:
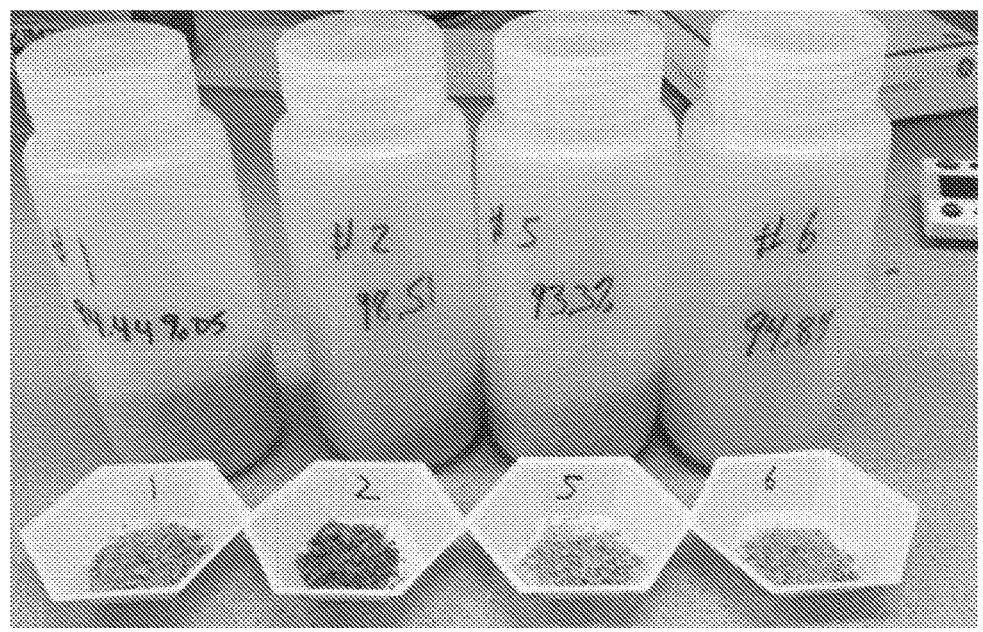
FIG. 17 shows DDGS samples produced in accordance with a process of the present invention using different doses of enzyme blends of the present invention (#5 and #6 from FIG. 16) compared to controls (Excel and E-Sep (#1 and #2, respectively, from FIG. 16)).

After syrup analyses, syrup and wet cake were combined and allowed to sit at refrigeration temperatures a few days to allow even moisture migration. Each treatment was then dried at 95° C. for approximately 2 hours until 90-95% DS was achieved in the DDGS (FIG. 17). DDGS color was measured on a Hunter Lab color scanner.

Figure 18:
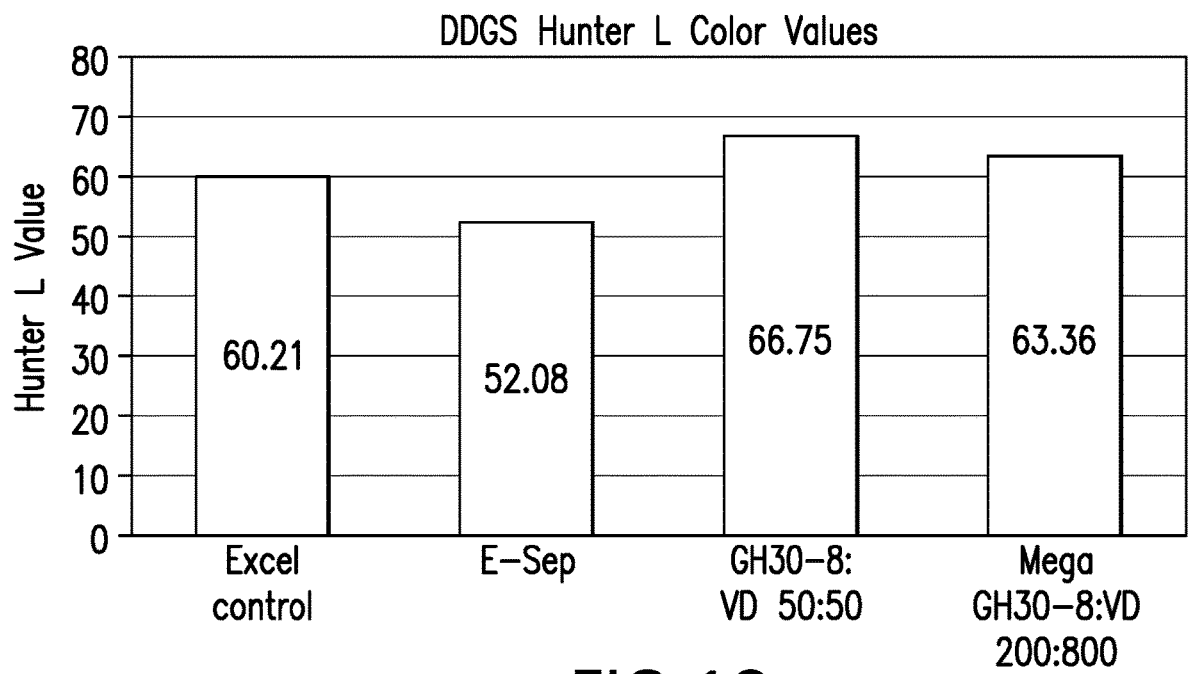
FIG. 18 shows the Hunter L Color values of DDGS samples produced in accordance with a process of the present invention using different doses of enzyme blends of the present invention compared to controls (Excel and E-Sep (#1 and #2, respectively, from FIG. 16 and FIG. 17)).
Figure 19:
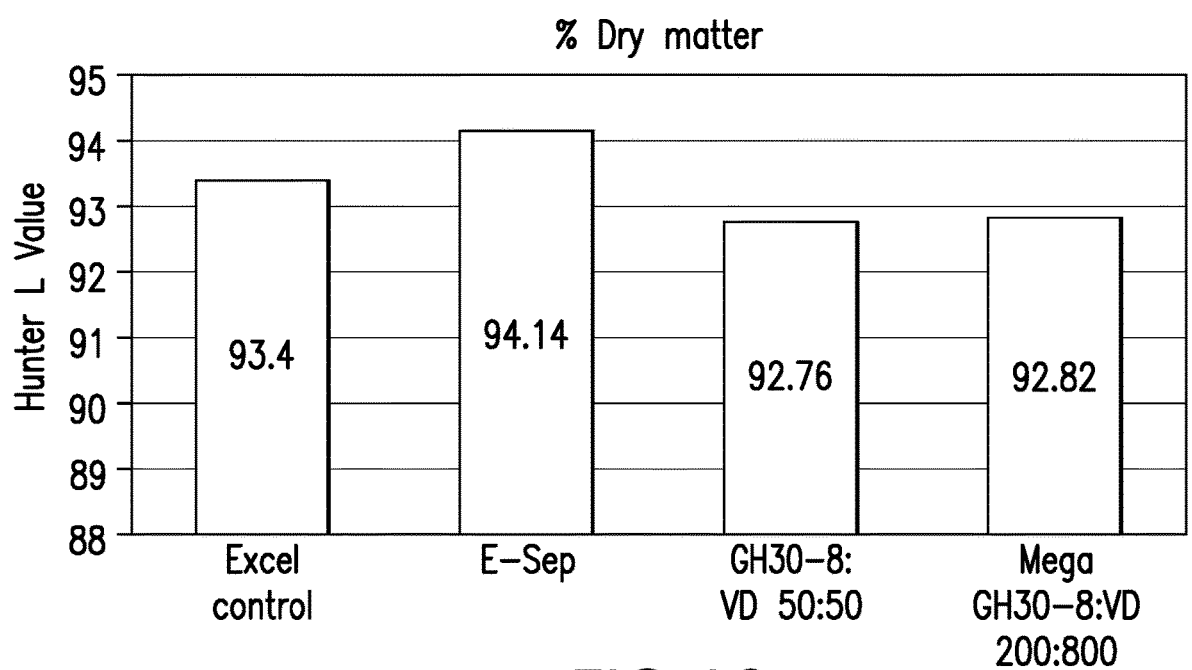
FIG. 19 shows the percentage of dry matter present in each of the samples shown in FIG. 17 after drying.
Figure 20:
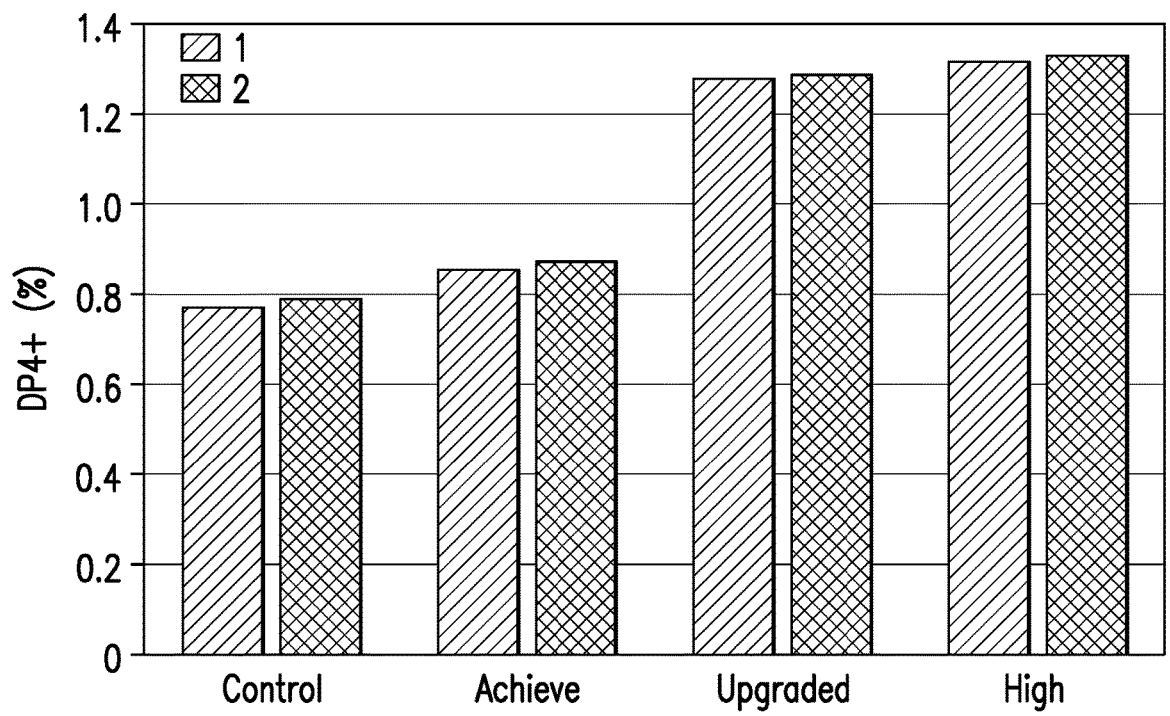
FIG. 20, FIG. 21, FIG. 22, FIG. 23, FIG. 24, FIG. 25, FIG. 26, FIG. 27, and FIG. 28 are graphs showing the HPLC results from the experiments in Example 6, including respectively data for DP4+ (FIG. 20), DP3 (FIG. 21), DP2 (FIG. 22), Glucose (FIG. 23), Fructose (FIG. 24), Lactate (FIG. 25), Glycerol (FIG. 26), Acetate (FIG. 27), and Ethanol (FIG. 28).
Figure 21:
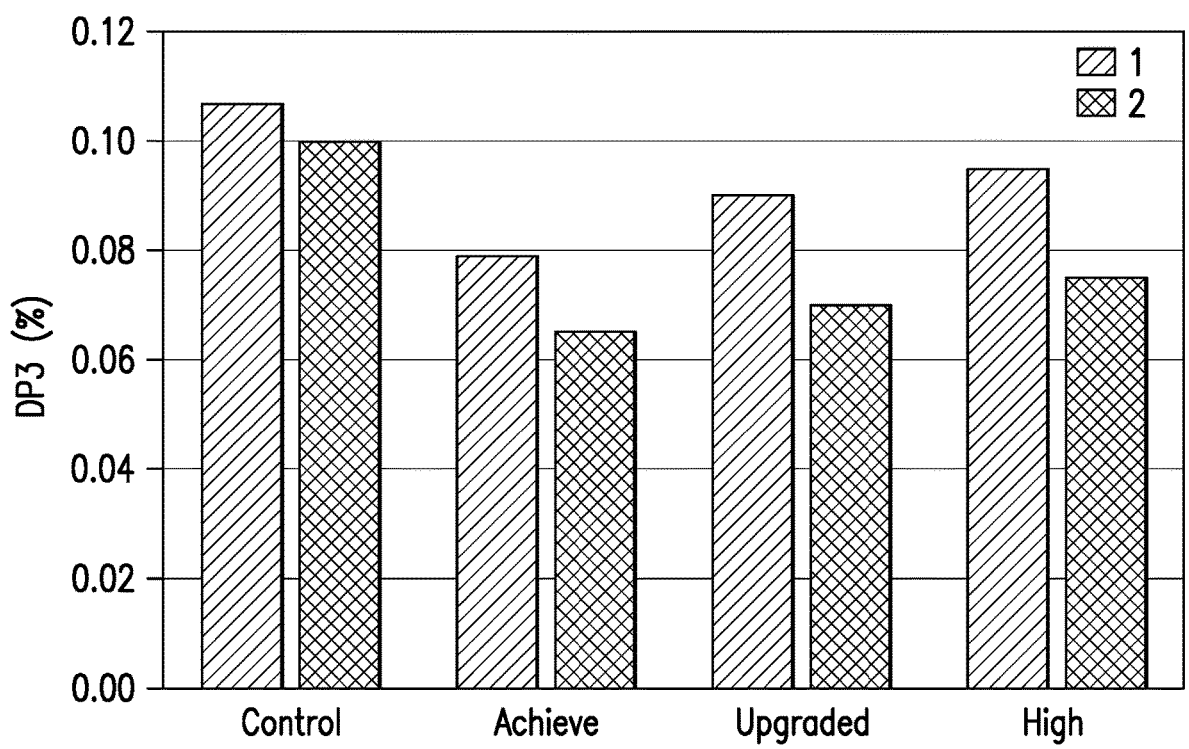
Figure 22:
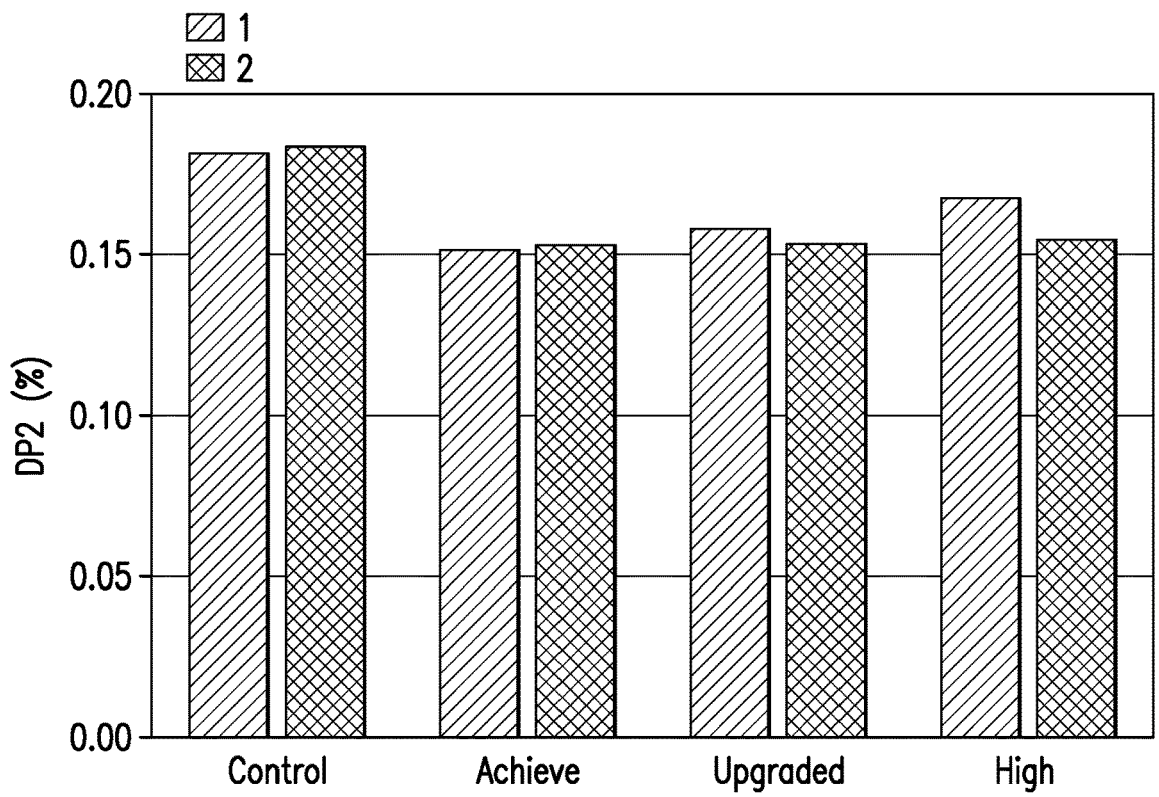
Figure 23:
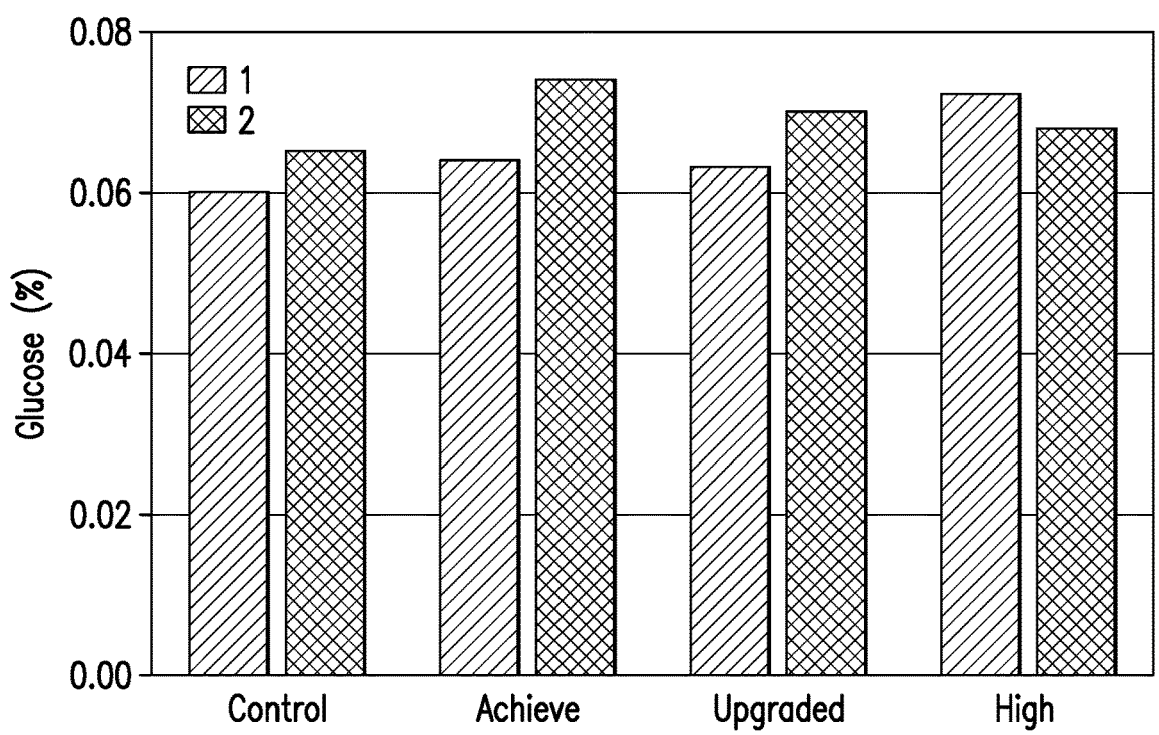
Figure 24:
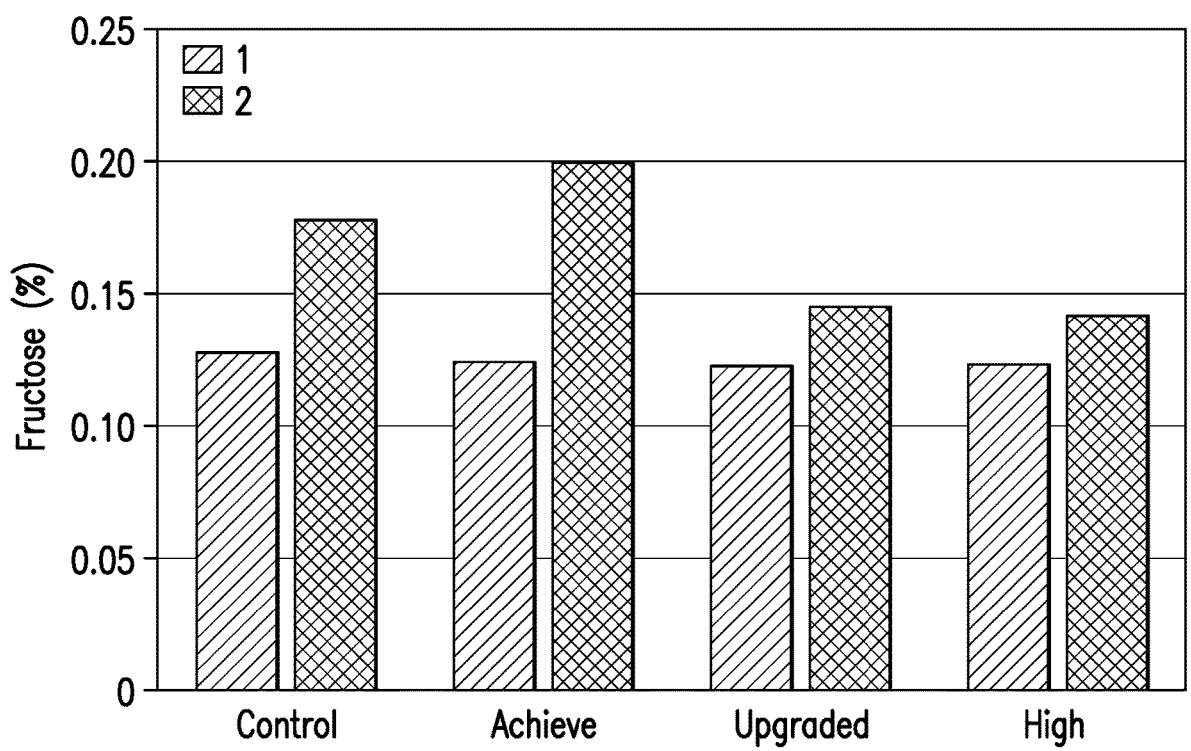
Figure 25:
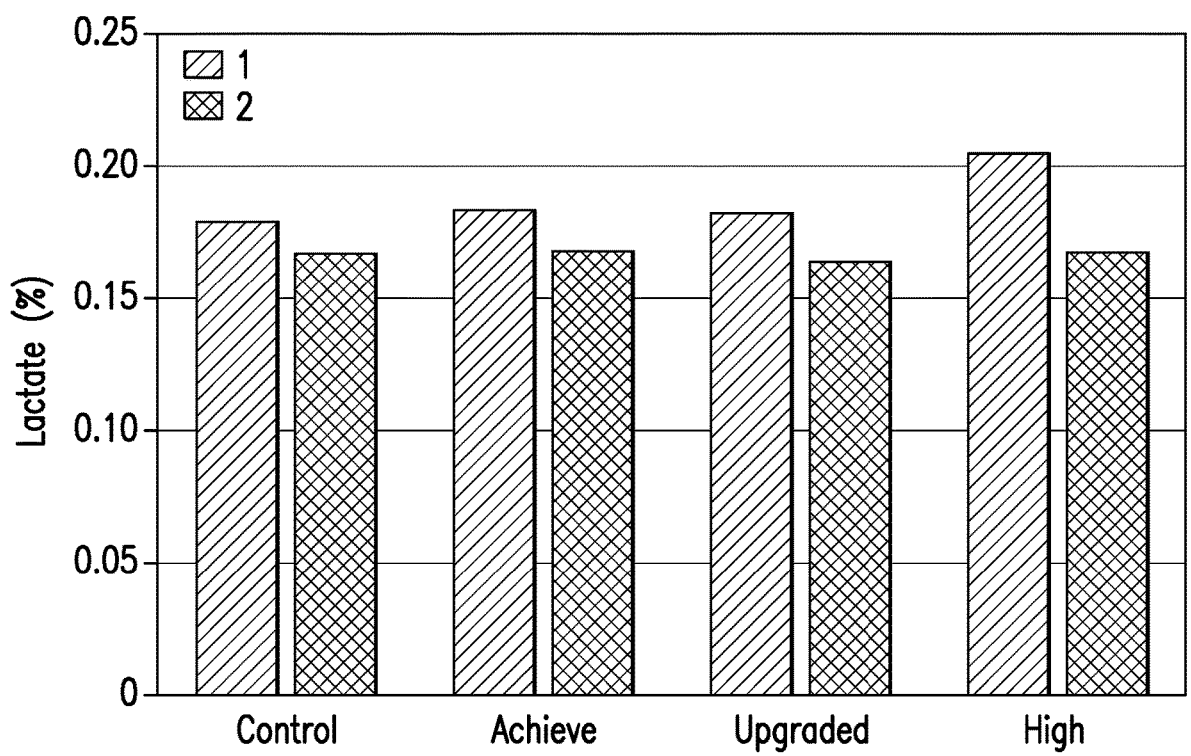
Figure 26:
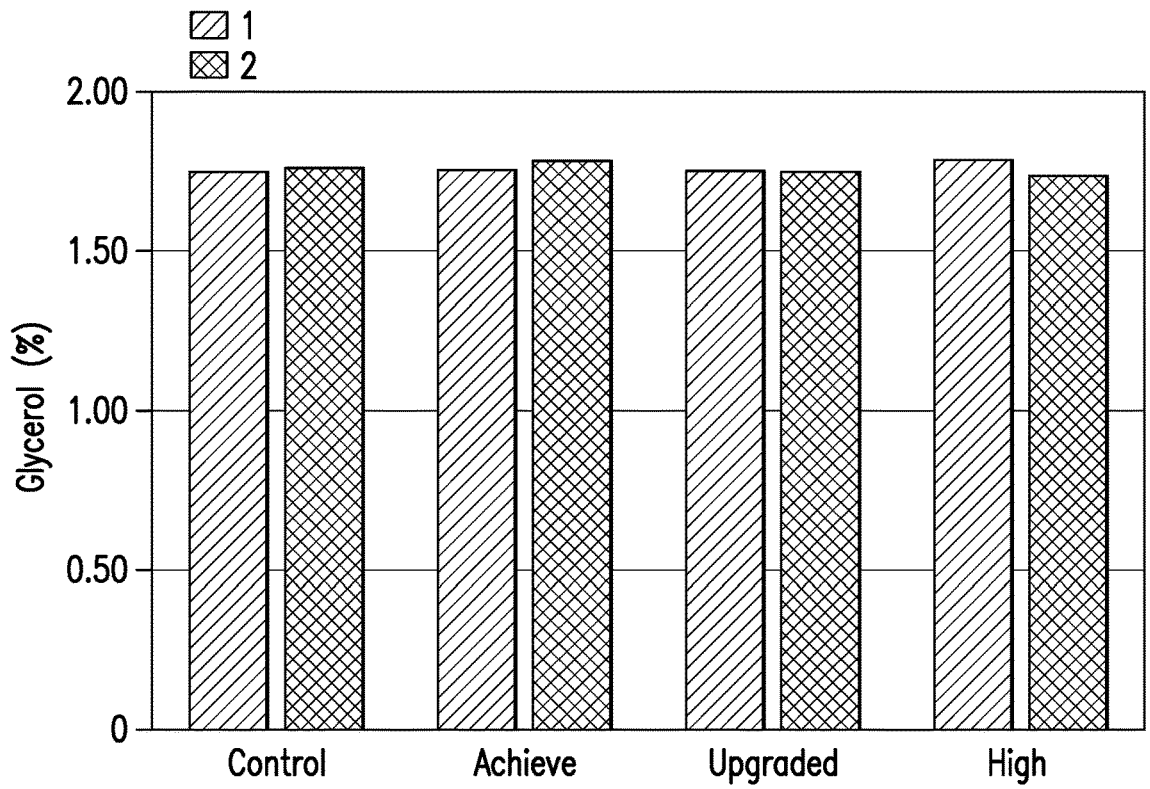
Figure 27:
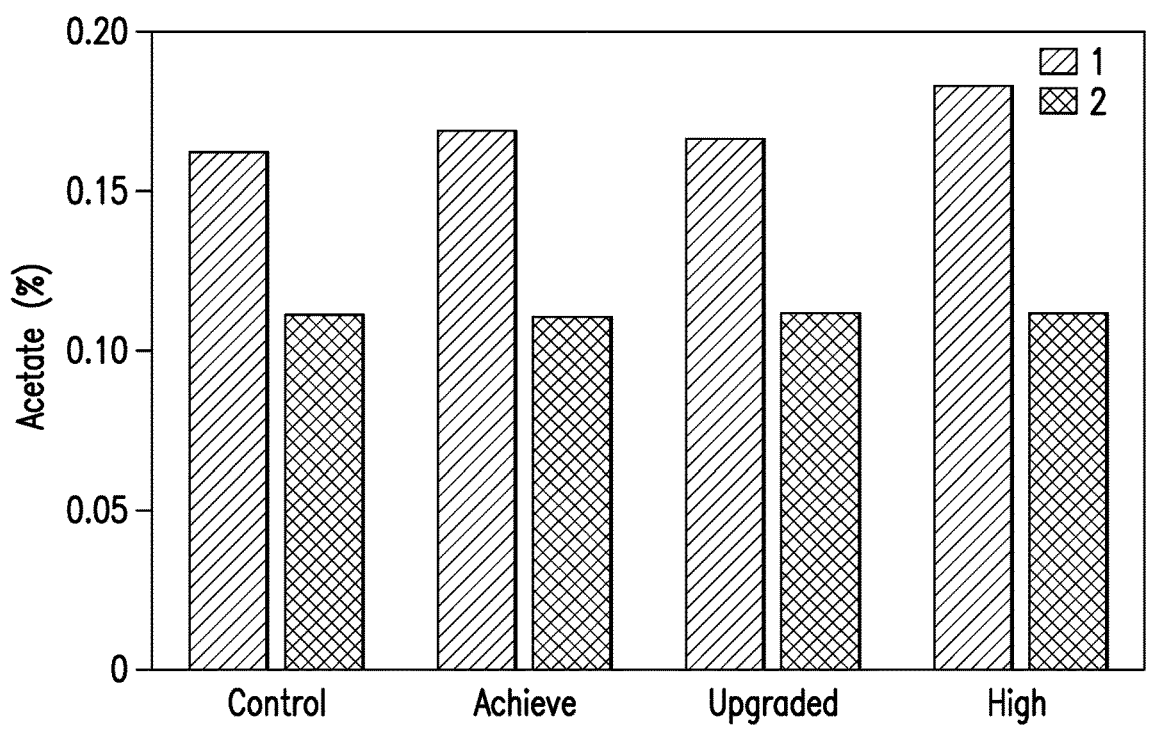
Figure 28:
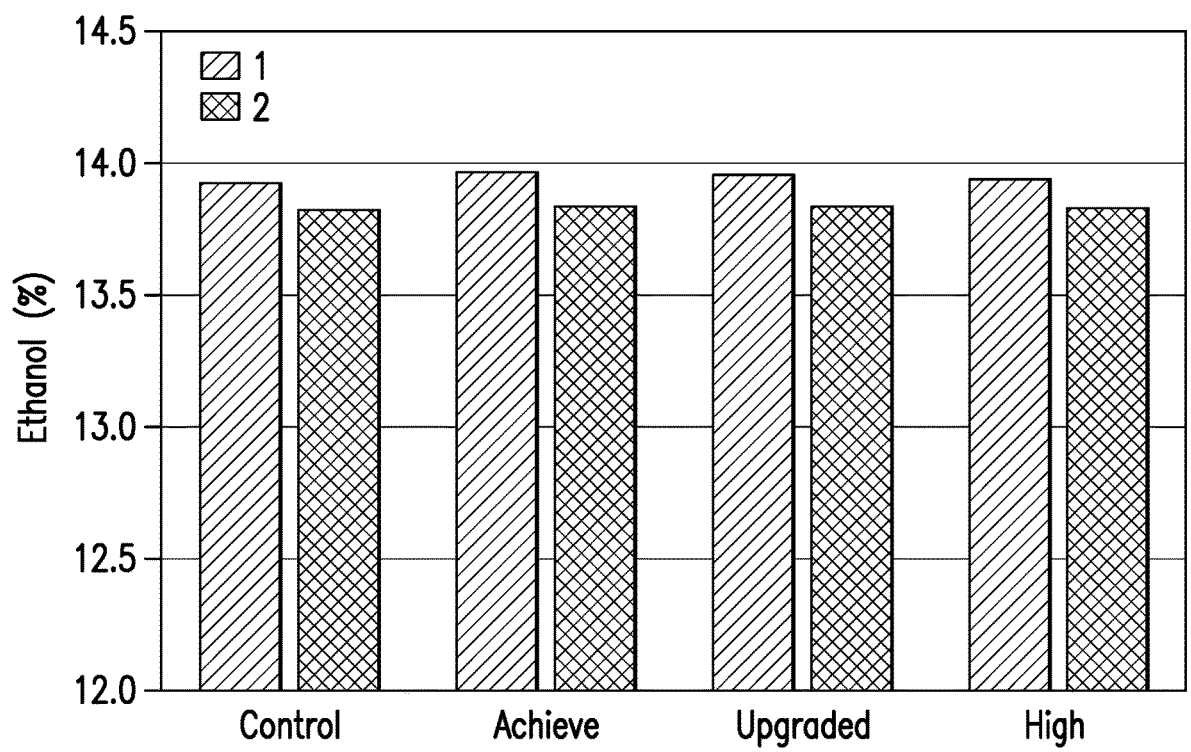
Figure 29:
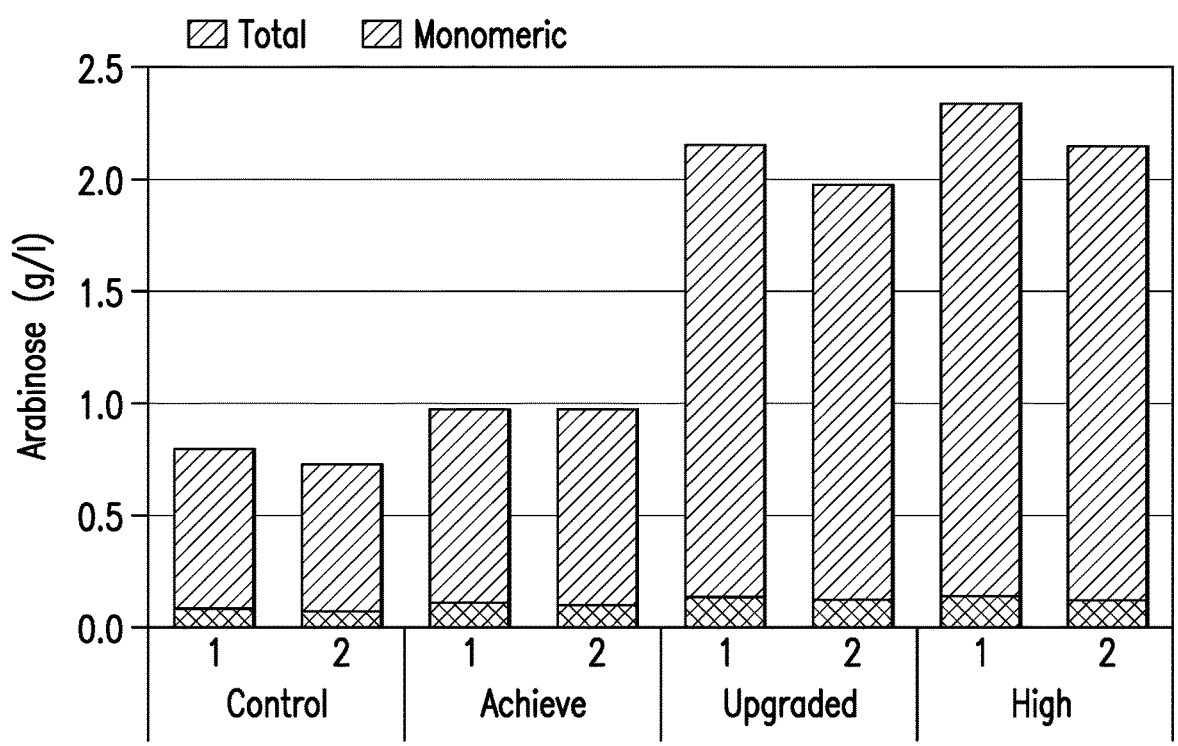
FIG. 29, FIG. 30, FIG. 31 and FIG. 32 are graphs showing total and monomeric solubilized sugars using various enzyme blends according to the present invention, including for example Arabinose (FIG. 29), Xylose (FIG. 30), Galactose (FIG. 31), and Glucose (FIG. 32).
Figure 30:
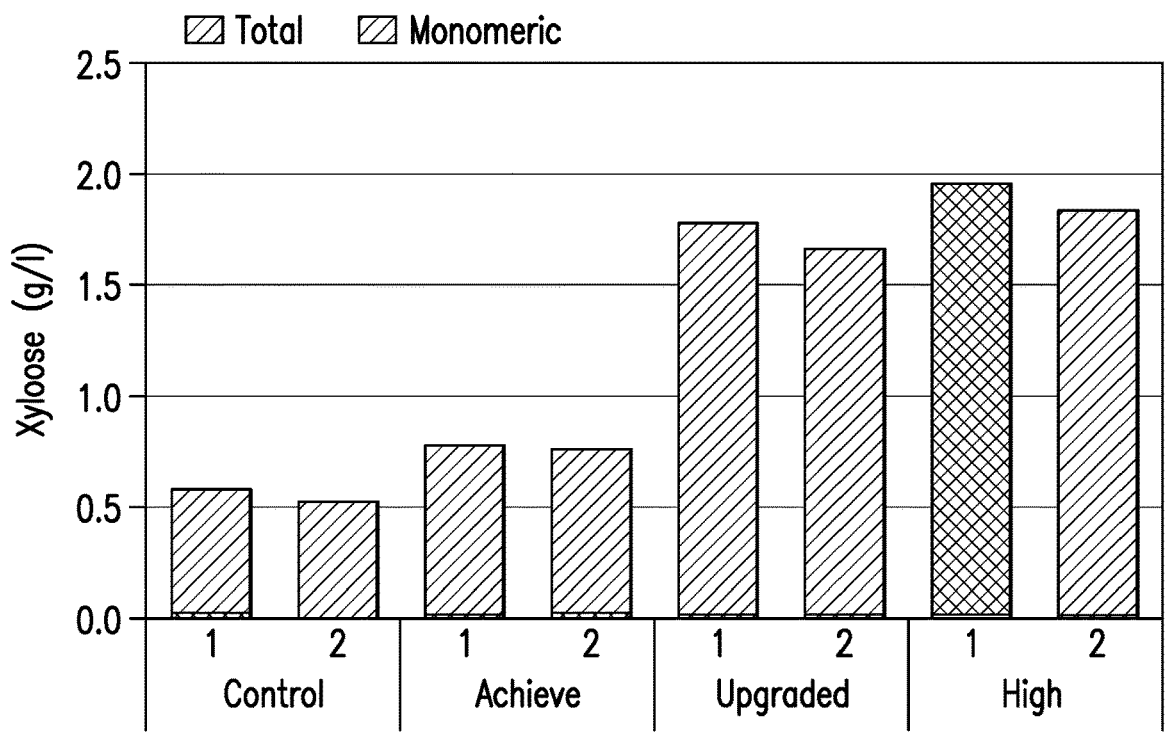
Figure 31:
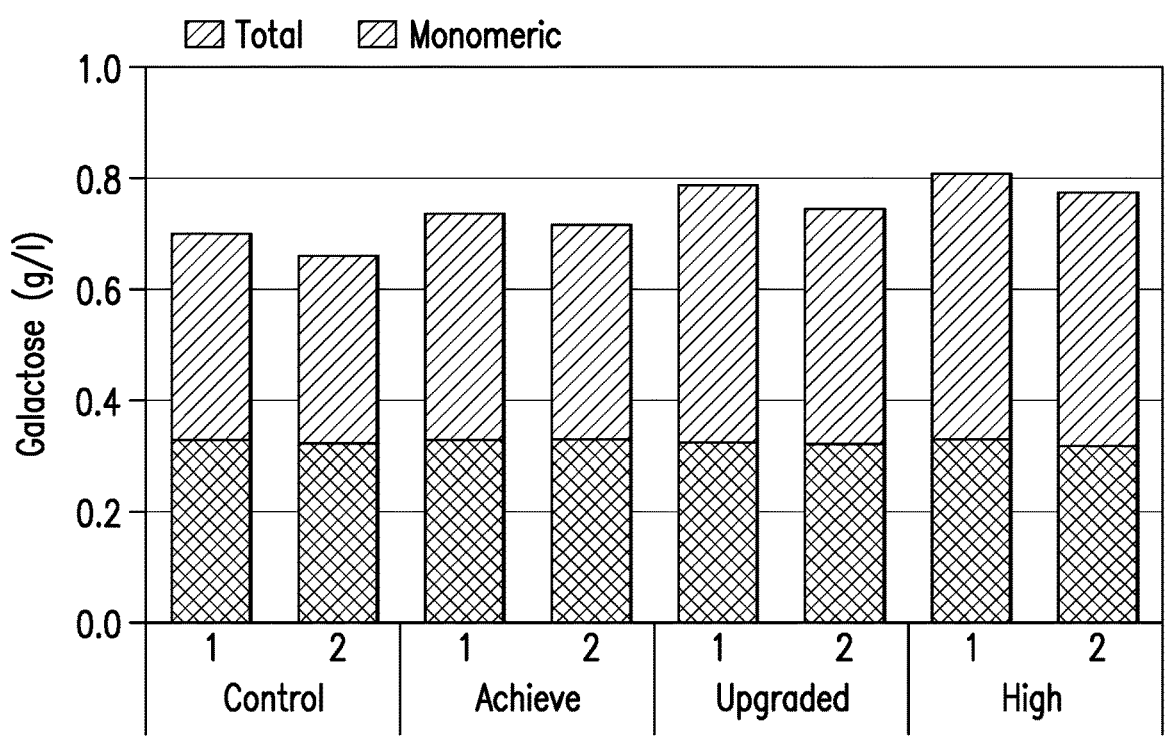
Figure 32:
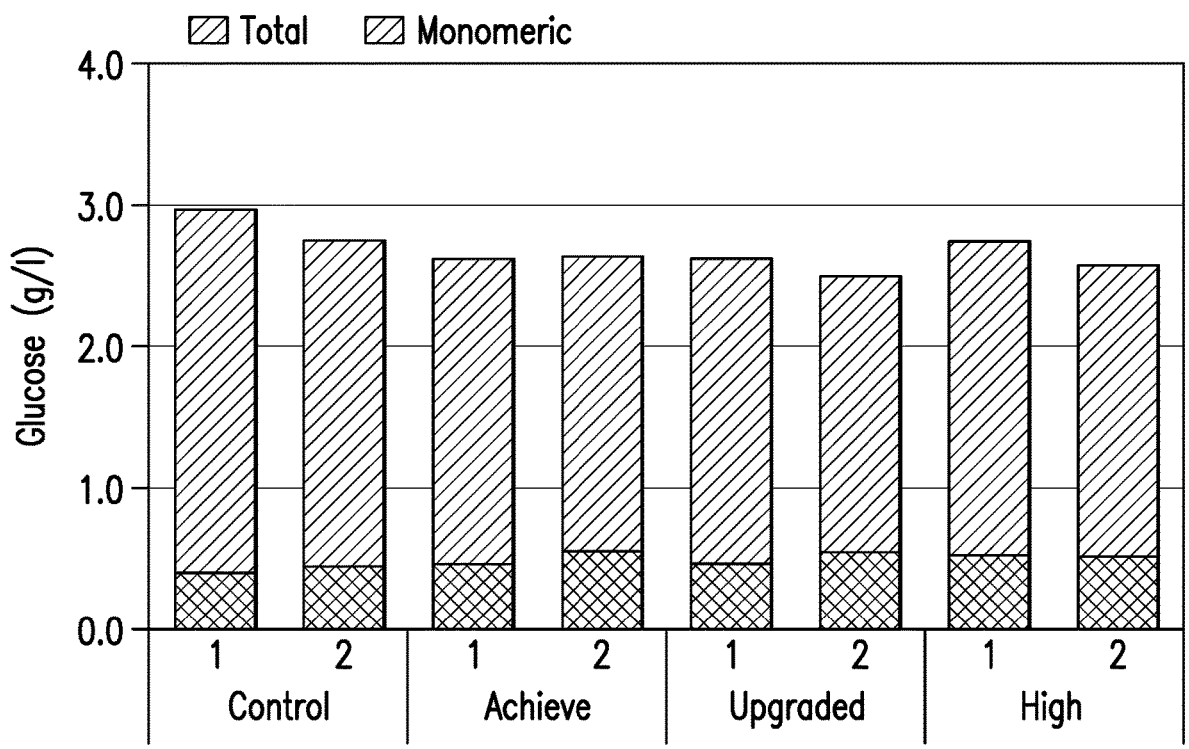
Figure 33:
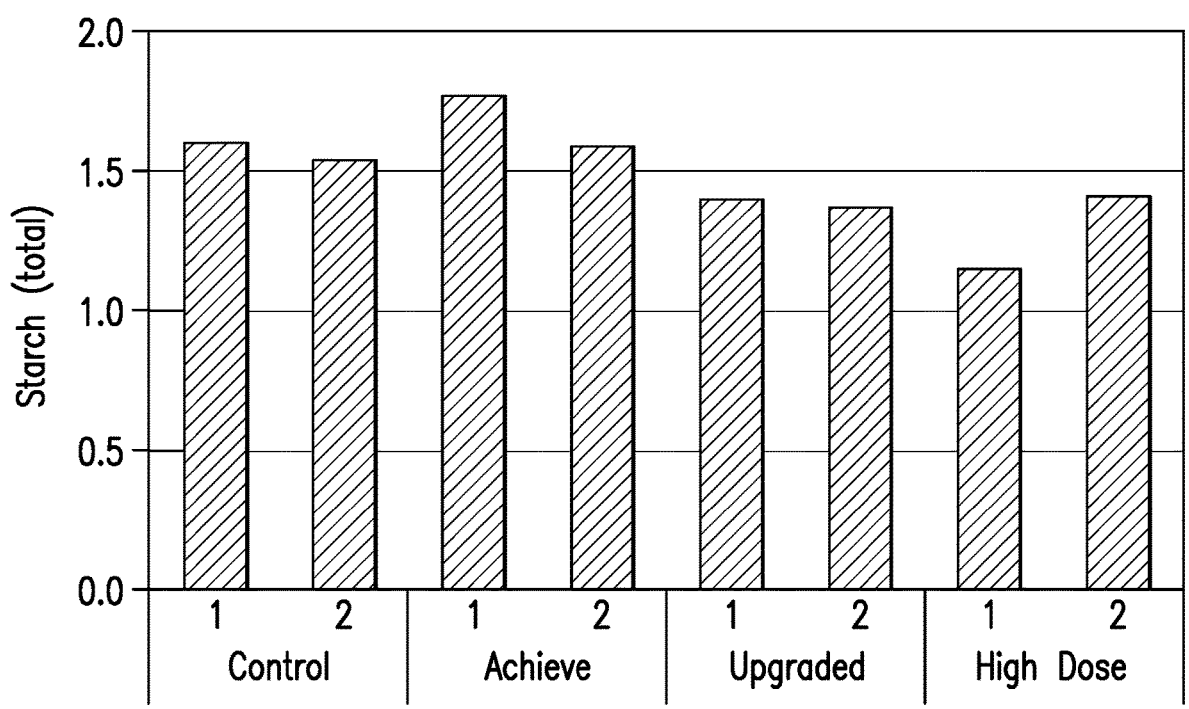
FIG. 33, FIG. 34, FIG. 35, FIG. 36 and FIG. 37 are graphs showing the improved nutritional quality/content of DDGS produced in accordance with a process of the present invention, including DDGS content of Starch (FIG. 33), Protein (FIG. 34), Fat (FIG. 35), Fiber (acid detergent) (FIG. 36), and Fiber (neutral detergent) (FIG. 37).
Figure 34:
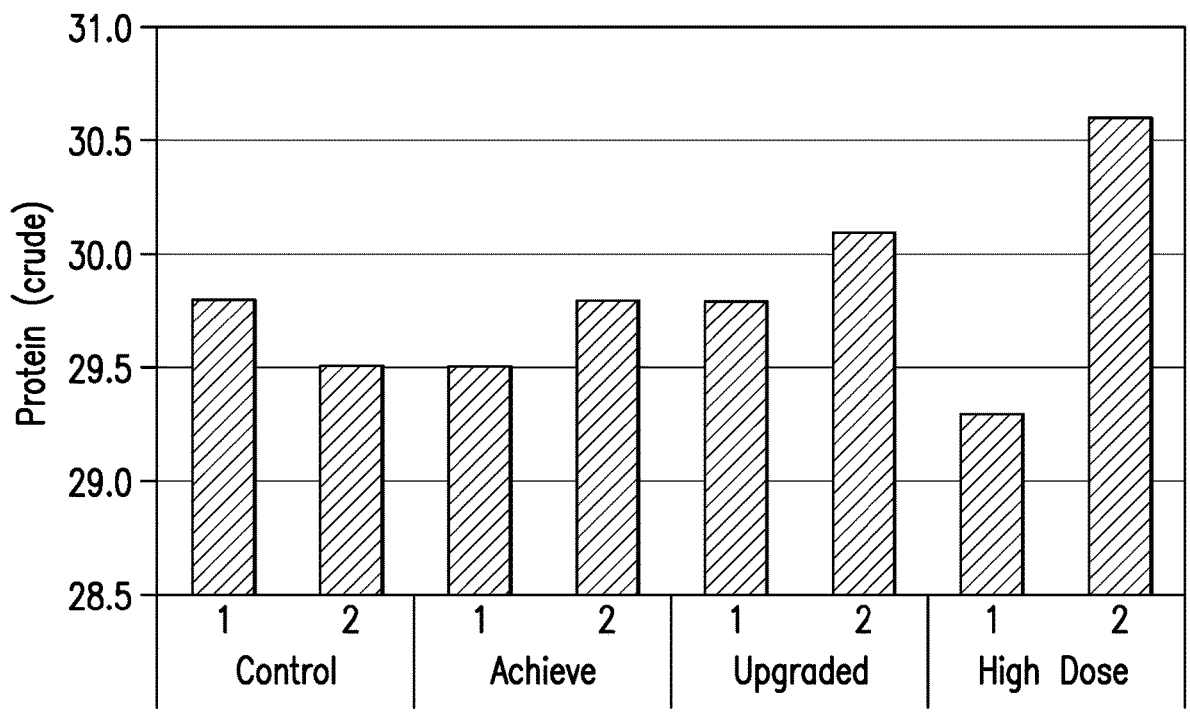
Figure 35:
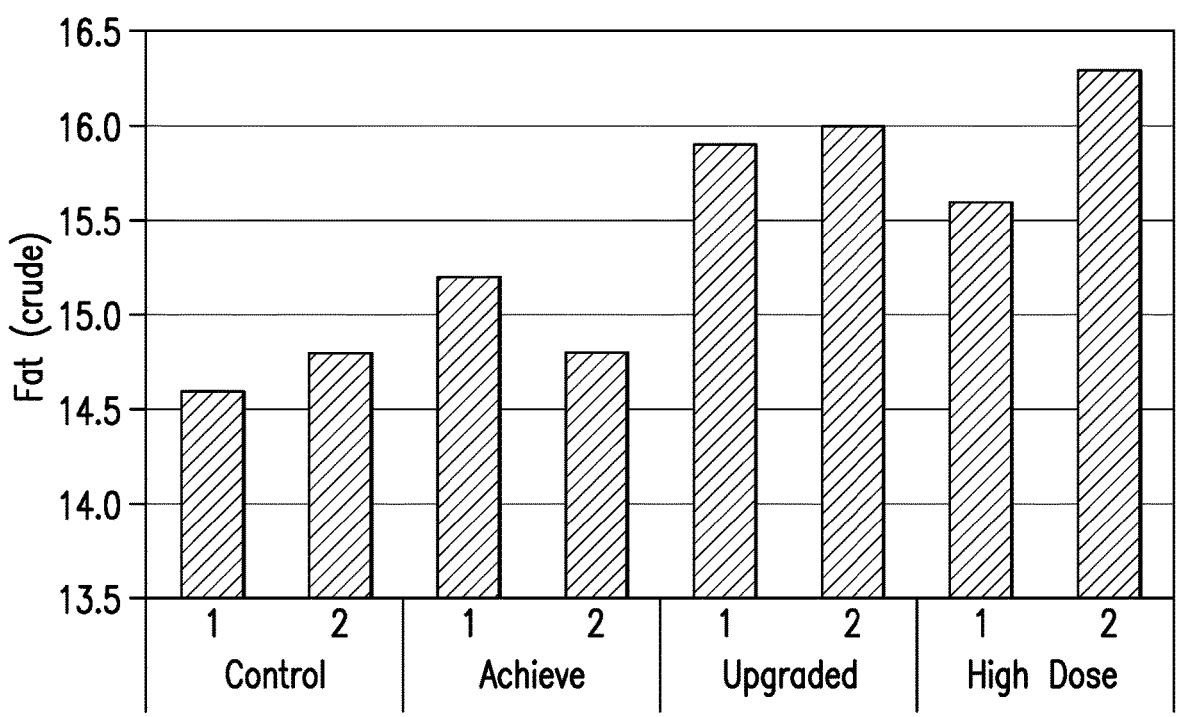
Figure 36:
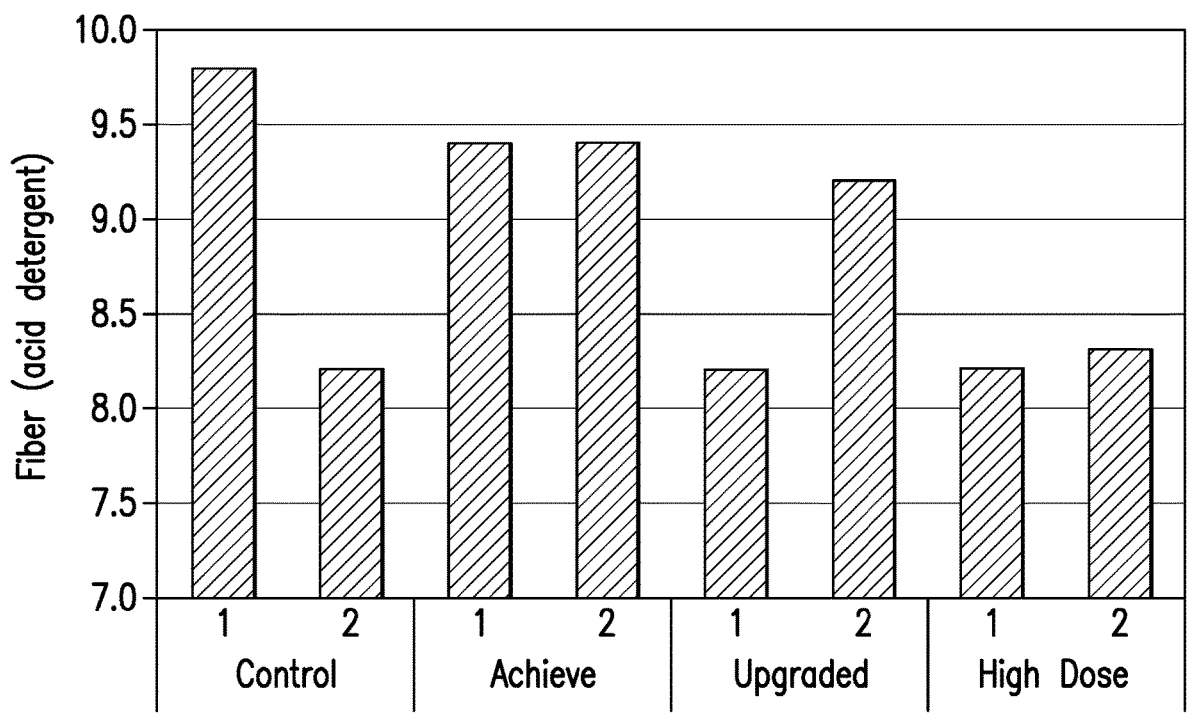
Figure 37:
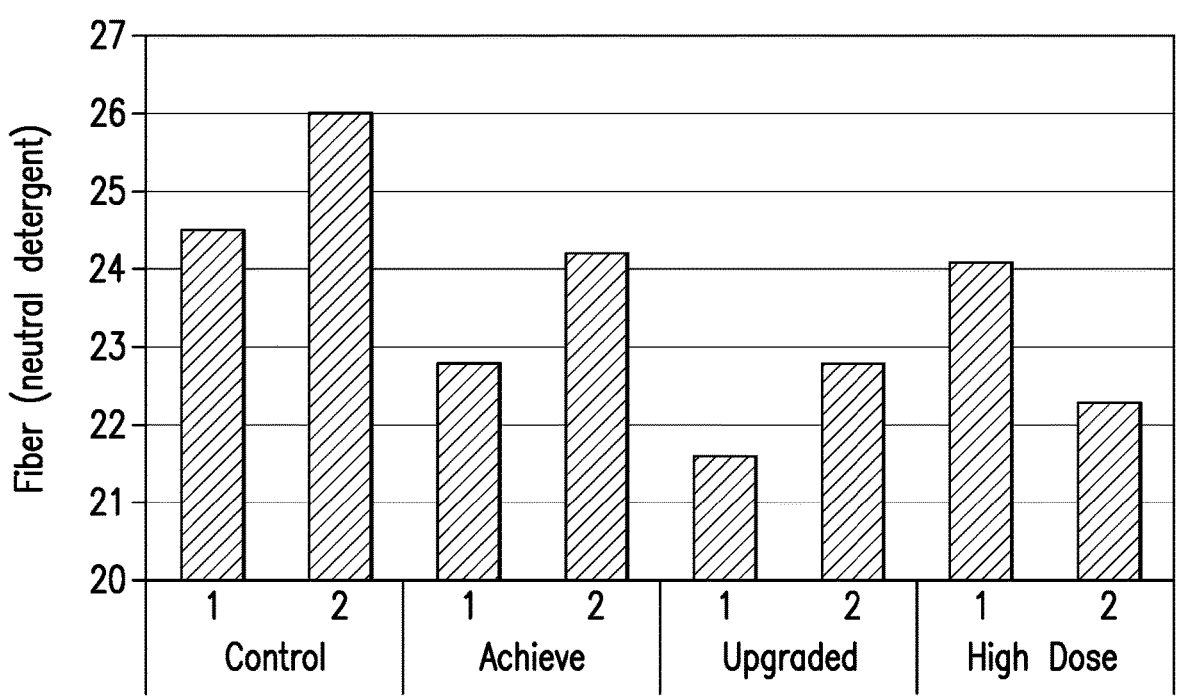

As expected, the E-SEP treatment produced darker DDGS. Surprisingly, the enzyme blends of the present invention and the mega dose of the enzyme blend of the present invention showed no DDGS darkening compared with Excel control suggesting the darkening of DDGS color issue being solved (FIG. 18). However, as seen above, the E-SEP treatment was dried a bit more (~1-2%) compared to the other treatments (FIG. 19).

Materials and Methods

Liquefact in this experiment was plant material received from a commercial ethanol plant. Liquefact was obtained using AA369 and Protease Pfu on a corn mash containing 35.76% DS.

Approximately 5.5 L of mash from a commercial ethanol plant (35% DS) was used for this experiment. After the addition of 34 ppm urea and 3 ppm penicillin, ~300 g of mash was aliquoted into 800 mL fermentation flasks (orange screw caps)×3 replicates for each treatment ×6 (18 total flasks in fermentation).

The yeast was prepared by warming 100 mL of tap water to 32° C., adding 5.5 g of yeast, and incubating at 32° C. for 30 minutes.

SSF enzymes were dosed according to the Table 9 above. Finally, 3 mL of yeast was added to each flask and then all flasks were thoroughly mixed. Solids were adjusted targeting 34% DS and pH was adjusted to 5.0.

Flasks were then transferred to an air shaker and incubated at 32° C. for 66 hours. Whole stillage that has previously been liquefied and fermented (~15% DS) is distilled for 30-40 minutes at 88° C. in the roto-vap to remove ethanol and some water. Whole stillage is attached using a 1 or 2 L round bottom flask as seen below and lowered into the water bath with constant rotation at 85 rpm.

Thin stillage was generated by passing whole stillage (~18-19% DS) across 879 μm sieve stacked on top of a 355 μm sieve, using a spatula. Weights were collected to determine the percent whole stillage ending in wet cake (>355 μm) or thin stillage (<355 μm). This will be important information to correlate to a customer's plant process. Data for mass balance was collected to determine the percent solids ending in wet cake (>355 μm) or thin stillage (<355 μm).

Thin stillage was then added back to the roto-vap to create syrups of each treatment at about 35-40% DS.

Samples were collected after 66 hours to test % ethanol on HPLC. Pct. ethanol yield was measured using the HPLC protocol in Table 1 above in the "Materials & Methods" section.

The samples for HPLC were also assayed for solubilized sugars; both monomeric and as included in oligomers. This was done by acid hydrolysis of oligomers to monomers, followed by assays for the monomeric sugars.

600 μl sample (filtered supernatant; the samples that were run on HPLC) and 200 μl 5N HCl were added to micro centrifuge tubes with screw caps. These were vortexed and incubated at 95° C. for 40 min. in an aluminum block heater and shaker. After cooling down in the refrigerator, 200 μl NaOH (50% NaOH, diluted 4×v/v) was added to neutralize the samples, which were now diluted 1.67×v/v by the added HCl and NaOH. The samples were filtered through 0.2 μm Spin-X micro centrifuge filter units to remove any precipitate. The samples were subsequently diluted 100× on the Hamilton (10 μl sample plus 990 μl water). Final sample dilution was hence 167×.

The above samples were analyzed by HPAEC-PAD, in order to get a more detailed sugar profile. A Dionex ICS-3000 system with a CarboPac PA1 column was used.

The eluent gradient shown in Table 2 above in the "Materials & Methods" section was applied.

The column temperature was 30° C. Sample volume 5 μl. PAD waveform "Gold, Carbo, Quad".

Example 6

Example 6 demonstrates the improved nutritional profile of DDGS produced in accordance with the present invention using an enzyme blend comprising Xylanase and Cellulolytic Composition B.

Two times four IKA laboratory reactors (LR-2.ST the Allrounder) were run with combinations of Cellulolytic Composition B and Xylanase were added. A low, application relevant xylanase dose was tested.

Four IKA laboratory reactors were run in each block. Each reactor was filled with 2100 g mash, for an estimated yield of 260 g DDGS per reactor. The mash was sourced from a commercial ethanol plant and was liquefied with a blend of AA369 and Protease Pfu and hydroheater.

20 kg mash was added to a bucket, and a blue IKA agitator was set up to mix the content. pH was recorded, and it was verified that it was above 4.5 (no contamination). Dry solids were measured and recorded (data not shown).

Urea and penicillin was added according to the mash according to Table 10 below.

TABLE 10

| Agent | Amount |
| --- | --- |
| Urea dose | 50 ppm |
| Urea stock concentration | 200 g/l |
| Urea stock volume | 5.425 ml |
| Penicillin dose | 3 ppm |
| Penicillin stock concentration | 1 g/l |
| Penicillin stock volume | 65.1 ml |

One at a time, the four reactors were placed on a scale, and 2100 g mash was transferred with a pitcher.

The reactors were set up with agitation (50 RPM) and the water baths were set to 32° C. Temperatures inside the reactors were verified after equilibrating. Enzyme dilutions and hydrated yeast were dosed for each block according to the data shown in Table 11 and Table 12 below.

TABLE 11

| Block 1 | | | | |
| --- | --- | --- | --- | --- |
| | | Cellulolytic Composition | | Yeast |
| Block 1 | | | | |
| # | Description | GSA | B | Xylanase | (ml) |
| 1 | High | 417 | 724 | 1391 | 25 |
| 2 | Achieve | 417 | 724 | | 25 |
| 5 | Control | 417 | | | 25 |
| 6 | Upgraded | 417 | 724 | 139 | 25 |
| Total | | 1666 | 2172 | 1530 | 100 |

TABLE 12

| Block 2 Description | GSA | Cellulolytic Composition B | Xylanase | Yeast (ml) |
|---|---|---|---|---|
| Achieve | 417 | 724 | | 25 |
| High | 417 | 724 | 1391 | 25 |
| Upgraded | 417 | 724 | 139 | 25 |
| Control | 417 | | | 25 |
| Total | 1666 | 2172 | 1530 | 100 |

SSF was run for three days.

A 5 g sample was pulled from each reactor for analytical work. Then, the water bath inlets were disconnected on the reactors, and the water bath temperatures were set to 95° C. When all water baths had reached 95° C., the inlets were reconnected, and the reactors were heated for one hour, to simulate distillation and backend operations in a plant. After that, the water baths were turned off, and the reactors left stirring for another hour. The reactor contents were then poured into two 9×13" baking pans per reactor, and a rubber scraper was used to clean everything out of the reactors. The baking pans were placed in a 35° C. oven overnight. Then, the samples were mixed well, frozen, and lyophilized. The final weights and dry solids of the materials were recorded.

The 5 g samples pulled above were centrifuged 5 min. at 5300 RPM, and supernatants were filtered with 0.2 μm syringe filters. The filtered supernatants were submitted for HPLC "as is", and also used for acid hydrolysis followed by HPAEC-PAD (IC), to hydrolyze oligosaccharides to monosaccharides, in order to quantify all solubilized sugars. The acid hydrolysis was carried out as follows. 300 μl sample and 100 μl 5N HCl was added to micro centrifuge tubes with screw caps. The tubes were vortexed and placed in a heating block at 95° C. for 40 min. After cooling, they were neutralized with 125 μl NaOH (50% w/w NaOH, diluted 5×vol/vol) and vortexed. The samples were diluted 20× on a Hamilton Microlab 600 diluter before HPAEC-PAD (35× total dilution). Unhydrolyzed samples were also diluted 35× and submitted for IC. A Dionex ICS-3000 system with a CarboPac PA1 column was used. The following eluent gradient shown in Table 2 above was applied.

The column temperature was 30° C. Sample volume 5 μl. PAD waveform "Gold, Carbo, Quad". Each reactor batch was split for five birds, with 5/32 going to each. This should give 38.6 g per bird, and 7/32, or 54.0 g, remaining for analytical work. The samples were labelled as shown in Table 13 below.

TABLE 13

| Description | Treatment | Bird | Block | Reactor |
|---|---|---|---|---|
| Control | A | 1-5 | 1 | 5 |
| | | 6-10 | 2 | 6 |
| Achieve | B | 1-5 | 1 | 2 |
| | | 6-10 | 2 | 1 |
| Upgraded | C | 1-5 | 1 | 6 |
| | | 6-10 | 2 | 5 |
| High | D | 1-5 | 1 | 1 |
| | | 6-10 | 2 | 2 |

The samples were split on a two-way splitter into eight fractions, of 31±3 g each. Five of the eight fractions were transferred to ziplock bags. Then, more material was added to the bags with a spatula, filling up to 38.7 g per bag (5/32 of the total weight). All the remaining material was used for analytical samples.

Results

The weights recorded for the contents poured out of the reactors are shown in Table 14 below. Block 1 reactor 1 was not weighed immediately, and there was substantial evaporation as soon as the hot contents were poured into the baking pans. Hence, the first reactor is probably similar to the others.

TABLE 14

| Block | Reactor | Treatment | Beer (g) | Finished (g) |
|---|---|---|---|---|
| 1 | 1 | High | 1729 | 250 |
| | 4 | Achieve | 1768 | 254 |
| | 5 | Control | 1768 | 254 |
| | 6 | Upgraded | 1759 | 249 |
| 2 | 1 | Achieve | 1732 | 247 |
| | 4 | High | 1740 | 250 |
| | 5 | Upgraded | 1756 | 250 |
| | 6 | Control | 1757 | 255 |

The HPLC results are shown in Table 15 below and in FIGS. 20-28.

TABLE 15

| Block | Treatment | DP4+ | DP3 | DP2 | Gluc | Fruc | Lactate |
|---|---|---|---|---|---|---|---|
| 1 | High | 1.317 | 0.095 | 0.168 | 0.072 | 0.123 | 0.206 |
| | Achieve | 0.854 | 0.079 | 0.152 | 0.064 | 0.124 | 0.185 |
| | Control | 0.772 | 0.107 | 0.182 | 0.060 | 0.127 | 0.181 |
| | Upgraded | 1.283 | 0.090 | 0.158 | 0.063 | 0.122 | 0.183 |
| 2 | Achieve | 0.874 | 0.065 | 0.153 | 0.074 | 0.199 | 0.170 |
| | High | 1.331 | 0.075 | 0.155 | 0.068 | 0.142 | 0.169 |
| | Upgraded | 1.289 | 0.070 | 0.154 | 0.070 | 0.144 | 0.165 |
| | Control | 0.789 | 0.100 | 0.184 | 0.065 | 0.178 | 0.168 |

| Block | Treatment | Glycerol | Acetate | EtOH |
|---|---|---|---|---|
| 1 | High | 1.789 | 0.184 | 13.944 |
| | Achieve | 1.759 | 0.169 | 13.975 |
| | Control | 1.751 | 0.163 | 13.939 |
| | Upgraded | 1.753 | 0.167 | 13.963 |
| 2 | Achieve | 1.787 | 0.111 | 13.848 |
| | High | 1.741 | 0.112 | 13.834 |
| | Upgraded | 1.754 | 0.112 | 13.840 |
| | Control | 1.765 | 0.112 | 13.836 |

The HPLC results are very consistent.

For IC, samples were run "as is" to get monomeric sugar concentrations, and after the usual HCl hydrolysis to get total solubilized sugar concentrations, as shown in Table 16 below and FIGS. 29-32.

TABLE 16

| Block | HCl | Description | Arabinose | Xylose | Galactose | Glucose |
|---|---|---|---|---|---|---|
| 1 | No | Control | 0.08 | 0.02 | 0.33 | 0.40 |
| | | Achieve | 0.11 | 0.02 | 0.33 | 0.46 |
| | | Upgraded | 0.14 | 0.02 | 0.33 | 0.46 |
| | | High | 0.14 | 0.02 | 0.33 | 0.53 |
| | Yes | Control | 0.80 | 0.58 | 0.70 | 2.96 |
| | | Achieve | 0.98 | 0.78 | 0.74 | 2.62 |
| | | Upgraded | 2.16 | 1.78 | 0.79 | 2.62 |
| | | High | 2.34 | 1.96 | 0.81 | 2.75 |
| 2 | No | Control | 0.07 | 0.00 | 0.32 | 0.45 |
| | | Achieve | 0.10 | 0.03 | 0.33 | 0.55 |
| | | Upgraded | 0.12 | 0.02 | 0.32 | 0.55 |
| | | High | 0.12 | 0.01 | 0.32 | 0.51 |

TABLE 16-continued

| Block | HCl | Description | Arabinose | Xylose | Galactose | Glucose |
|---|---|---|---|---|---|---|
| | Yes | Control | 0.73 | 0.52 | 0.66 | 2.74 |
| | | Achieve | 0.97 | 0.76 | 0.72 | 2.63 |
| | | Upgraded | 1.98 | 1.67 | 0.75 | 2.50 |
| | | High | 2.16 | 1.84 | 0.78 | 2.58 |

The results shown in Table 16 and FIGS. 29-32 are consistent, and show increases in total solubilized arabinose and xylose when the xylanase was added. There is very little difference between "Upgraded" with 3 μg xylanase, and "High" with 30 μg xylanase. The monomeric arabinose and xylose concentrations are very low. For galactose and glucose, there is no clear trend. Hence, the enzymes do not appear to affect galactose and residual glucose concentrations.

The results showing the improved nutritional quality and/or content of the DDGS are shown in FIGS. 33-37, and in particular show a clear trend showing that the DDGS have higher measured fat. The trends for ADF and NDF fiber are, however, less clear, and show variation between the duplicates.

The invention claimed is:

1. A process for producing a fermentation product from starch-containing material comprising the steps of:
    (a) liquefying a starch-containing material with a thermostable alpha-amylase, wherein the starch-containing material is corn;
    (b) saccharifying the liquefied material obtained in step (a) with a glucoamylase and a GH30_8 family xylanase;
    (c) fermenting using a yeast to produce the fermentation product, wherein the fermentation product is fuel ethanol; and
    (d) recovering a co-product, wherein the co-product is distillers dried grains (DDG) or distillers dried grains with solubles (DDGS), wherein saccharifying and fermenting are performed simultaneously, and wherein the GH30_8 xylanase is selected from the group consisting of:
        (i) a GH30_8 xylanase having at least 90% amino acid sequence identity to SEQ ID NO: 2;
        (ii) a GH30_8 xylanase having at least 90% amino acid sequence identity to SEQ ID NO: 3;
        (iii) a GH30_8 xylanase having at least 94% amino acid sequence identity to SEQ ID NO: 4;
        (iv) a GH30_8 xylanase having at least 91% amino acid sequence identity to SEQ ID NO: 5; and
        (v) a GH30_8 xylanase having at least 91% amino acid sequence identity to SEQ ID NO: 6.

2. The process of claim 1, wherein the DDG or DDGS have an improved nutritional quality compared to DDG or DDGS recovered as a co-product of a process for producing a fermentation product in which the xylanase or enzyme blend comprising the xylanase is not present or added.

3. The process of claim 1, wherein the GH30_8 xylanase has an amino acid sequence with at least 95% sequence identity to SEQ ID NO: 2.

4. The process of claim 1, wherein the GH30_8 xylanase has an amino acid sequence with at least 97% sequence identity to SEQ ID NO: 2.

5. The process of claim 1, wherein the GH30_8 xylanase has an amino acid sequence with at least 95% sequence identity to SEQ ID NO: 3.

6. The process of claim 1, wherein the GH30_8 xylanase has an amino acid sequence with at least 97% sequence identity to SEQ ID NO: 3.

7. The process of claim 1, wherein the GH30_8 xylanase has an amino acid sequence with at least 95% sequence identity to SEQ ID NO: 4.

8. The process of claim 1, wherein the GH30_8 xylanase has an amino acid sequence with at least 97% sequence identity to SEQ ID NO: 4.

9. The process of claim 1, wherein the GH30_8 xylanase has an amino acid sequence with at least 95% sequence identity to SEQ ID NO: 5.

10. The process of claim 1, wherein the GH30_8 xylanase has an amino acid sequence with at least 97% sequence identity to SEQ ID NO: 5.

11. The process of claim 1, wherein the GH30_8 xylanase has an amino acid sequence with at least 95% sequence identity to SEQ ID NO: 6.

12. The process of claim 1, wherein the GH30_8 xylanase has an amino acid sequence with at least 97% sequence identity to SEQ ID NO: 6.

13. A process of producing a fermentation product, comprising the following steps:
    (a) saccharifying a starch-containing material at a temperature below the initial gelatinization temperature with an alpha-amylase, a glucoamylase, and a GH30_8 family xylanase, wherein the starch-containing material is corn;
    (b) fermenting using a fermentation organism yeast to produce the fermentation product, wherein the fermentation product is fuel ethanol; and (c) recovering a co-product, wherein the co-product is distillers dried grains (DDG) or distillers dried grains with solubles (DDGS), wherein saccharifying and fermenting are performed simultaneously, and wherein the GH30_8 xylanase is selected from the group consisting of:
  (i) a GH30_8 xylanase having at least 90% amino acid sequence identity to SEQ ID NO: 2;
  (ii) a GH30_8 xylanase having at least 90% amino acid sequence identity to SEQ ID NO: 3;
  (iii) a GH30_8 xylanase having at least 94% amino acid sequence identity to SEQ ID NO: 4;
  (iv) a GH30_8 xylanase having at least 91% amino acid sequence identity to SEQ ID NO: 5; and
  (v) a GH30_8 xylanase having at least 91% amino acid sequence identity to SEQ ID NO: 6.

14. The process of claim 13, wherein the DDG or DDGS have an improved nutritional quality compared to DDG or DDGS recovered as a co-product of a process for producing a fermentation product in which the xylanase or enzyme blend comprising the xylanase is not present or added.

15. The process of claim 13, wherein the GH30_8 xylanase has an amino acid sequence with at least 95% sequence identity to SEQ ID NO: 2.

16. The process of claim 13, wherein the GH30_8 xylanase has an amino acid sequence with at least 97% sequence identity to SEQ ID NO: 2.

17. The process of claim 1, wherein the GH30_8 xylanase has an amino acid sequence with at least 95% sequence identity to SEQ ID NO: 3.

18. The process of claim 1, wherein the GH30_8 xylanase has an amino acid sequence with at least 97% sequence identity to SEQ ID NO: 3.

19. The process of claim 1, wherein the GH30_8 xylanase has an amino acid sequence with at least 95% sequence identity to SEQ ID NO: 4.

20. The process of claim 1, wherein the GH30_8 xylanase has an amino acid sequence with at least 97% sequence identity to SEQ ID NO: 4.

21. The process of claim 1, wherein the GH30_8 xylanase has an amino acid sequence with at least 95% sequence identity to SEQ ID NO: 5.

22. The process of claim 1, wherein the GH30_8 xylanase has an amino acid sequence with at least 97% sequence identity to SEQ ID NO: 5.

23. The process of claim 1, wherein the GH30_8 xylanase has an amino acid sequence with at least 95% sequence identity to SEQ ID NO: 6.

24. The process of claim 1, wherein the GH30_8 xylanase has an amino acid sequence with at least 97% sequence identity to SEQ ID NO: 6.

* * * * *

SEQUENCE LISTING

<160> NUMBER OF SEQ ID NOS: 26

<210> SEQ ID NO 1
<211> LENGTH: 390
<212> TYPE: PRT
<213> ORGANISM: Bacillus subtilis

<400> SEQUENCE: 1

```
Ala Ser Asp Val Thr Val Asn Val Ser Ala Glu Lys Gln Val Ile Arg
1               5                   10                  15

Gly Phe Gly Gly Met Asn His Pro Ala Trp Ala Gly Asp Leu Thr Ala
                20                  25                  30

Ala Gln Arg Glu Thr Ala Phe Gly Asn Gly Gln Asn Gln Leu Gly Phe
            35                  40                  45

Ser Ile Leu Arg Ile His Val Asp Glu Asn Arg Asn Asn Trp Tyr Lys
    50                  55                  60

Glu Val Glu Thr Ala Lys Ser Ala Val Lys His Gly Ala Ile Val Phe
65                  70                  75                  80

Ala Ser Pro Trp Asn Pro Pro Ser Asp Met Val Glu Thr Phe Asn Arg
                85                  90                  95

Asn Gly Asp Thr Ser Ala Lys Arg Leu Lys Tyr Asn Lys Tyr Ala Ala
                100                 105                 110

Tyr Ala Gln His Leu Asn Asp Phe Val Thr Phe Met Lys Asn Asn Gly
            115                 120                 125

Val Asn Leu Tyr Ala Ile Ser Val Gln Asn Glu Pro Asp Tyr Ala His
    130                 135                 140

Glu Trp Thr Trp Thr Pro Gln Glu Ile Leu Arg Phe Met Arg Glu
145                 150                 155                 160

Asn Ala Gly Ser Ile Asn Ala Arg Val Ile Ala Pro Glu Ser Phe Gln
                165                 170                 175

Tyr Leu Lys Asn Leu Ser Asp Pro Ile Leu Asn Asp Pro Gln Ala Leu
            180                 185                 190

Ala Asn Met Asp Ile Leu Gly Thr His Leu Tyr Gly Thr Gln Val Ser
        195                 200                 205

Gln Phe Pro Tyr Pro Leu Phe Lys Gln Lys Gly Ala Gly Lys Asp Leu
    210                 215                 220

Trp Met Thr Glu Val Tyr Tyr Pro Asn Ser Asp Thr Asn Ser Ala Asp
225                 230                 235                 240

Arg Trp Pro Glu Ala Leu Asp Val Ser Gln His Ile His Asn Ala Met
                245                 250                 255

Val Glu Gly Asp Phe Gln Ala Tyr Val Trp Trp Tyr Ile Arg Arg Ser
            260                 265                 270

Tyr Gly Pro Met Lys Glu Asp Gly Thr Ile Ser Lys Arg Gly Tyr Asn
        275                 280                 285
```

```
Met Ala His Phe Ser Lys Phe Val Arg Pro Gly Tyr Val Arg Ile Asp
             290                 295                 300

Ala Thr Lys Asn Pro Asn Ala Asn Val Tyr Val Ser Ala Tyr Lys Gly
305                 310                 315                 320

Asp Asn Lys Val Val Ile Val Ala Ile Asn Lys Ser Asn Thr Gly Val
                325                 330                 335

Asn Gln Asn Phe Val Leu Gln Asn Gly Ser Ala Ser Asn Val Ser Arg
            340                 345                 350

Trp Ile Thr Ser Ser Ser Asn Leu Gln Pro Gly Thr Asn Leu Thr
        355                 360                 365

Val Ser Gly Asn His Phe Trp Ala His Leu Pro Ala Gln Ser Val Thr
370                 375                 380

Thr Phe Val Val Asn Arg
385                 390

<210> SEQ ID NO 2
<211> LENGTH: 390
<212> TYPE: PRT
<213> ORGANISM: Bacillus subtilis

<400> SEQUENCE: 2

Ala Ser Asp Val Thr Val Asn Val Ser Ala Glu Lys Gln Val Ile Arg
1               5                   10                  15

Gly Phe Gly Gly Met Asn His Pro Ala Trp Ala Gly Asp Leu Thr Ala
            20                  25                  30

Ala Gln Arg Glu Thr Ala Phe Gly Asn Gly Gln Asn Gln Leu Gly Phe
        35                  40                  45

Ser Ile Leu Arg Ile His Val Asp Glu Asn Arg Asn Asn Trp Tyr Lys
    50                  55                  60

Glu Val Glu Thr Ala Lys Ser Ala Val Lys His Gly Ala Ile Val Phe
65                  70                  75                  80

Ala Ser Pro Trp Asn Pro Pro Ser Asp Met Val Glu Thr Phe Asn Arg
                85                  90                  95

Asn Gly Asp Thr Ser Ala Lys Arg Leu Lys Tyr Asn Lys Tyr Ala Ala
            100                 105                 110

Tyr Ala Gln His Leu Asn Asp Phe Val Thr Phe Met Lys Asn Asn Gly
        115                 120                 125

Val Asn Leu Tyr Ala Ile Ser Val Gln Asn Glu Pro Asp Tyr Ala His
    130                 135                 140

Glu Trp Thr Trp Thr Pro Gln Glu Ile Leu Arg Phe Met Arg Glu
145                 150                 155                 160

Asn Ala Gly Ser Ile Asn Ala Arg Val Ile Ala Pro Glu Ser Phe Gln
                165                 170                 175

Tyr Leu Lys Asn Leu Ser Asp Pro Ile Leu Asn Asp Pro Gln Ala Leu
            180                 185                 190

Ala Asn Met Asp Ile Leu Gly Thr His Leu Tyr Gly Thr Gln Val Ser
        195                 200                 205

Gln Phe Pro Tyr Pro Leu Phe Lys Gln Lys Gly Ala Gly Lys Asp Leu
    210                 215                 220

Trp Met Thr Glu Val Tyr Tyr Pro Asn Ser Asp Thr Asn Ser Ala Asp
225                 230                 235                 240

Arg Trp Pro Glu Ala Leu Asp Val Ser Gln His Ile His Asn Ala Met
                245                 250                 255

Val Glu Gly Asp Phe Gln Ala Tyr Val Trp Trp Tyr Ile Arg Arg Ser
```

```
                        260                 265                 270
Tyr Gly Pro Met Lys Glu Asp Gly Thr Ile Ser Lys Arg Gly Tyr Asn
                275                 280                 285

Met Ala His Phe Ser Lys Phe Val Arg Pro Gly Tyr Val Arg Ile Asp
                290                 295                 300

Ala Thr Lys Asn Pro Asn Ala Asn Val Tyr Val Ser Ala Tyr Lys Gly
305                 310                 315                 320

Asp Asn Lys Val Val Ile Val Ala Ile Asn Lys Ser Asn Thr Gly Val
                    325                 330                 335

Asn Gln Asn Phe Val Leu Gln Asn Gly Ser Ala Ser Asn Val Ser Arg
                340                 345                 350

Trp Ile Thr Ser Ser Ser Asn Leu Gln Pro Gly Thr Asn Leu Thr
                355                 360                 365

Val Ser Gly Asn His Phe Trp Ala His Leu Pro Ala Gln Ser Val Thr
                370                 375                 380

Thr Phe Val Val Asn Arg
385                 390

<210> SEQ ID NO 3
<211> LENGTH: 390
<212> TYPE: PRT
<213> ORGANISM: Bacillus subtilis

<400> SEQUENCE: 3

Ala Asn Asp Val Thr Val Asn Ile Ser Ala Glu Lys Gln Val Ile Arg
1               5                   10                  15

Gly Phe Gly Gly Met Asn His Pro Ala Trp Val Gly Asp Leu Thr Ala
                20                  25                  30

Ala Gln Arg Glu Thr Ala Phe Gly Asn Gly Gln Asn Gln Leu Gly Phe
            35                  40                  45

Ser Ile Leu Arg Ile His Val Asp Glu Asn Arg Asn Asn Trp Tyr Lys
        50                  55                  60

Glu Val Glu Thr Ala Lys Ser Ala Ile Lys His Gly Ala Ile Val Phe
65                  70                  75                  80

Ala Ser Pro Trp Asn Pro Pro Ser Asn Met Val Glu Thr Phe Asn His
                85                  90                  95

Asn Gly Asp Thr Ser Ala Lys Arg Leu Arg Tyr Asp Lys Tyr Ala Ala
                100                 105                 110

Tyr Ala Gln His Leu Asn Asp Phe Val Thr Phe Met Lys Ser Asn Gly
            115                 120                 125

Val Asn Leu Tyr Ala Ile Ser Ile Gln Asn Glu Pro Asp Tyr Ala His
        130                 135                 140

Glu Trp Thr Trp Trp Thr Pro Gln Glu Ile Leu Arg Phe Met Arg Glu
145                 150                 155                 160

Asn Ala Gly Ser Ile Asn Ala Arg Val Ile Ala Pro Glu Ser Phe Gln
                165                 170                 175

Tyr Leu Lys Asn Leu Ser Asp Pro Ile Leu Asn Asp Pro Gln Ala Leu
                180                 185                 190

Ala Asn Met Asp Ile Leu Gly Thr His Leu Tyr Gly Thr Gln Val Ser
            195                 200                 205

Gln Phe Pro Tyr Pro Leu Phe Lys Gln Lys Gly Ala Gly Lys Asp Leu
        210                 215                 220

Trp Met Thr Glu Val Tyr Tyr Pro Asn Ser Asp Asn Asn Ser Ala Asp
225                 230                 235                 240
```

-continued

```
Arg Trp Pro Glu Ala Leu Asp Val Ser Gln His Ile His Asn Ser Met
            245                 250                 255

Val Glu Gly Asp Phe Gln Ala Tyr Val Trp Trp Tyr Ile Arg Arg Ser
260                 265                 270

Tyr Gly Pro Met Lys Glu Asp Gly Thr Ile Ser Lys Arg Gly Tyr Asn
        275                 280                 285

Met Ala His Phe Ser Lys Phe Val Arg Pro Gly Tyr Val Arg Ile Asp
290                 295                 300

Ala Thr Lys Asn Pro Asn Pro Asn Val Tyr Val Ser Ala Tyr Lys Gly
305                 310                 315                 320

Asp Asn Lys Val Val Ile Val Ala Ile Asn Lys Ser Asn Thr Gly Val
                325                 330                 335

Asn Gln Asn Phe Val Leu Gln Asn Gly Ser Ala Ser Gln Val Ser Arg
                340                 345                 350

Trp Ile Thr Ser Ser Asn Ser Asn Leu Gln Pro Gly Thr Asn Leu Lys
        355                 360                 365

Val Thr Asp Asn His Phe Trp Ala His Leu Pro Ala Gln Ser Val Thr
370                 375                 380

Thr Phe Val Val Ile Arg
385                 390

<210> SEQ ID NO 4
<211> LENGTH: 390
<212> TYPE: PRT
<213> ORGANISM: Bacillus amyloliquefaciens

<400> SEQUENCE: 4

Ala Asn Asp Val Thr Val Asn Ile Ser Ala Glu Arg Gln Val Ile Arg
1               5                   10                  15

Gly Phe Gly Gly Met Asn His Pro Ala Trp Val Gly Asp Leu Thr Ala
                20                  25                  30

Ala Gln Arg Glu Thr Ala Phe Gly Asn Gly Gln Asn Gln Leu Gly Phe
        35                  40                  45

Ser Ile Leu Arg Ile His Val Asp Glu Asn Arg Asn Asn Trp Tyr Lys
    50                  55                  60

Glu Val Glu Thr Ala Lys Ser Ala Ile Lys His Gly Ala Ile Val Phe
65                  70                  75                  80

Ala Ser Pro Trp Asn Pro Pro Asn Asp Met Val Glu Thr Phe Asn His
                85                  90                  95

Asn Gly Asp Thr Ser Ala Lys Arg Leu Arg Tyr Asp Lys Tyr Ala Ala
            100                 105                 110

Tyr Ala Gln His Leu Asn Asp Phe Val Asn Phe Met Lys Ser Asn Gly
        115                 120                 125

Val Asn Leu Tyr Ala Ile Ser Ile Gln Asn Glu Pro Asp Tyr Ala His
    130                 135                 140

Glu Trp Thr Trp Trp Thr Pro Gln Glu Ile Leu Arg Phe Met Arg Glu
145                 150                 155                 160

Asn Ala Gly Ser Ile Asn Ala Arg Val Ile Ala Pro Glu Ser Phe Gln
                165                 170                 175

Tyr Leu Lys Asn Leu Ser Asp Pro Ile Leu Asn Asp Pro Gln Ala Leu
            180                 185                 190

Ala Asn Met Asp Ile Leu Gly Thr His Leu Tyr Gly Thr Gln Val Ser
        195                 200                 205

Gln Phe Pro Tyr Pro Leu Phe Lys Gln Lys Gly Ala Gly Lys Asp Leu
    210                 215                 220
```

-continued

```
Trp Met Thr Glu Val Tyr Tyr Pro Asn Ser Asp Asn Ser Ala Asp
225                 230                 235                 240

Arg Trp Pro Glu Ala Leu Asp Val Ser Gln His Ile His Ser Ser Met
            245                 250                 255

Val Glu Gly Asp Leu Gln Ala Tyr Val Trp Trp Tyr Ile Arg Arg Ser
                260                 265                 270

Tyr Gly Pro Met Lys Glu Asp Gly Thr Ile Ser Lys Arg Gly Tyr Asn
            275                 280                 285

Met Ala His Phe Ser Lys Phe Val Arg Pro Gly Tyr Val Arg Ile Asp
290                 295                 300

Ala Thr Lys Asn Pro Asn Pro Asn Val Tyr Val Ser Ala Tyr Lys Gly
305                 310                 315                 320

Asp Asn Lys Val Val Ile Val Ala Ile Asn Lys Thr Asn Thr Gly Val
                325                 330                 335

Asn Gln Asn Phe Val Leu Gln Asn Gly Ser Ala Ser Gln Val Ser Arg
            340                 345                 350

Trp Ile Thr Ser Ser Asn Ser Asn Leu Gln Pro Gly Thr Asp Leu Lys
            355                 360                 365

Val Thr Asp Asn His Phe Trp Ala His Leu Pro Ala Gln Ser Val Thr
            370                 375                 380

Thr Phe Val Val Lys Arg
385                 390

<210> SEQ ID NO 5
<211> LENGTH: 390
<212> TYPE: PRT
<213> ORGANISM: Bacillus amyloliquefaciens HB-26

<400> SEQUENCE: 5

Ala Ser Asp Ala Thr Val Asn Ile Ser Ala Glu Arg Gln Val Ile Arg
1               5                   10                  15

Gly Phe Gly Gly Met Asn His Pro Ala Trp Ile Gly Asp Leu Thr Ala
                20                  25                  30

Pro Gln Arg Val Thr Ala Phe Gly Asn Gly Gln Asn Gln Leu Gly Phe
            35                  40                  45

Ser Val Leu Arg Ile His Val Asp Glu Asn Arg Asn Asn Trp Tyr Lys
    50                  55                  60

Glu Val Glu Thr Ala Lys Ser Ala Ile Lys His Gly Ala Ile Val Phe
65                  70                  75                  80

Ala Ser Pro Trp Asn Pro Pro Asn Asp Met Val Glu Thr Phe Asn His
                85                  90                  95

Asn Gly Asp Thr Ser Ala Lys Arg Leu Arg Tyr Asp Lys Tyr Ala Ala
            100                 105                 110

Tyr Ala Gln His Leu Asn Asp Phe Val Asn Phe Met Lys Ser Asn Gly
        115                 120                 125

Val Asn Leu Tyr Ala Ile Ser Met Gln Asn Glu Pro Asp Tyr Ala His
    130                 135                 140

Glu Trp Thr Trp Trp Thr Pro Gln Glu Ile Leu Arg Phe Met Arg Glu
145                 150                 155                 160

Asn Ala Gly Ser Ile Asn Thr Arg Val Ile Ala Pro Glu Ser Phe Gln
                165                 170                 175

Tyr Leu Lys Asn Ile Ser Asp Pro Ile Leu Asn Asp Pro Gln Ala Leu
            180                 185                 190

Arg Asn Met Asp Ile Leu Gly Thr His Leu Tyr Gly Thr Gln Val Ser
```

```
                195                 200                 205
Gln Phe Pro Tyr Pro Leu Phe Lys Gln Lys Gly Gly Gly Lys Glu Leu
210                 215                 220

Trp Met Thr Glu Val Tyr Tyr Pro Asn Ser Asp Asn Tyr Ser Ala Asp
225                 230                 235                 240

Arg Trp Pro Glu Ala Leu Gly Val Ser Glu His Ile His His Ser Met
                245                 250                 255

Val Glu Gly Asp Phe Gln Ala Tyr Val Trp Trp Tyr Ile Arg Arg Ser
            260                 265                 270

Tyr Gly Pro Met Lys Glu Asp Gly Met Ile Ser Lys Arg Gly Tyr Asn
                275                 280                 285

Met Ala His Phe Ser Lys Phe Val Arg Pro Gly Tyr Val Arg Ile Asp
            290                 295                 300

Ala Thr Lys Asn Pro Glu Pro Asn Val Tyr Val Ser Ala Tyr Lys Gly
305                 310                 315                 320

Asp Asn Lys Val Val Ile Val Ala Ile Asn Lys Asn Asn Thr Gly Val
                325                 330                 335

Asn Gln Asn Phe Val Leu Gln Asn Gly Thr Ala Ser Gln Val Ser Arg
            340                 345                 350

Trp Ile Thr Ser Ser Ser Asn Leu Gln Pro Gly Thr Asp Leu Lys
                355                 360                 365

Val Thr Asp Asn His Phe Trp Ala His Leu Pro Ala Gln Ser Val Thr
            370                 375                 380

Thr Phe Val Val Lys Arg
385                 390

<210> SEQ ID NO 6
<211> LENGTH: 391
<212> TYPE: PRT
<213> ORGANISM: Bacillus licheniformis

<400> SEQUENCE: 6

Ala Ser Asp Ala Thr Val Arg Leu Ser Ala Glu Lys Gln Val Ile Arg
1               5                   10                  15

Gly Phe Gly Gly Met Asn His Pro Ala Trp Ile Gly Asp Leu Thr Ala
                20                  25                  30

Ala Gln Arg Glu Thr Ala Phe Gly Asn Gly Gln Asn Gln Leu Gly Phe
            35                  40                  45

Ser Ile Leu Arg Ile His Val Asp Glu Asn Arg Asn Asn Trp Tyr Arg
        50                  55                  60

Glu Val Glu Thr Ala Lys Ser Ala Ile Lys His Gly Ala Ile Val Phe
65                  70                  75                  80

Ala Ser Pro Trp Asn Pro Pro Ser Asp Met Val Glu Thr Phe Asn Arg
                85                  90                  95

Asn Gly Asp Thr Ser Ala Lys Arg Leu Arg Tyr Asp Lys Tyr Ala Ala
            100                 105                 110

Tyr Ala Lys His Leu Asn Asp Phe Val Thr Phe Met Lys Asn Asn Gly
        115                 120                 125

Val Asn Leu Tyr Ala Ile Ser Val Gln Asn Glu Pro Asp Tyr Ala His
        130                 135                 140

Asp Trp Thr Trp Trp Thr Pro Gln Glu Ile Leu Arg Phe Met Lys Glu
145                 150                 155                 160

Asn Ala Gly Ser Ile Asn Ala Arg Val Ile Ala Pro Glu Ser Phe Gln
                165                 170                 175
```

```
Tyr Leu Lys Asn Ile Ser Asp Pro Ile Val Asn Asp Pro Lys Ala Leu
            180                 185                 190

Ala Asn Met Asp Ile Leu Gly Ala His Leu Tyr Gly Thr Gln Leu Asn
        195                 200                 205

Asn Phe Ala Tyr Pro Leu Phe Lys Gln Lys Gly Ala Gly Lys Asp Leu
    210                 215                 220

Trp Met Thr Glu Val Tyr Tyr Pro Asn Ser Asp Asn His Ser Ala Asp
225                 230                 235                 240

Arg Trp Pro Glu Ala Leu Asp Val Ser His Ile His Asn Ser Met
            245                 250                 255

Val Glu Gly Asp Phe Gln Ala Tyr Val Trp Trp Tyr Ile Arg Arg Ser
        260                 265                 270

Tyr Gly Pro Met Lys Glu Asp Gly Thr Ile Ser Lys Arg Gly Tyr Asn
    275                 280                 285

Met Ala His Phe Ser Lys Phe Val Arg Pro Gly Tyr Val Arg Val Asp
290                 295                 300

Ala Thr Lys Ser Pro Ala Ser Asn Val Tyr Val Ser Ala Tyr Lys Gly
305                 310                 315                 320

Asp Asn Lys Val Val Ile Val Ala Ile Asn Lys Asn Asn Ser Gly Val
            325                 330                 335

Asn Gln Asn Phe Val Leu Gln Asn Gly Ser Val Ser Gln Val Ser Arg
        340                 345                 350

Trp Ile Thr Ser Ser Ser Asn Leu Gln Pro Gly Thr Asn Leu Asn
    355                 360                 365

Val Thr Asp Asn His Phe Trp Ala His Leu Pro Ala Gln Ser Val Thr
    370                 375                 380

Thr Phe Val Ala Asn Leu Arg
385                 390

<210> SEQ ID NO 7
<211> LENGTH: 392
<212> TYPE: PRT
<213> ORGANISM: Paenibacillus pabuli

<400> SEQUENCE: 7

Ala Ser Asp Val Thr Val Asn Leu Ser Ser Glu Lys Gln Leu Ile Lys
1               5                   10                  15

Gly Phe Gly Gly Ile Asn His Pro Asn Trp Ile Gly Asp Leu Thr Pro
            20                  25                  30

Ser Gln Arg Asp Thr Ala Phe Gly Asn Gly Gln Asn Gln Leu Gly Phe
        35                  40                  45

Ser Ile Leu Arg Ile Tyr Ile Asp Asp Asn Lys Asn Asn Trp Tyr Lys
50                  55                  60

Glu Ile Pro Thr Ala Lys Arg Ala Ile Glu Gln Gly Ala Ile Val Phe
65                  70                  75                  80

Ala Ser Pro Trp Asn Pro Pro Ser Asp Met Val Glu Thr Phe Asn Arg
            85                  90                  95

Asn Gly Asp Thr Ala Ala Lys Arg Leu Lys Tyr Asp Lys Tyr Ala Ala
        100                 105                 110

Tyr Ala Gln His Leu Asn Asp Phe Val Ser Tyr Met Lys Ser Asn Gly
    115                 120                 125

Val Asn Leu Tyr Ala Ile Ser Val Gln Asn Glu Pro Asp Tyr Ala His
    130                 135                 140

Asp Trp Thr Trp Trp Thr Pro Gln Glu Met Leu Arg Phe Met Lys Asp
145                 150                 155                 160
```

```
Tyr Ala Gly Ser Ile Thr Gly Thr Lys Val Met Ala Pro Glu Ser Phe
                165                 170                 175

Ser Tyr Leu Lys Glu Met Ser Asp Pro Ile Leu Asn Asp Pro Gln Ala
            180                 185                 190

Leu Ala Asn Met Asp Ile Leu Gly Ala His Thr Tyr Gly Thr Gln Phe
        195                 200                 205

Ser Asn Phe Pro Tyr Pro Leu Phe Lys Gln Lys Gly Ala Gly Lys Glu
    210                 215                 220

Leu Trp Met Ser Glu Val Tyr Tyr Pro Asn Ser Asn Ala Asn Ser Ala
225                 230                 235                 240

Asp His Trp Pro Glu Ala Leu Asp Val Ser Tyr His Ile His His Ala
                245                 250                 255

Met Val Glu Ala Asp Phe Gln Ala Tyr Val Trp Trp Tyr Ile Arg Arg
            260                 265                 270

Gln Tyr Gly Pro Met Lys Glu Asp Gly Thr Ile Ser Lys Arg Gly Tyr
        275                 280                 285

Asn Met Ala His Phe Ser Lys Phe Val Arg Pro Gly Phe Val Arg Val
    290                 295                 300

Asp Ala Thr Lys Asn Pro Asp Thr Gln Thr Phe Ile Ser Ala Phe Lys
305                 310                 315                 320

Gly Asp Asn Lys Val Val Ile Val Ala Ile Asn Arg Gly Thr Ser Ala
                325                 330                 335

Val Asn Gln Lys Phe Val Leu Gln Asn Gly Asn Ala Ser Asn Val Ser
            340                 345                 350

Ser Trp Val Thr Asp Ser Thr Arg Asn Leu Ala Ala Gly Ser Ser Ile
        355                 360                 365

Ile Met Thr Gly Asn Thr Phe Thr Ala Gln Leu Pro Ser Gln Ser Val
    370                 375                 380

Thr Thr Phe Val Ala Gln Leu Asn
385                 390

<210> SEQ ID NO 8
<211> LENGTH: 532
<212> TYPE: PRT
<213> ORGANISM: Aspergillus fumigatus

<400> SEQUENCE: 8

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Ser Gln Gln Lys
        115                 120                 125

Asn Ile Gly Ser Arg Leu Tyr Met Met Lys Asp Asp Ser Thr Tyr Glu
```

```
              130                 135                 140
Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
            195                 200                 205

Ile Asn Gly Gln Ala Asn Val Glu Gly Trp Gln Pro Ser Ser Asn Asp
        210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
            275                 280                 285

Phe Asn Ser Phe Arg Gln Gly Asn Lys Thr Phe Tyr Gly Pro Gly Met
        290                 295                 300

Thr Val Asp Thr Lys Ser Lys Phe Thr Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
            355                 360                 365

Leu Phe Gln Asp Gln Asn Val Phe Glu Lys His Gly Gly Leu Glu Gly
        370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
            435                 440                 445

Val Val Tyr Ser Asn Ile Lys Val Gly Pro Ile Gly Ser Thr Phe Asn
        450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
            515                 520                 525

Ser Gln Cys Leu
    530

<210> SEQ ID NO 9
```

<211> LENGTH: 454
<212> TYPE: PRT
<213> ORGANISM: Aspergillus fumigatus

<400> SEQUENCE: 9

```
Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
            35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
```

```
                385                 390                 395                 400
Trp Ile Lys Pro Gly Gly Glu Ser Asp Gly Thr Ser Asn Ser Thr Ser
                    405                 410                 415

Pro Arg Tyr Asp Ala His Cys Gly Tyr Ser Asp Ala Leu Gln Pro Ala
                    420                 425                 430

Pro Glu Ala Gly Thr Trp Phe Gln Ala Tyr Phe Glu Gln Leu Leu Thr
                    435                 440                 445

Asn Ala Asn Pro Ser Phe
                    450

<210> SEQ ID NO 10
<211> LENGTH: 863
<212> TYPE: PRT
<213> ORGANISM: Aspergillus fumigatus

<400> SEQUENCE: 10

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                    20                  25                  30

Trp Ala Asp Gly Gln Gly Glu Trp Ala Asp Ala His Arg Arg Ala Val
                35                  40                  45

Glu Ile Val Ser Gln Met Thr Leu Ala Glu Lys Val Asn Leu Thr Thr
        50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
                    100                 105                 110

Val Ala Ala Thr Trp Asp Lys Thr Leu Ala Tyr Leu Arg Gly Lys Ala
                115                 120                 125

Met Gly Glu Glu Phe Asn Asp Lys Gly Val Asp Ile Leu Leu Gly Pro
        130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
                    180                 185                 190

Ile Leu Asn Glu Gln Glu His Phe Arg Gln Val Gly Glu Ala Gln Gly
                195                 200                 205

Tyr Gly Tyr Asn Ile Thr Glu Thr Ile Ser Ser Asn Val Asp Asp Lys
        210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
                    260                 265                 270

Gly Phe Gln Gly Phe Val Met Ser Asp Trp Ser Ala His His Ser Gly
                275                 280                 285

Val Gly Ala Ala Leu Ala Gly Leu Asp Met Ser Met Pro Gly Asp Ile
        290                 295                 300
```

-continued

```
Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
            325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
            370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
            405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
            530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
            565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
            595                 600                 605

Gly Ala Pro Leu Leu Thr Glu Pro Asn Asn Gly Asn Gly Ala Pro Gln
610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
            645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
            690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
```

```
                    725                 730                 735
Pro Glu Gly Ala Arg Asp Gly Ser Pro Gln Pro Leu Leu Lys Ala Gly
                740                 745                 750

Gly Ala Pro Gly Gly Asn Pro Thr Leu Tyr Gln Asp Leu Val Arg Val
                755                 760                 765

Ser Ala Thr Ile Thr Asn Thr Gly Asn Val Ala Gly Tyr Glu Val Pro
            770                 775                 780

Gln Leu Tyr Val Ser Leu Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
                820                 825                 830

Gln Asp Trp Val Ile Thr Lys Tyr Pro Lys Lys Val His Val Gly Ser
                835                 840                 845

Ser Ser Arg Lys Leu Pro Leu Arg Ala Pro Leu Pro Arg Val Tyr
                850                 855                 860

<210> SEQ ID NO 11
<211> LENGTH: 253
<212> TYPE: PRT
<213> ORGANISM: Penicillium emersonii

<400> SEQUENCE: 11

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
                20                  25                  30

Val Ile Gly Asp Gln Phe Tyr Ser Gly Tyr Ile Val Asn Ser Phe Pro
            35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65              70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240
```

```
Ala Thr Tyr Thr Ile Pro Gly Pro Pro Glu Pro Thr Phe
                245                 250
```

```
<210> SEQ ID NO 12
<211> LENGTH: 515
<212> TYPE: PRT
<213> ORGANISM: Bacillus stearothermophilus

<400> SEQUENCE: 12
```

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365
```

Tyr Tyr Gly Ile Pro Gln Tyr Asn Ile Pro Ser Leu Lys Ser Lys Ile
            370             375             380

Asp Pro Leu Leu Ile Ala Arg Arg Asp Tyr Ala Tyr Gly Thr Gln His
385             390             395             400

Asp Tyr Leu Asp His Ser Asp Ile Ile Gly Trp Thr Arg Glu Gly Val
                405             410             415

Thr Glu Lys Pro Gly Ser Gly Leu Ala Ala Leu Ile Thr Asp Gly Pro
            420             425             430

Gly Gly Ser Lys Trp Met Tyr Val Gly Lys Gln His Ala Gly Lys Val
            435             440             445

Phe Tyr Asp Leu Thr Gly Asn Arg Ser Asp Thr Val Thr Ile Asn Ser
            450             455             460

Asp Gly Trp Gly Glu Phe Lys Val Asn Gly Gly Ser Val Ser Val Trp
465             470             475             480

Val Pro Arg Lys Thr Thr Val Ser Thr Ile Ala Arg Pro Ile Thr Thr
                485             490             495

Arg Pro Trp Thr Gly Glu Phe Val Arg Trp Thr Glu Pro Arg Leu Val
            500             505             510

Ala Trp Pro
        515

<210> SEQ ID NO 13
<211> LENGTH: 356
<212> TYPE: PRT
<213> ORGANISM: Dictyogllomus thermophilum

<400> SEQUENCE: 13

Met Lys Lys Pro Leu Gly Lys Ile Val Ala Ser Thr Ala Leu Leu Ile
1               5               10              15

Ser Val Ala Phe Ser Ser Ser Ile Ala Ser Ala Lys Glu Glu Ala Lys
            20              25              30

Gly Met Glu Ile Pro Ser Leu Lys Glu Val Tyr Lys Asp Tyr Phe Thr
        35              40              45

Ile Gly Ala Ala Val Ser His Leu Asn Ile Tyr His Tyr Glu Asn Leu
    50              55              60

Leu Lys Lys His Phe Asn Ser Leu Thr Pro Glu Asn Gln Met Lys Trp
65              70              75              80

Glu Val Ile His Pro Lys Pro Tyr Val Tyr Asp Phe Gly Pro Ala Asp
                85              90              95

Glu Ile Val Asp Phe Ala Met Lys Asn Gly Met Lys Val Arg Gly His
            100             105             110

Thr Leu Val Trp His Asn Gln Thr Pro Gly Trp Val Tyr Ala Gly Thr
        115             120             125

Lys Asp Glu Ile Leu Ala Arg Leu Lys Glu His Ile Lys Glu Val Val
    130             135             140

Gly His Tyr Lys Gly Lys Val Tyr Ala Trp Asp Val Val Asn Glu Ala
145             150             155             160

Leu Ser Asp Asn Pro Asn Glu Phe Leu Arg Arg Ala Pro Trp Tyr Asp
                165             170             175

Ile Cys Gly Glu Glu Val Ile Glu Lys Ala Phe Ile Trp Ala His Glu
            180             185             190

Val Asp Pro Asp Ala Lys Leu Phe Tyr Asn Asp Tyr Asn Leu Glu Asp
        195             200             205

Pro Ile Lys Arg Glu Lys Ala Tyr Lys Leu Val Lys Lys Leu Lys Asp

```
            210                 215                 220
Lys Gly Val Pro Ile His Gly Ile Gly Ile Gln Gly His Trp Thr Leu
225                 230                 235                 240

Ala Trp Pro Thr Pro Lys Met Leu Glu Asp Ser Ile Lys Arg Phe Ala
                245                 250                 255

Glu Leu Gly Val Glu Val Gln Val Thr Glu Phe Asp Ile Ser Ile Tyr
                260                 265                 270

Tyr Asp Arg Asn Glu Asn Asn Asn Phe Lys Val Pro Pro Glu Asp Arg
            275                 280                 285

Leu Glu Arg Gln Ala Gln Leu Tyr Lys Glu Ala Phe Glu Ile Leu Arg
        290                 295                 300

Lys Tyr Lys Gly Ile Val Thr Gly Val Thr Phe Trp Gly Val Ala Asp
305                 310                 315                 320

Asp Tyr Thr Trp Leu Tyr Phe Trp Pro Val Arg Gly Arg Glu Asp Tyr
                325                 330                 335

Pro Leu Leu Phe Asp Lys Asn His Asn Pro Lys Lys Ala Phe Trp Glu
                340                 345                 350

Ile Val Lys Phe
            355

<210> SEQ ID NO 14
<211> LENGTH: 203
<212> TYPE: PRT
<213> ORGANISM: Dictyogllomus thermophilum

<400> SEQUENCE: 14

Gln Thr Ser Ile Thr Leu Thr Ser Asn Ala Ser Gly Thr Phe Asp Gly
1               5                   10                  15

Tyr Tyr Tyr Glu Leu Trp Lys Asp Thr Gly Asn Thr Thr Met Thr Val
            20                  25                  30

Tyr Thr Gln Gly Arg Phe Ser Cys Gln Trp Ser Asn Ile Asn Asn Ala
        35                  40                  45

Leu Phe Arg Thr Gly Lys Lys Tyr Asn Gln Asn Trp Gln Ser Leu Gly
    50                  55                  60

Thr Ile Arg Ile Thr Tyr Ser Ala Thr Tyr Asn Pro Asn Gly Asn Ser
65                  70                  75                  80

Tyr Leu Cys Ile Tyr Gly Trp Ser Thr Asn Pro Leu Val Glu Phe Tyr
                85                  90                  95

Ile Val Glu Ser Trp Gly Asn Trp Arg Pro Pro Gly Ala Thr Ser Leu
            100                 105                 110

Gly Gln Val Thr Ile Asp Gly Thr Tyr Asp Ile Tyr Arg Thr Thr
        115                 120                 125

Arg Val Asn Gln Pro Ser Ile Val Gly Thr Ala Thr Phe Asp Gln Tyr
    130                 135                 140

Trp Ser Val Arg Thr Ser Lys Arg Thr Ser Gly Thr Val Thr Val Thr
145                 150                 155                 160

Asp His Phe Arg Ala Trp Ala Asn Arg Gly Leu Asn Leu Gly Thr Ile
                165                 170                 175

Asp Gln Ile Thr Leu Cys Val Glu Gly Tyr Gln Ser Ser Gly Ser Ala
            180                 185                 190

Asn Ile Thr Gln Asn Thr Phe Ser Gln Gly Ser
        195                 200

<210> SEQ ID NO 15
<211> LENGTH: 383
```

<212> TYPE: PRT
<213> ORGANISM: Rasomsonia byssochlamydoides

<400> SEQUENCE: 15

```
Asp Gly Leu Asn Thr Ala Ala Lys Ala Ile Gly Lys Leu Tyr Phe Gly
1               5                   10                  15

Thr Ala Thr Asp Asn Pro Glu Leu Ser Asp Val Ala Tyr Glu Thr Gln
            20                  25                  30

Leu Asn Asn Thr Gln Asp Phe Gly Gln Ile Thr Pro Ala Asn Ser Met
                35                  40                  45

Lys Trp Asp Ala Thr Glu Pro Glu Gln Asn Thr Phe Thr Phe Ala Ala
        50                  55                  60

Gly Asp Gln Ile Ala Asp Leu Ala Glu Ala Asn Gly Gln Ile Leu Arg
65                  70                  75                  80

Cys His Asn Leu Val Trp Tyr Asn Gln Leu Pro Ser Trp Val Thr Ser
                85                  90                  95

Gly Ser Trp Thr Asn Glu Thr Leu Leu Ala Ala Met Lys Asn His Ile
            100                 105                 110

Thr Asn Val Val Thr His Tyr Lys Gly Arg Cys Tyr Ala Trp Asp Val
                115                 120                 125

Val Asn Glu Ala Leu Asn Asp Asp Gly Thr Tyr Arg Asp Asn Val Phe
130                 135                 140

Tyr Gln Tyr Ile Gly Glu Ala Tyr Ile Pro Ile Ala Phe Glu Thr Ala
145                 150                 155                 160

Ala Ala Ala Asp Pro Asn Val Lys Leu Tyr Tyr Asn Asp Tyr Asn Ile
                165                 170                 175

Glu Tyr Ala Gly Val Lys Ala Thr Ala Ala Gln Asn Ile Val Lys Leu
            180                 185                 190

Val Gln Ser Tyr Gly Ala Arg Ile Asp Gly Val Gly Leu Gln Ser His
                195                 200                 205

Phe Ile Val Gly Glu Thr Pro Ser Thr Ser Gln Ala Ser Asn Met
210                 215                 220

Ala Ser Phe Thr Ala Leu Gly Val Glu Val Ala Ile Thr Glu Leu Asp
225                 230                 235                 240

Ile Arg Met Gln Leu Pro Glu Thr Thr Ala Leu Leu Thr Gln Gln Ser
                245                 250                 255

Thr Asp Tyr Gln Ser Thr Val Gln Ala Cys Val Asn Thr Pro Gly Cys
            260                 265                 270

Val Gly Ile Thr Leu Trp Asp Trp Thr Asp Lys Tyr Ser Trp Val Pro
                275                 280                 285

Ser Thr Phe Ser Gly Tyr Gly Asp Ala Cys Pro Trp Asp Asp Asn Tyr
290                 295                 300

Gln Lys Lys Pro Ala Tyr Tyr Gly Ile Leu Thr Ala Leu Gly Gly Ser
305                 310                 315                 320

Ala Ser Thr Thr Thr Val Gly Thr Gly Thr Thr Thr Ser Thr Ala
                325                 330                 335

Thr Thr Ser Ser Thr Gly Ser Ser Gly Thr Gly Val Ala Gln His Trp
                340                 345                 350

Gly Gln Cys Gly Gly Ile Gly Trp Thr Gly Pro Thr Val Cys Ala Ser
                355                 360                 365

Gly Tyr Thr Cys Thr Val Val Asn Pro Tyr Tyr Ser Gln Cys Leu
370                 375                 380
```

<210> SEQ ID NO 16

```
<211> LENGTH: 385
<212> TYPE: PRT
<213> ORGANISM: Talaromyces leycettanus

<400> SEQUENCE: 16

Ala Gly Leu Asn Thr Ala Ala Lys Ala Ile Gly Lys Leu Tyr Phe Gly
1               5                   10                  15

Thr Ala Thr Asp Asn Pro Glu Leu Ser Asp Ser Thr Tyr Met Gln Glu
            20                  25                  30

Thr Asp Asn Thr Asp Asp Phe Gly Gln Leu Thr Pro Ala Asn Ser Met
        35                  40                  45

Lys Trp Asp Ala Thr Glu Pro Ser Gln Asn Thr Phe Thr Phe Thr Asn
50                  55                  60

Gly Asp Gln Ile Ala Asn Leu Ala Lys Ser Asn Gly Gln Met Leu Arg
65                  70                  75                  80

Cys His Asn Leu Val Trp Tyr Asn Gln Leu Pro Ser Trp Val Thr Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Gln Cys Tyr Ala Trp Asp Val
        115                 120                 125

Val Asn Glu Ala Leu Asn Asp Asp Gly Thr Tyr Arg Ser Asn Val Phe
130                 135                 140

Tyr Gln Tyr Ile Gly Glu Ala Tyr Ile Pro Ile Ala Phe Ala Thr Ala
145                 150                 155                 160

Ala Ala Ala Asp Pro Asn Ala Lys Leu Tyr Tyr Asn Asp Tyr Asn Ile
                165                 170                 175

Glu Tyr Pro Gly Ala Lys Ala Thr Ala Ala Gln Asn Ile Val Lys Met
            180                 185                 190

Val Lys Ala Tyr Gly Ala Lys Ile Asp Gly Val Gly Leu Gln Ser His
        195                 200                 205

Phe Ile Val Gly Ser Thr Pro Ser Gln Ser Ser Gln Ser Asn Met
210                 215                 220

Ala Ala Phe Thr Ala Leu Gly Val Glu Val Ala Ile Thr Glu Leu Asp
225                 230                 235                 240

Ile Arg Met Thr Leu Pro Ser Thr Ser Ala Leu Leu Ala Gln Gln Ser
                245                 250                 255

Thr Asp Tyr Gln Ser Thr Val Ser Ala Cys Val Asn Thr Pro Lys Cys
            260                 265                 270

Ile Gly Ile Thr Leu Trp Asp Trp Thr Asp Lys Tyr Ser Trp Val Pro
        275                 280                 285

Asn Thr Phe Ser Gly Gln Gly Asp Ala Cys Pro Trp Asp Ser Asn Tyr
290                 295                 300

Gln Lys Lys Pro Ala Tyr Tyr Gly Ile Leu Thr Ala Leu Gly Gly Ser
305                 310                 315                 320

Ala Ser Thr Ser Thr Thr Thr Thr Leu Val Thr Ser Thr Arg Thr Ser
                325                 330                 335

Thr Thr Thr Ser Thr Ser Ala Thr Ser Thr Thr Gly Val Ala Gln
            340                 345                 350

His Trp Gly Gln Cys Gly Gly Ile Gly Trp Thr Gly Pro Thr Thr Cys
        355                 360                 365

Ala Ser Pro Tyr Thr Cys Gln Glu Leu Asn Pro Tyr Tyr Gln Cys
370                 375                 380

Leu
```

<210> SEQ ID NO 17
<211> LENGTH: 378
<212> TYPE: PRT
<213> ORGANISM: Aspergillus fumigatus

<400> SEQUENCE: 17

Ala Gly Leu Asn Thr Ala Ala Lys Ala Lys Gly Leu Lys Tyr Phe Gly
1               5                   10                  15

Ser Ala Thr Asp Asn Pro Glu Leu Thr Asp Ser Ala Tyr Val Ala Gln
            20                  25                  30

Leu Ser Asn Thr Asp Asp Phe Gly Gln Ile Thr Pro Gly Asn Ser Met
        35                  40                  45

Lys Trp Asp Ala Thr Glu Pro Ser Gln Asn Ser Phe Ser Phe Ala Asn
50                  55                  60

Gly Asp Ala Val Val Asn Leu Ala Asn Lys Asn Gly Gln Leu Met Arg
65                  70                  75                  80

Cys His Thr Leu Val Trp His Ser Gln Leu Pro Asn Trp Val Ser Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Lys Cys Tyr Ala Trp Asp Val
        115                 120                 125

Val Asn Glu Ala Leu Asn Glu Asp Gly Thr Phe Arg Asn Ser Val Phe
130                 135                 140

Tyr Gln Ile Ile Gly Pro Ala Tyr Ile Pro Ile Ala Phe Ala Thr Ala
145                 150                 155                 160

Ala Ala Ala Asp Pro Asp Val Lys Leu Tyr Tyr Asn Asp Tyr Asn Ile
                165                 170                 175

Glu Tyr Ser Gly Ala Lys Ala Thr Ala Ala Gln Asn Ile Val Lys Met
            180                 185                 190

Ile Lys Ala Tyr Gly Ala Lys Ile Asp Gly Val Gly Leu Gln Ala His
        195                 200                 205

Phe Ile Val Gly Ser Thr Pro Ser Gln Ser Asp Leu Thr Thr Val Leu
210                 215                 220

Lys Gly Tyr Thr Ala Leu Gly Val Glu Val Ala Tyr Thr Glu Leu Asp
225                 230                 235                 240

Ile Arg Met Gln Leu Pro Ser Thr Ala Ala Lys Leu Ala Gln Gln Ser
                245                 250                 255

Thr Asp Phe Gln Gly Val Ala Ala Cys Val Ser Thr Thr Gly Cys
            260                 265                 270

Val Gly Val Thr Ile Trp Asp Trp Thr Asp Lys Tyr Ser Trp Val Pro
        275                 280                 285

Ser Val Phe Gln Gly Tyr Gly Ala Pro Leu Pro Trp Asp Glu Asn Tyr
290                 295                 300

Val Lys Lys Pro Ala Tyr Asp Gly Leu Met Ala Gly Leu Gly Ala Ser
305                 310                 315                 320

Gly Ser Gly Thr Thr Thr Thr Thr Thr Thr Ser Thr Thr Thr Gly
                325                 330                 335

Gly Thr Asp Pro Thr Gly Val Ala Gln Lys Trp Gly Gln Cys Gly Gly
            340                 345                 350

Ile Gly Trp Thr Gly Pro Thr Cys Val Ser Gly Thr Thr Cys Gln
        355                 360                 365

```
Lys Leu Asn Asp Trp Tyr Ser Gln Cys Leu
    370                 375
```

<210> SEQ ID NO 18
<211> LENGTH: 409
<212> TYPE: PRT
<213> ORGANISM: Talaromyces leycettanus

<400> SEQUENCE: 18

```
Met Lys Phe Ser Asn Val Ile Leu Ala Ala Ser Ala Ser Ser Leu Val
1               5                   10                  15

Leu Ala Ala Pro Lys Ser Lys Thr Lys Arg Thr Ser Ala Phe Gln Trp
            20                  25                  30

Phe Gly Ala Asn Glu Ser Gly Ala Glu Phe Gly Asn Gln Asn Ile Pro
        35                  40                  45

Gly Thr Leu Gly Thr Asp Tyr Thr Trp Pro Asp Thr Ser Thr Ile Gln
    50                  55                  60

Thr Leu Arg Asn Ala Gly Met Asn Ile Phe Arg Val Pro Phe Leu Met
65                  70                  75                  80

Glu Arg Leu Val Pro Asn Gln Met Thr Gly Ser Pro Asp Pro Thr Tyr
                85                  90                  95

Leu Ala Asp Leu Lys Ser Thr Val Asn Phe Ile Thr Gly Thr Gly Ala
            100                 105                 110

Tyr Ala Val Val Asp Pro His Asn Tyr Gly Arg Tyr Tyr Asn Asn Ile
        115                 120                 125

Ile Thr Ser Thr Ser Asp Phe Ala Ala Phe Trp Thr Thr Val Ala Ser
    130                 135                 140

Gln Phe Ala Ser Asn Pro Arg Val Ile Phe Asp Thr Asn Asn Glu Tyr
145                 150                 155                 160

Asn Asn Met Asp Gln Thr Leu Val Leu Asn Leu Asn Gln Ala Ala Ile
                165                 170                 175

Asn Ala Ile Arg Ala Ala Gly Ala Thr Ser Gln Tyr Ile Phe Ala Glu
            180                 185                 190

Gly Asn Ser Trp Thr Gly Ala Trp Thr Trp Thr Ser Val Asn Asp Asn
        195                 200                 205

Met Lys Gln Leu Thr Asp Pro Ser Asn Lys Leu Val Tyr Glu Met His
    210                 215                 220

Gln Tyr Leu Asp Ser Asp Gly Ser Gly Thr Ser Asp Gln Cys Val Asn
225                 230                 235                 240

Ser Thr Ile Gly Tyr Asp Arg Ile Val Ser Ala Thr Gln Trp Leu Gln
                245                 250                 255

Ala Asn Gly Lys Val Ala Phe Leu Gly Glu Phe Ala Gly Gly Ser Asn
            260                 265                 270

Ser Val Cys Glu Ala Ala Val Thr Gly Met Leu Asp Tyr Met Glu Gln
        275                 280                 285

Asn Ser Asp Val Trp Leu Gly Ala Glu Trp Trp Ala Ala Gly Pro Trp
    290                 295                 300

Trp Gly Asn Tyr Ile Tyr Ser Met Glu Pro Pro Ser Gly Ile Ala Tyr
305                 310                 315                 320

Gln Asn Tyr Leu Ser Ile Leu Glu Pro Tyr Phe Pro Gly Gly Ser Tyr
                325                 330                 335

Ser Gly Gly Thr Gly Ser Gly Ser Gly Ser Thr Thr Thr Ala Thr
            340                 345                 350

Thr Thr Thr Thr Lys Val Pro Pro Thr Ser Thr Ser Ser Ala Ser
        355                 360                 365
```

```
Ser Thr Gly Thr Gly Val Ala Gln His Trp Gly Gln Cys Gly Gly Gln
    370                 375                 380

Gly Trp Thr Gly Pro Thr Cys Val Ser Pro Tyr Thr Cys Gln Glu
385                 390                 395                 400

Leu Asn Pro Tyr Tyr Tyr Gln Cys Leu
                405

<210> SEQ ID NO 19
<211> LENGTH: 334
<212> TYPE: PRT
<213> ORGANISM: Penicillium capsulatum

<400> SEQUENCE: 19

Met Lys Phe Ser Asn Leu Val Ala Leu Ala Ala Ala Ser Ser Ala
1               5                   10                  15

Met Ala Leu Pro Leu Thr Lys Lys His Ala Lys Arg Ala Ser Ser Phe
                20                  25                  30

Glu Trp Phe Gly Ser Asn Glu Ser Gly Ala Glu Phe Gly Ser Gly Asn
            35                  40                  45

Ile Pro Gly Val Tyr Gly Thr Asp Tyr Ile Phe Pro Ser Thr Ser Ala
50                  55                  60

Ile Gln Thr Leu Ile Asn Asn Gly Met Asn Ile Phe Arg Val Thr Phe
65              70                  75                  80

Met Met Glu Arg Leu Val Pro Asn Thr Met Thr Gly Ser Phe Asp Ala
                85                  90                  95

Glu Tyr Leu Ser Asn Leu Thr Ser Val Val Asn Tyr Ile Thr Glu Ala
            100                 105                 110

Gly Ala His Ala Val Ile Asp Pro His Asn Tyr Gly Arg Tyr Tyr Gly
        115                 120                 125

Ser Ile Ile Ser Ser Thr Ser Asp Phe Gln Thr Phe Trp Lys Asn Val
130                 135                 140

Ala Gly Gln Phe Lys Ser Asn Ser Leu Val Ile Phe Asp Thr Asn Asn
145                 150                 155                 160

Glu Tyr His Asp Met Asp Gln Thr Leu Val Leu Asn Leu Asn Gln Ala
            165                 170                 175

Ala Ile Asn Gly Ile Arg Ala Ala Gly Ala Thr Ser Gln Tyr Ile Phe
            180                 185                 190

Val Glu Gly Asn Ser Tyr Thr Gly Ala Trp Thr Trp Ala Asp Val Asn
            195                 200                 205

Asp Asn Leu Lys Asn Leu Thr Asp Pro Gln Asn Lys Ile Val Tyr Glu
210                 215                 220

Met His Gln Tyr Leu Asp Ser Asp Gly Ser Gly Thr Ser Ala Thr Cys
225                 230                 235                 240

Val Ser Thr Thr Ile Gly Lys Glu Arg Val Thr Ser Ala Thr Gln Trp
                245                 250                 255

Leu Gln Lys Asn Gly Lys Val Gly Ile Leu Gly Glu Phe Ala Gly Gly
            260                 265                 270

Val Asn Asp Gln Cys Lys Thr Ala Ile Thr Gly Met Leu Ser Tyr Leu
        275                 280                 285

Glu Asp Asn Ser Asp Val Trp Arg Gly Ala Met Trp Ala Ala Gly
        290                 295                 300

Pro Trp Trp Gly Asp Tyr Ile Phe Ser Leu Glu Pro Pro Ser Gly Thr
305                 310                 315                 320

Ala Tyr Thr Gly Met Trp Ser Thr Leu Lys Ser Tyr Leu Ala
```

<210> SEQ ID NO 20
<211> LENGTH: 394
<212> TYPE: PRT
<213> ORGANISM: Trichophaea saccata

<400> SEQUENCE: 20

Met His Ser Phe Phe Ser Leu Ala Leu Ala Val Ala Gly Leu Pro Ala
1               5                   10                  15

Leu Ile Asn Ala Gln Gln Ser Ala Trp Gly Gln Cys Gly Gly Val Gly
            20                  25                  30

Trp Thr Gly Ala Thr Thr Cys Val Ser Gly Tyr Tyr Cys Ser Lys Leu
        35                  40                  45

Asn Asp Tyr Tyr Ser Gln Cys Ile Pro Gly Thr Ala Ser Thr Thr Thr
    50                  55                  60

Ser Ala Val Ser Thr Thr Thr Ala Thr Ser Pro Thr Gly Ser Val
65                  70                  75                  80

Cys Ser Gly Asn Arg Thr Lys Phe Lys Tyr Phe Gly Val Asn Glu Ser
                85                  90                  95

Gly Ala Glu Phe Gly Asn Asn Val Val Pro Gly Thr Leu Gly Lys Asp
            100                 105                 110

Tyr Thr Trp Pro Thr Thr Asp Ser Val Asp Phe Phe Leu Gly Lys Gly
        115                 120                 125

Met Asn Thr Phe Arg Ile Ala Phe Leu Met Glu Arg Leu Ser Pro Pro
130                 135                 140

Ala Gly Gly Leu Thr Gly Thr Phe Asp Pro Thr Tyr Leu Ala Ser Leu
145                 150                 155                 160

Lys Asn Ile Ala Ser Tyr Ile Thr Gly Lys Gly Gly Tyr Ala Ile Ile
                165                 170                 175

Asp Pro His Asn Tyr Gly Arg Tyr Asn Gly Asn Ile Ile Thr Asp Tyr
            180                 185                 190

Thr Ser Phe Gly Thr Trp Cys Lys Asn Leu Ala Ser Gln Phe Lys Ser
        195                 200                 205

Asp Ser His Ile Ile Phe Asp Thr Asn Asn Glu Tyr His Asp Met Asp
    210                 215                 220

Glu Thr Leu Val Phe Asn Leu Asn Gln Ala Cys Ile Asn Gly Ile Arg
225                 230                 235                 240

Ala Ala Gly Ala Thr Ser Gln Leu Ile Leu Ile Glu Gly Asn Ser Trp
                245                 250                 255

Thr Gly Ala Trp Thr Trp Ile Ser Ser Gly Asn Ala Ala Ser Leu Ile
            260                 265                 270

Asn Leu Thr Asp Pro Asn Asn Asn Ile Ala Tyr Glu Met His Gln Tyr
        275                 280                 285

Leu Asp Ser Asp Gly Ser Gly Thr Ser Pro Thr Cys Val Ser Ser Thr
    290                 295                 300

Ile Gly Ala Glu Arg Leu Ala Ala Ala Thr Ala Trp Leu Gln Ala Asn
305                 310                 315                 320

Asn Lys Lys Gly Phe Leu Gly Glu Ile Gly Ala Gly Ser Asn Asp Asp
                325                 330                 335

Cys Ile Ala Ala Val Lys Gly Ala Leu Cys Ser Met Gln Glu Ala Gly
            340                 345                 350

Gly Val Trp Leu Gly Ala Leu Trp Trp Ala Ala Gly Pro Trp Trp Gly
        355                 360                 365

```
Asp Tyr Tyr Gln Ser Ile Glu Pro Pro Asp Gly Ala Ala Ile Ala Arg
    370                 375                 380

Ile Leu Pro Glu Ala Leu Leu Pro Phe Leu
385                 390
```

<210> SEQ ID NO 21
<211> LENGTH: 294
<212> TYPE: PRT
<213> ORGANISM: Sordaria fimicola

<400> SEQUENCE: 21

```
Met Arg Ser Ser Thr Ile Leu Gln Thr Gly Leu Val Ala Val Leu Pro
1               5                   10                  15

Phe Ala Val Gln Ala Ala Ser Gly Ser Gly Lys Ser Thr Arg Tyr Trp
                20                  25                  30

Asp Cys Cys Lys Pro Ser Cys Ala Trp Ser Gly Lys Ala Ser Val Asn
            35                  40                  45

Arg Pro Val Leu Ala Cys Asp Ala Asn Asn Asn Pro Leu Asn Asp Ala
        50                  55                  60

Asn Val Lys Ser Gly Cys Asp Gly Gly Ser Ala Tyr Thr Cys Ala Asn
65                  70                  75                  80

Asn Ser Pro Trp Ala Val Asn Asp Asn Leu Ala Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ser Gly Lys Thr Leu Val Val
        115                 120                 125

Gln Ser Thr Ser Thr Gly Gly Asp Leu Gly Ser Asn His Phe Asp Leu
    130                 135                 140

Asn Met Pro Gly Gly Gly Val Gly Leu Phe Asp Gly Cys Lys Arg Glu
145                 150                 155                 160

Phe Gly Gly Leu Pro Gly Ala Gln Tyr Gly Gly Ile Ser Ser Arg Ser
                165                 170                 175

Glu Cys Asp Ser Phe Pro Ala Ala Leu Lys Pro Gly Cys Gln Trp Arg
            180                 185                 190

Phe Asp Trp Phe Lys Asn Ala Asp Asn Pro Glu Phe Thr Phe Lys Gln
        195                 200                 205

Val Gln Cys Pro Ser Glu Leu Thr Ser Arg Thr Gly Cys Lys Arg Asn
    210                 215                 220

Asp Asp Ser Gln Phe Pro Ala Phe Thr Pro Pro Ser Gly Gly Gly Ser
225                 230                 235                 240

Asn Pro Ser Thr Pro Thr Thr Pro Pro Ser Ser Gly Gly Gly Gly Ser
                245                 250                 255

Gly Cys Ala Ala Ala Met Tyr Ala Gln Cys Gly Gly Ser Gly Phe Ser
            260                 265                 270

Gly Cys Thr Asn Cys Pro Ser Gly Ser Thr Cys Lys Ala Ile Asn Asp
        275                 280                 285

Tyr Tyr His Gln Cys Ala
    290
```

<210> SEQ ID NO 22
<211> LENGTH: 278
<212> TYPE: PRT
<213> ORGANISM: Thielavia terrestris

<400> SEQUENCE: 22

```
Ala Ser Gly Ser Gly Gln Ser Thr Arg Tyr Trp Asp Cys Cys Lys Pro
1               5                   10                  15

Ser Cys Ala Trp Pro Gly Lys Ala Val Ser Gln Pro Val Tyr Ala
            20                  25                  30

Cys Asp Ala Asn Phe Gln Arg Leu Ser Asp Phe Asn Val Gln Ser Gly
        35                  40                  45

Cys Asn Gly Gly Ser Ala Tyr Ser Cys Ala Asp Gln Thr Pro Trp Ala
    50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn His Phe Asp Ile Ala Met Pro Gly Gly
            115                 120                 125

Gly Val Gly Ile Phe Asn Gly Cys Ser Ser Gln Phe Gly Gly Leu Pro
        130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
            165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
        195                 200                 205

Pro Val Phe Thr Pro Pro Ser Gly Gly Asn Gly Gly Thr Gly Thr Pro
        210                 215                 220

Thr Ser Thr Ala Pro Gly Ser Gly Gln Thr Ser Pro Gly Gly Gly Ser
225                 230                 235                 240

Gly Cys Thr Ser Gln Lys Trp Ala Gln Cys Gly Gly Ile Gly Phe Ser
                245                 250                 255

Gly Cys Thr Thr Cys Val Ser Gly Thr Thr Cys Gln Lys Leu Asn Asp
            260                 265                 270

Tyr Tyr Ser Gln Cys Leu
            275

<210> SEQ ID NO 23
<211> LENGTH: 595
<212> TYPE: PRT
<213> ORGANISM: Penicillium oxalicum

<400> SEQUENCE: 23

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95
```

-continued

```
Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510
```

Gly Asn Ile Thr Ala Leu Gly Asn Trp Asp Ala Lys Lys Gly Phe Pro
            515                 520                 525

Leu Thr Ala Asn Leu Tyr Thr Gln Asp Gln Asn Leu Trp Phe Ala Ser
        530                 535                 540

Val Glu Phe Ile Pro Ala Gly Thr Pro Phe Glu Tyr Lys Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595

<210> SEQ ID NO 24
<211> LENGTH: 412
<212> TYPE: PRT
<213> ORGANISM: Pyrococcus furiosus

<400> SEQUENCE: 24

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

```
Asp Ile Ala Tyr Gly Ala Gly Arg Val Asn Ala Tyr Lys Ala Ile Asn
        290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
                340                 345                 350

Tyr Asp Pro Asn Gly Asn Gln Val Asp Tyr Ser Tyr Thr Ala Tyr Tyr
                355                 360                 365

Gly Phe Glu Lys Val Gly Tyr Tyr Asn Pro Thr Asp Gly Thr Trp Thr
        370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 25
<211> LENGTH: 177
<212> TYPE: PRT
<213> ORGANISM: Thermoascus aurantiacus

<400> SEQUENCE: 25

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
            35                  40                  45

Ser Ser Thr Arg Gln Thr Val Ala Ala Arg Leu Arg Ala Val Ala Arg
        50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
        115                 120                 125

Glu Phe Thr His Ala Pro Gly Val Tyr Ser Pro Gly Thr Asp Asp Leu
    130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 26
<211> LENGTH: 583
<212> TYPE: PRT
<213> ORGANISM: Artificial Sequence
<220> FEATURE:
<223> OTHER INFORMATION: Rhizomucor pusillus alpha-amylase with
      Aspergillus niger glucoamylase linker and starch binding domain
      (SBD)

<400> SEQUENCE: 26
```

```
Ala Thr Ser Asp Asp Trp Lys Gly Lys Ala Ile Tyr Gln Leu Leu Thr
 1               5                  10                  15

Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
            35                  40                  45

Tyr Ile Ser Gly Met Gly Phe Asp Ala Ile Trp Ile Ser Pro Ile Pro
        50                  55                  60

Lys Asn Ser Asp Gly Gly Tyr His Gly Tyr Trp Ala Thr Asp Phe Tyr
 65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
                100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
        130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
                180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
                260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
        290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
                340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
        370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415
```

```
Val Ser Ser Asp Gly Thr Val Thr Phe Asn Leu Lys Asp Gly Leu Pro
            420             425             430

Ala Ile Phe Thr Ser Ala Thr Gly Gly Thr Thr Thr Thr Ala Thr Pro
            435             440             445

Thr Gly Ser Gly Ser Val Thr Ser Thr Ser Lys Thr Thr Ala Thr Ala
        450             455             460

Ser Lys Thr Ser Thr Ser Thr Ser Ser Thr Ser Cys Thr Thr Pro Thr
465             470             475             480

Ala Val Ala Val Thr Phe Asp Leu Thr Ala Thr Thr Thr Tyr Gly Glu
            485             490             495

Asn Ile Tyr Leu Val Gly Ser Ile Ser Gln Leu Gly Asp Trp Glu Thr
            500             505             510

Ser Asp Gly Ile Ala Leu Ser Ala Asp Lys Tyr Thr Ser Ser Asp Pro
            515             520             525

Leu Trp Tyr Val Thr Val Thr Leu Pro Ala Gly Glu Ser Phe Glu Tyr
            530             535             540

Lys Phe Ile Arg Ile Glu Ser Asp Asp Ser Val Glu Trp Glu Ser Asp
545             550             555             560

Pro Asn Arg Glu Tyr Thr Val Pro Gln Ala Cys Gly Thr Ser Thr Ala
            565             570             575

Thr Val Thr Asp Thr Trp Arg
            580
```